US012776419B2

(12) United States Patent
Aravamudan et al.

(10) Patent No.: US 12,776,419 B2
(45) Date of Patent: Oct. 27, 2026

(54) METHOD OF AND SYSTEM FOR DETECTION OF DURABILITY OF ANTIBODY RESPONSE TO VACCINATION

(71) Applicant: nference, inc., Cambridge, MA (US)

(72) Inventors: Murali Aravamudan, Andover, MA (US); Patrick J. Lenehan, Cambridge, MA (US); Venkataramanan Soundararajan, Andover, MA (US); Arjun Puranik, San Jose, CA (US)

(73) Assignee: nference, Inc., Cambridge, MA (US)

( * ) Notice: Subject to any disclaimer, the term of this patent is extended or adjusted under 35 U.S.C. 154(b) by 1057 days.

(21) Appl. No.: 17/961,263

(22) Filed: Oct. 6, 2022

(65) Prior Publication Data

US 2023/0105505 A1 Apr. 6, 2023

Related U.S. Application Data

(60) Provisional application No. 63/252,778, filed on Oct. 6, 2021.

(51) Int. Cl.
*G16H 50/70* (2018.01)
*G06F 21/62* (2013.01)
*G16H 50/80* (2018.01)

(52) U.S. Cl.
CPC ......... *G16H 50/70* (2018.01); *G06F 21/6245* (2013.01); *G16H 50/80* (2018.01)

(58) Field of Classification Search
CPC ........ G16H 50/70; G16H 50/80; G16H 10/40; G16H 10/60; G06F 21/6245
See application file for complete search history.

(56) References Cited

U.S. PATENT DOCUMENTS 7,542,969 B1 6/2009 Rappaport et al.
9,514,405 B2 12/2016 Chen et al.
(Continued)

FOREIGN PATENT DOCUMENTS

CN 105938495 A 9/2016
JP 2019-536178 A 12/2019
(Continued)

OTHER PUBLICATIONS

AMD Secure Encrypted Virtualization (SEV), https://developer.amd.com/sev/, accessed Sep. 23, 2020 (5 pages).
(Continued)

*Primary Examiner* — Blake I Narramore
(74) *Attorney, Agent, or Firm* — CALDWELL LLC

(57) ABSTRACT

This disclosure relates to systems including a plurality of secure enclaves, each in communication with a central node, wherein software within the secure enclave is configured to execute instructions on one or more processors by: receiving input data in an encrypted form; decrypting the input data using one or more cryptographic keys; executing application computing processes to generate output data; generating a proof of execution that proves that the one or more instructions of the one or more application computing processes operated on the received input data; and sending the output data to a central node; wherein software within the central node is configured to execute instructions on one or more processors by receiving the output data from the plurality of secure enclaves; executing application computing processes to apply an aggregate analysis to the output data of each of the secure enclaves; and providing an aggregate output.

37 Claims, 32 Drawing Sheets

(56) References Cited

U.S. PATENT DOCUMENTS

| | | | | |
|---|---|---|---|---|
| 9,953,095 | B1 * | 4/2018 | Scott | G06F 16/955 |
| 10,360,507 | B2 | 7/2019 | Aravamudan et al. | |
| 11,062,218 | B2 | 7/2021 | Aravamudan et al. | |
| 11,487,902 | B2 | 11/2022 | Ardhanari et al. | |
| 11,545,242 | B2 | 1/2023 | Aravamudan | |
| 2004/0013302 | A1 | 1/2004 | Ma et al. | |
| 2007/0039046 | A1 | 2/2007 | Van Dijk et al. | |
| 2008/0118150 | A1 | 5/2008 | Balakrishnan et al. | |
| 2008/0243825 | A1 | 10/2008 | Staddon et al. | |
| 2009/0116736 | A1 | 5/2009 | Neogi et al. | |
| 2011/0255788 | A1 | 10/2011 | Duggan et al. | |
| 2011/0307460 | A1 | 12/2011 | Vadlamani et al. | |
| 2013/0132331 | A1 | 5/2013 | Kowalczyk et al. | |
| 2015/0161413 | A1 | 6/2015 | Calem et al. | |
| 2015/0254555 | A1 | 9/2015 | Williams, Jr. et al. | |
| 2016/0105402 | A1 | 4/2016 | Soon-Shiong et al. | |
| 2016/0247307 | A1 | 8/2016 | Stoop et al. | |
| 2017/0032243 | A1 | 2/2017 | Corrado et al. | |
| 2017/0061326 | A1 | 3/2017 | Talathi et al. | |
| 2017/0091391 | A1 * | 3/2017 | LePendu | G06F 21/6245 |
| 2018/0060282 | A1 | 3/2018 | Kaljurand | |
| 2018/0212754 | A1 * | 7/2018 | Williams | G06F 16/254 |
| 2019/0319982 | A1 * | 10/2019 | Durand | H04L 63/04 |
| 2019/0354883 | A1 | 11/2019 | Aravamudan et al. | |
| 2020/0327250 | A1 * | 10/2020 | Wang | G06N 20/00 |
| 2020/0402625 | A1 * | 12/2020 | Aravamudan | G06F 21/6245 |
| 2021/0019287 | A1 | 1/2021 | Prasad et al. | |
| 2021/0224264 | A1 | 7/2021 | Barve et al. | |
| 2021/0248268 | A1 * | 8/2021 | Ardhanari | G06F 21/53 |
| 2022/0050921 | A1 * | 2/2022 | LaFever | G06F 21/6254 |
| 2022/0138599 | A1 | 5/2022 | Aravamudan et al. | |

FOREIGN PATENT DOCUMENTS

| | | | |
|---|---|---|---|
| WO | WO-2015084759 | A1 | 6/2015 |
| WO | WO-2015149114 | | 10/2015 |
| WO | WO-2018057945 | | 3/2018 |
| WO | WO-2020257783 | | 12/2020 |
| WO | WO-2021011776 | | 1/2021 |
| WO | WO-2021146694 | A1 | 7/2021 |
| WO | WO-2021178689 | | 9/2021 |

OTHER PUBLICATIONS

Arora, S. et al., “A Simple But Tough-To-Beat Baseline for Sentence Embeddings”, ICLR, 2017 (16 pages).

AWS Key Management Service (KMS), https://aws.amazon.com/kms, accessed Jan. 20, 2021 (3 pages).

AWS Key Management Service (KMS), https://aws.amazon.com/kms, accessed Sep. 23, 2020 (6 pages).

Bartunov, S. et al., “Breaking Sticks and Ambiguities With Adaptive Skip-Gram”, retrieved online from URL:< https://arxiv.org/pdf/1502.07257.pdf>, [cs.CL], Nov. 15, 2015 (15 pages).

Borenstein, et al., “A basic introduction to fixed-effect and random-effects models for meta-analysis”, Research Synthesis Methods, 1:97-111 (2010) (15 pages).

Confidential Computing Consortium, “What is the Confidential Computing Consortium?”, https://confidentialcomputing.io, accessed Sep. 24, 2020 (2 pages).

De Guzman, C.G. et al., “Hematopoietic Stem Cell Expansion and Distinct Myeloid Developmental Abnormalities in a Murine Model of the AML1-ETO Translocation”, Molecular and Cellular Biology, 22(15):5506-5517, Aug. 2002 (12 pages).

Desagulier, G., “A lesson from associative learning: asymmetry and productivity in multiple-slot constructions”, Corpus Linguistic and Linguistic Theory, 12(2): 173-219, 2016, submitted Aug. 13, 2015, <http://www.degruyter.com/view/j/cllt.2016.12.issue-2/cllt-2015-0012/cllt-2015-0012.xml?format=INT>. <10.1515/cllt-2015-0012>. <halshs-01184230>, (32 pages).

Devlin, J. et al., “BERT: Pre-training of Deep Bidirectional Transformers for Language Understanding”, arXiv:1810.04805v2 [cs.CL], May 24, 2019 (16 pages).

Divatia, “The Fact and Fiction of Homomorphic Encryption”, https://www.darkreading.com/attacks-breaches/the-fact-and-fiction-of-homomorphic-encryption/a/d-id/1333691, Jan. 22, 2019 (3 pages).

Dwork, C., “Differential Privacy: A Survey of Results”, Lecture Notes in Computer Science, vol. 4978, pp. 1-19, 2008 (19 pages).

Ferraiuolo, A. et al., “Komodo: Using verification to disentangle secure-enclave hardware from software”, SOSP ’17, Shanghai, China, pp. 287-305, Oct. 28, 2017 (19 pages).

Garten, Y. et al., “Pharmspresso: a text mining tool for extraction of pharmacogenomic concepts and relationships from full text”, BMC Bioinformatics, 10(Suppl. 2):S6, Feb. 5, 2009 (9 pages).

Genkin, D. et al., “Privacy in Decentralized Cryptocurrencies”, Communications of the ACM, 61(6):78-88, Jun. 2018 (11 pages).

Hageman, G.S. et al., “A common haplotype in the complement regulatory gene factor H (HF1 / CFH) predisposes individuals to age-related macular degeneration”, PNAS, 102(20):7227-7232, May 17, 2005 (6 pages).

Ikeda, T. et al., “Anticorresponding mutations of the KRAS and PTEN genes in human endometrial cancer”, Oncology Reports, 7: 567-570, published online May 1, 2000 (4 pages).

Intel, “What is Intel® SGX?”, http://www.intel.com/content/www/us/en/architecture-and-technology/software-guard-extensions.html, accessed Sep. 23, 2020 (8 pages).

International Preliminary Report on Patentability issued in International Application No. PCT/US2021/020906, Sep. 15, 2022 (9 pages).

International Search Report and Written Opinion issued by the European Patent Office as International Searching Authority in International Application PCT/US2017/053039, dated Dec. 20, 2017 (15 pages).

International Search Report and Written Opinion issued by the U.S. Patent and Trademark Office as International Searching Authority issued in International Application No. PCT/US21/20906, dated May 19, 2021 (10 pages).

International Search Report and Written Opinion issued by U.S. Patent and Trademark Office as International Searching Authority in International Application No. PCT/US20/42336, dated Sep. 30, 2020 (10 pages).

International Search Report and Written Opinion issued by U.S. Patent and Trademark Office as International Searching Authority, for International Application No. PCT/US20/38987, dated Nov. 9, 2020 (26 pages).

Joulin, A. et al., “Bag of Tricks for Efficient Text Classification”, retrieved online from URL:<https://arXiv.org/pdf/1607.01759v3.pdf>, [cs.CL], Aug. 9, 2016 (5 pages).

Kiros, R. et al., “Skip-Thought Vectors”, retrieved online from URL:<https://arXiv.org/abs/1506.06726v1>, [cs.CL], Jun. 22, 2015 (11 pages).

Kolte, “Why Is Homomorphic Encryption Not Ready for Primetime?”, Baffle, https://baffle.io/blog/why-is-homomorphic-encryption-not-ready-for-primetime/, Mar. 17, 2017 (3 pages).

Korger, C., “Clustering of Distributed Word Representations and its Applicability for Enterprise Search”, Doctoral Thesis, Dresden University of Technology, Faculty of Computer Science, Institute of Software and Multimedia Technology, Matriculation Nr. 3703541, submitted Jul. 28, 2016 (116 pages).

Kutuzov, A. et al., “Cross-lingual Trends Detection for Named Entities in News Texts with Dynamic Neural Embedding Models”, Proceedings of the NewsIR’16 Workshop at ECIR, Padua, Italy, Mar. 20, 2016 (6 pages).

Le, Q. et al., “Distributed Representations of Sentences and Documents”, Proceedings of the 31st International Conference of Machine Learning, Beijing, China, vol. 32, 2014 (9 pages).

Lewnard, et al., “Measurement of Vaccine Direct Effects Under the Test-Negative Design”, American Journal of Epidemiology, 187(12):2686-2697, Aug. 7, 2018 (12 pages).

Li, H. et al., “Cheaper and Better: Selecting Good Workers for Crowdsourcing,” retrieved online from URL: https://arXiv.org/abs/1502.00725v1, pp. 1-16, Feb. 3, 2015 (16 pages).

Ling, W. et al., “Two/Too Simple Adaptations of Word2Vec for Syntax Problems”, retrieved online from URL:<https://cs.cmu.edu/~lingwang/papers/naacl2015.pdf>, 2015 (6 pages).

(56) References Cited

OTHER PUBLICATIONS

Maxwell, K.N. et al., “Adenoviral-mediated expression of Pcsk9 in mice results in a low-density lipoprotein receptor knockout phenotype”, PNAS, 101(18):7100-7105, May 4, 2004 (6 pages).
Mikolov, T. et al., “Distributed Representations for Words and Phrases and their Compositionality”, retrieved online from URL:https://arXiv.org/abs/1310.4546v1 [cs.CL], Oct. 16, 2013 (9 pages).
Mikolov, T. et al., “Efficient Estimation of Word Representations in Vector Space”, retrieved online from URL: https://arXiv.org/abs/1301.3781v3 [cs.CL] Sep. 7, 2013 (12 pages).
Murray, K., “A Semantic Scan Statistic for Novel Disease Outbreak Detection”, Master’s Thesis, Carnegie Mellon University, Aug. 16, 2013 (68 pages).
Neelakantan, A., et al., “Efficient Non-parametric Estimation of Multiple Embeddings per Word in Vector Space,” Department of Computer Science, University of Massachusetts, (2015) (11 pages).
Pennington, J. et al., “GloVe: Global Vectors for Word Representation”, retrieved online from URL:<https://nlp.stanford.edu/projects/glove.pdf>, 2014 (12 pages).
Puranik, et al., “Durability analysis of the highly effective BNT162b2 vaccine against COVID-19”, PNAS Nexus, 1:gac082, 2022 (37 pages).
Rajagopalan, H., et al., “Tumorigenesis: RAF/RAS oncogenes and mismatch-repair status”, Nature, 418:934, Aug. 29, 2002 (1 page).
Rajasekharan, “Unsupervised NER using BERT”, [accessed Jun. 10, 2021], Toward Data Science, <URL: https://towardsdatascience.com/unsupervised-ner-using-bert-2d7af5f90b8a>, Feb. 28, 2020 (27 pages).
Seabold, et al., “Statsmodels: Econometric and Statistical Modeling with Python”, Proc. of the 9th Python in Science Conf., pp. 92-96, 2010 (5 pages).
Shamir, A. “How to Share a Secret”, Communications of the ACM, 22(11):612-613, Nov. 1979 (2 pages).
Shweta, Fnu et al., “Augmented Curation of Unstructured Clinical Notes from a Massive EHR System Reveals Specific Phenotypic Signature of Impending COVID-19 Diagnosis”, https://www.medrxiv.org/content/10.1101/2020.04.19.20067660v3.full, accessed Sep. 24, 2020 (24 pages).
Van Mulligen, E.M. et al., “The EU-ADR corpus: Annotated drugs, diseases, targets, and their relationships”, Journal of Biomedical Informatics, 45:879-884, published online Apr. 25, 2012 (6 pages).
Wieting, J. et al., “Revisiting Recurrent Networks for Paraphrastic Sentence Embeddings”, retrieved online from URL:<https://arXiv.org/pdf/1705.00364v1.pdf>, [cs.CL], Apr. 30, 2017 (12 pages).
Yao, Z. et al., “Dynamic Word Embeddings for Evolving Semantic Discovery”, WSDM 2018, Marina Del Rey, CA, USA, Feb. 5-9, 2018 (9 pages).
Zuccon, G., et al., “Integrating and Evaluating Neural Word Embeddings in Information Retrieval”, ADCS, Parramatta, NSW, Australia, Dec. 8-9, 2015 (8 pages).

* cited by examiner

| Output Dataset | Policy |
| --- | --- |
| Does not contain any PII attributes | Unconstrained dataset |
| Contains PII attributes (greater than K records) | Unconstrained dataset |
| Contains PII attributes (less than K records) | Enclose output dataset in container |
| | Encrypt output dataset using FHE |
| | Disallow output request |
| Contains PII data and output request is non-privacy preserving | Enclose output dataset in container |
| | Disallow the request |

Fig. 3

| | Algorithm Provider 1 | Data Provider | Key Fragments | Link to Load Image |
|---|---|---|---|---|
| Group 1 | A1:a1 | D1: d1 | A1(k11), D1(k12) | L1 |
| Group 2 | A2:a2 | D2: d2 | A2(k21), D2(k22) | L2 |
| ... | ... | ... | ... | ... |

Fig. 7

FIG. 19
Cohort A
People administered with Pfizer Vaccine, between Dec 16, 2020 and 266 days after, whose age is in between 0 and 120 years.
All Patients
Cohort B
People administered with Moderna Vaccine, between Dec 16, 2020 and 266 days after, whose age is in between 0 and 120 years.
All Patients
Vaccinated Patient Breakdown
Pfizer
Pfizer
Moderna
Moderna

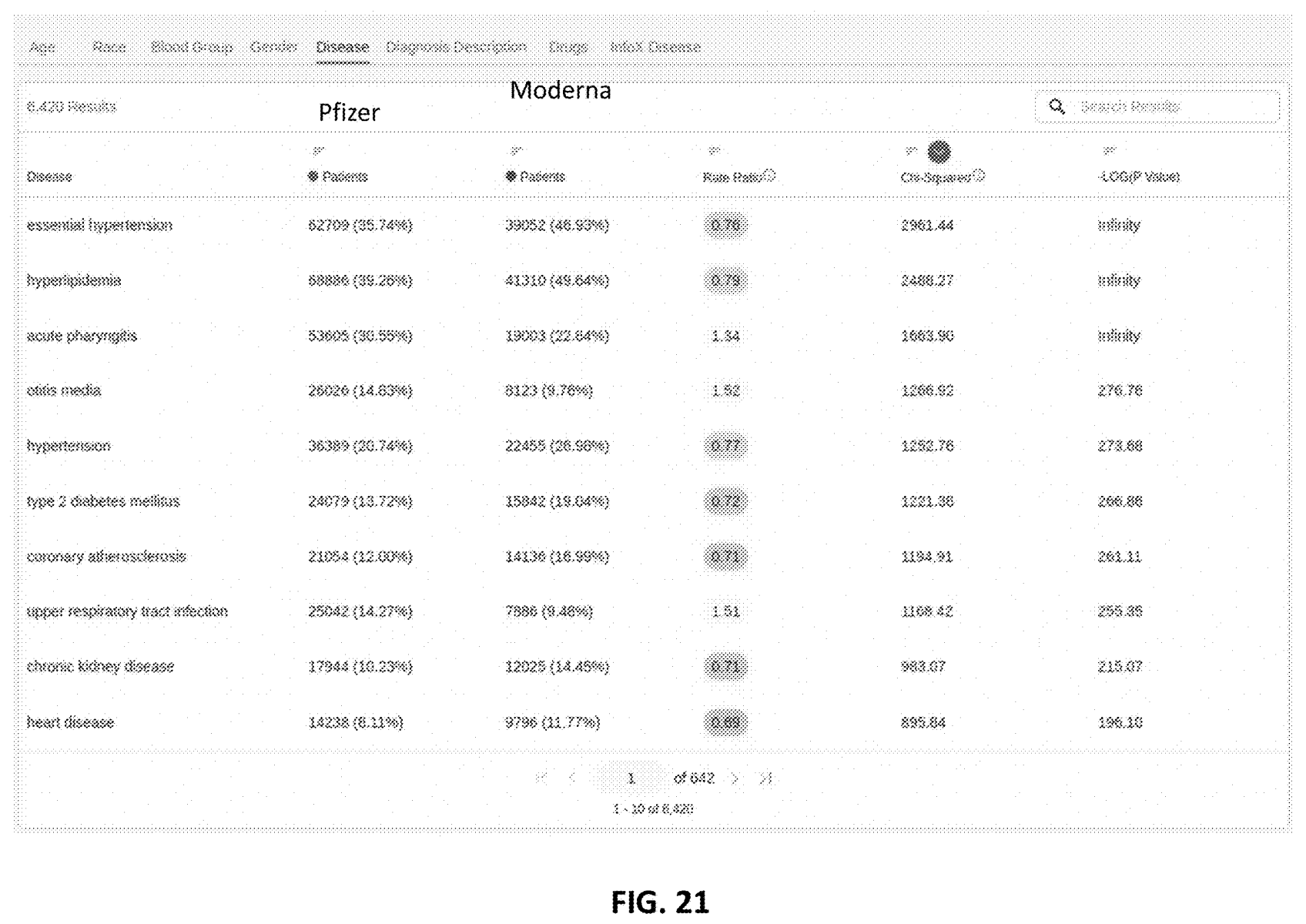

Age Race Blood Group Gender Disease Diagnosis Description Drugs InfoX Disease 6,420 Results Search Results

| Disease | Pfizer Patients | Moderna Patients | Rate Ratio | Chi-Squared | -LOG(P Value) |
|---|---|---|---|---|---|
| essential hypertension | 62709 (35.74%) | 39052 (46.93%) | 0.76 | 2961.44 | infinity |
| hyperlipidemia | 68886 (39.26%) | 41310 (49.64%) | 0.79 | 2488.27 | infinity |
| acute pharyngitis | 53605 (30.55%) | 19003 (22.84%) | 1.34 | 1663.90 | infinity |
| otitis media | 26026 (14.83%) | 8123 (9.76%) | 1.52 | 1266.92 | 276.76 |
| hypertension | 36389 (20.74%) | 22455 (26.98%) | 0.77 | 1252.76 | 273.68 |
| type 2 diabetes mellitus | 24079 (13.72%) | 15842 (19.04%) | 0.72 | 1221.38 | 266.86 |
| coronary atherosclerosis | 21054 (12.00%) | 14136 (16.99%) | 0.71 | 1194.91 | 261.11 |
| upper respiratory tract infection | 25042 (14.27%) | 7886 (9.48%) | 1.51 | 1168.42 | 255.35 |
| chronic kidney disease | 17944 (10.23%) | 12025 (14.45%) | 0.71 | 983.07 | 215.07 |
| heart disease | 14238 (8.11%) | 9796 (11.77%) | 0.69 | 895.84 | 196.10 |

1 of 642

1 - 10 of 6,420

FIG. 21

METHOD OF AND SYSTEM FOR DETECTION OF DURABILITY OF ANTIBODY RESPONSE TO VACCINATION

RELATED APPLICATIONS

This application claims priority to U.S. Provisional Application No. 63/252,778, filed on Oct. 6, 2021, the contents of which is incorporated by reference herein in its entirety.

FIELD OF THE INVENTION

This disclosure relates to systems and methods for a real time sentinel system.

BRIEF SUMMARY OF THE EMBODIMENTS

In one aspect, a method includes constructing an isolated memory partition that forms a secure enclave, wherein the secure enclave is available to one or more processors for running one or more application computing processes in isolation from one or more unauthorized computing processes running on the one or more processors of the secure enclave; pre-provisioning software within the secure enclave, wherein the pre-provisioned software within the secure enclave is configured to execute instructions of the one or more application computing processes on the one or more processors of the secure enclave by: receiving input data for the one or more application computing processes in an encrypted form, wherein the input data includes, for a plurality of individuals, a vaccination date, a test date, and a test result; decrypting the input data using one or more cryptographic keys; executing the one or more application computing processes to generate output data; generating a proof of execution that proves that the one or more instructions of the one or more application computing processes operated on the received input data; and sending the output data to a central node; wherein the central node is pre-provisioned with software configured to execute instructions of the one or more application computing processes on one or more processors of the central node by receiving the output data from a plurality of secure enclaves; executing the one or more application computing processes to apply an aggregate analysis to the output data of each of the plurality of secure enclaves; and providing an aggregate output.

In some embodiments, each of the plurality of secure enclaves is associated with a different health system.

In some embodiments, two or more of the plurality of secure enclaves are associated with two different information systems within a single health system.

In some embodiments, the input data includes at least one of demographic data, comorbidities, and geographic data.

In some embodiments, executing the one or more application computing processes includes fitting a regression model to the input data to generate output data, wherein the output data includes at least one of a regression coefficient of the regression model, a standard error for a regression coefficient, and a value calculated from one or more regression coefficients or one or more standard errors.

In some embodiments, the regression model is a stratified model.

In some embodiments, the regression model is a conditional logistical regression model.

In some embodiments, the output includes the log of an odds ratio at one or more time points and a standard error corresponding to each odds ratio.

In some embodiments, the output includes a plurality regression coefficients of the regression model.

In some embodiments, the output includes a covariance matrix of the coefficients of the regression model.

In some embodiments, the output includes the log of an odds ratio as a continuous function of time.

In some embodiments, the log of the odds ratio as a continuous function of time is estimated based on an interpolation between the log of an odds ratio at two or more time points.

In some embodiments, the pre-provisioned software within the secure enclave is further configured to execute instructions of the one or more application computing processes on the one or more processors of the secure enclave by encrypting the output data using the one or more cryptographic keys; and providing external access to the encrypted output data and the proof of execution.

In some embodiments, the central node is an isolated memory partition available to one or more processors for running one or more application computing processes in isolation from one or more unauthorized computing processes running on the one or more processors of the central node.

In some embodiments, the output data includes a portion of the input data.

In some embodiments, the aggregate analysis includes fitting a regression model to the output data, wherein the output data includes a portion of the input data from each of the plurality of secure enclaves.

In some embodiments, the aggregate analysis includes inverse variance weighting.

In some embodiments, the aggregate analysis includes fitting an aggregate regression model to the output data.

In some embodiments, fitting the regression model and fitting the aggregate regression model is iterative.

In some embodiments, the pre-provisioned with software within the central node is configured to execute instructions of the one or more application computing processes on one or more processors of the central node by sending one or more aggregate regression coefficients of the aggregate regression model to each of the plurality of secure enclaves.

In some embodiments, the pre-provisioned software within the secure enclave is further configured to execute instructions of the one or more application computing processes on the one or more processors of the secure enclave by: receiving one or more aggregate regression coefficients of the aggregate regression model; tuning the regression model using the one or more aggregate regression coefficients of the aggregate regression model to generate updated output data; and sending the updated output data to a central node.

In some embodiments, the updated output includes a gradient of one or more regression coefficients of the regression model.

In some embodiments, the aggregate output includes the log of an odds ratio across the plurality of secure enclaves.

In some embodiments, a vaccination status of an individual is assigned as unvaccinated if the test date is within a predetermined time of the vaccination date and the vaccination status of the individual is assigned as vaccinated if the test date is the predetermined time after the vaccination date.

In some embodiments, the vaccination date includes dates of one or more doses.

In one aspect, system includes a non-transitory memory; and one or more hardware processors configured to read instructions from the non-transitory memory that, when executed cause one or more of the hardware processors to perform operations including: constructing an isolated memory partition that forms a secure enclave, wherein the secure enclave is available to one or more processors for running one or more application computing processes in isolation from one or more unauthorized computing processes running on the one or more processors of the secure enclave; pre-provisioning software within the secure enclave, wherein the pre-provisioned software within the secure enclave is configured to execute instructions of the one or more application computing processes on the one or more processors of the secure enclave by: receiving input data for the one or more application computing processes in an encrypted form, wherein the input data includes, for a plurality of individuals, a vaccination date, a test date, and a test result; decrypting the input data using one or more cryptographic keys; executing the one or more application computing processes to generate output data; generating a proof of execution that proves that the one or more instructions of the one or more application computing processes operated on the received input data; and sending the output data to a central node; wherein the central node is pre-provisioned with software configured to execute instructions of the one or more application computing processes on one or more processors of the central node by receiving the output data from a plurality of secure enclaves; executing the one or more application computing processes to apply an aggregate analysis to the output data of each of the plurality of secure enclaves; and providing an aggregate output.

In some embodiments, executing the one or more application computing processes includes fitting a regression model to the input data to generate output data, wherein the output data includes at least one of a regression coefficient of the regression model, a standard error for a regression coefficient, and a value calculated from one or more regression coefficients or one or more standard errors.

In some embodiments, the output includes the log of an odds ratio at one or more time points and a standard error corresponding to each odds ratio.

In some embodiments, the aggregate analysis includes fitting a regression model to the output data, wherein the output data includes a portion of the input data from each of the plurality of secure enclaves.

In some embodiments, the aggregate analysis includes inverse variance weighting.

In some embodiments, the aggregate analysis includes fitting an aggregate regression model to the output data.

In one aspect, a non-transitory computer-readable medium stores instructions that, when executed by one or more hardware processors, cause the one or more hardware processors to perform operations including: constructing an isolated memory partition that forms a secure enclave, wherein the secure enclave is available to one or more processors for running one or more application computing processes in isolation from one or more unauthorized computing processes running on the one or more processors of the secure enclave; pre-provisioning software within the secure enclave, wherein the pre-provisioned software within the secure enclave is configured to execute instructions of the one or more application computing processes on the one or more processors of the secure enclave by: receiving input data for the one or more application computing processes in an encrypted form, wherein the input data includes, for a plurality of individuals, a vaccination date, a test date, and a test result; decrypting the input data using one or more cryptographic keys; executing the one or more application computing processes to generate output data; generating a proof of execution that proves that the one or more instructions of the one or more application computing processes operated on the received input data; and sending the output data to a central node; wherein the central node is pre-provisioned with software configured to execute instructions of the one or more application computing processes on one or more processors of the central node by receiving the output data from a plurality of secure enclaves; executing the one or more application computing processes to apply an aggregate analysis to the output data of each of the plurality of secure enclaves; and providing an aggregate output.

In some embodiments, executing the one or more application computing processes includes fitting a regression model to the input data to generate output data, wherein the output data includes at least one of a regression coefficient of the regression model, a standard error for a regression coefficient, and a value calculated from one or more regression coefficients or one or more standard errors.

In some embodiments, the output includes the log of an odds ratio at one or more time points and a standard error corresponding to each odds ratio.

In some embodiments, the aggregate analysis includes fitting a regression model to the output data, wherein the output data includes a portion of the input data from each of the plurality of secure enclaves.

In some embodiments, the aggregate analysis includes inverse variance weighting.

In some embodiments, the aggregate analysis includes fitting an aggregate regression model to the output data.

In one aspect, a method includes constructing a central node; wherein the central node is in communication with a plurality of secure enclaves, wherein each of the plurality of secure enclaves is formed by an isolated memory partition and is available to one or more processors for running one or more computing processes in isolation from one or more unauthorized computing processes running on the one or more processors of each of the plurality of secure enclaves; pre-provisioning software within the central node, wherein the pre-provisioned software is configured to execute instructions of the one or more application computing processes on the one or more processors of the central node by receiving output data from the plurality of secure enclaves; executing the one or more application computing processes to apply an aggregate analysis to the output data of each of the plurality of secure enclaves; and providing an aggregate output; wherein each of the plurality of secure enclaves is pre-provisioned with software configured to execute instructions of the one or more application computing processes on the one or more processors of each of the plurality of secure enclaves by: receiving input data for the one or more application computing processes in an encrypted form, wherein the input data includes, for a plurality of individuals, a vaccination date, a test date, and a test result; decrypting the input data using one or more cryptographic keys; executing the one or more application computing processes to generate the output data; generating a proof of execution that proves that the one or more instructions of the one or more application computing processes operated on the received input data; and sending the output data to the central node.

In some embodiments, each of the plurality of secure enclaves are associated with a different health system.

In some embodiments, two or more of the plurality of secure enclaves are associated with two different information systems within a single health system.

In some embodiments, the input data includes at least one of demographic data, comorbidities, and geographic data.

In some embodiments, executing the one or more application computing processes includes fitting a regression model to the input data to generate output data, wherein the output data includes at least one of a regression coefficient of the regression model, a standard error for a regression coefficient, and a value calculated from one or more regression coefficients or one or more standard errors.

In some embodiments, the regression model is a stratified model.

In some embodiments, the regression model is a conditional logistical regression model.

In some embodiments, the output includes the log of an odds ratio at one or more time points and a standard error corresponding to each odds ratio.

In some embodiments, the output includes a plurality regression coefficients of the regression model.

In some embodiments, the output includes a covariance matrix of the coefficients of the regression model.

In some embodiments, the output includes the log of an odds ratio as a continuous function of time.

In some embodiments, the log of the odds ratio as a continuous function of time is estimated based on an interpolation between the log of an odds ratio at two or more time points.

In some embodiments, the pre-provisioned software within each of the plurality of secure enclaves is further configured to execute instructions of the one or more application computing processes on the one or more processors of the secure enclave by encrypting the output data using the one or more cryptographic keys; and providing external access to the encrypted output data and the proof of execution.

In some embodiments, the central node is an isolated memory partition available to one or more processors for running one or more application computing processes in isolation from one or more unauthorized computing processes running on the one or more processors of the central node.

In some embodiments, the output data includes a portion of the input data.

In some embodiments, the aggregate analysis includes fitting a regression model to the output data, wherein the output data includes a portion of the input data from each of the plurality of secure enclaves.

In some embodiments, the aggregate analysis includes inverse variance weighting.

In some embodiments, the aggregate analysis includes fitting an aggregate regression model to the output data.

In some embodiments, fitting the regression model and fitting the aggregate regression model is iterative.

In some embodiments, the pre-provisioned with software within the central node is configured to execute instructions of the one or more application computing processes on one or more processors of the central node by sending one or more aggregate regression coefficients of the aggregate regression model to each of the plurality of secure enclaves.

In some embodiments, the pre-provisioned software within each of the plurality of secure enclaves is further configured to execute instructions of the one or more application computing processes on the one or more processors of the secure enclave by: receiving one or more aggregate regression coefficients of the aggregate regression model; tuning the regression model using the one or more aggregate regression coefficients of the aggregate regression model to generate updated output data; and sending the updated output data to a central node.

In some embodiments, the updated output includes a gradient of one or more regression coefficients of the regression model.

In some embodiments, the aggregate output includes the log of an odds ratio across the plurality of secure enclaves.

In some embodiments, a vaccination status of an individual is assigned as unvaccinated if the test date is within a predetermined time of the vaccination date and the vaccination status of the individual is assigned as vaccinated if the test date is the predetermined time after the vaccination date.

In some embodiments, the vaccination date includes dates of one or more doses.

In one aspect, a includes a non-transitory memory; and one or more hardware processors configured to read instructions from the non-transitory memory that, when executed cause one or more of the hardware processors to perform operations including: constructing a central node; wherein the central node is in communication with a plurality of secure enclaves, wherein each secure enclave is formed by an isolated memory partition and is available to one or more processors for running one or more computing processes in isolation from one or more unauthorized computing processes running on the one or more processors of each secure enclave; pre-provisioning software within the central node, wherein the pre-provisioned software is configured to execute instructions of the one or more application computing processes on the one or more processors of the central node by receiving output data from a plurality of secure enclaves; executing the one or more application computing processes to apply an aggregate analysis to the output data of each of the plurality of secure enclaves; and providing an aggregate output; wherein each of the plurality of secure enclaves is pre-provisioned with software configured to execute instructions of the one or more application computing processes on the one or more processors of each of the plurality of secure enclaves by: receiving input data for the one or more application computing processes in an encrypted form, wherein the input data includes, for a plurality of individuals, a vaccination status, a vaccination date, a test date, and a test result; decrypting the input data using one or more cryptographic keys; executing the one or more application computing processes to generate the output data; generating a proof of execution that proves that the one or more instructions of the one or more application computing processes operated on the received input data; and sending the output data to the central node.

In some embodiments, executing the one or more application computing processes includes fitting a regression model to the input data to generate output data, wherein the output data includes at least one of a regression coefficient of the regression model, a standard error for a regression coefficient, and a value calculated from one or more regression coefficients or one or more standard errors.

In some embodiments, the output includes the log of an odds ratio at one or more time points and a standard error corresponding to each odds ratio.

In some embodiments, the aggregate analysis includes fitting a regression model to the output data, wherein the output data includes a portion of the input data from each of the plurality of secure enclaves.

In some embodiments, the aggregate analysis includes inverse variance weighting.

In some embodiments, the aggregate analysis includes fitting an aggregate regression model to the output data.

In one aspect, a non-transitory computer-readable medium stores instructions that, when executed by one or more hardware processors, cause the one or more hardware processors to perform operations including: constructing a central node; wherein the central node is in communication with a plurality of secure enclaves, wherein each secure enclave is formed by an isolated memory partition and is available to one or more processors for running one or more computing processes in isolation from one or more unauthorized computing processes running on the one or more processors of each of the plurality of secure enclaves; pre-provisioning software within the central node, wherein the pre-provisioned software is configured to execute instructions of the one or more application computing processes on the one or more processors of the central node by receiving output data from a plurality of secure enclaves; executing the one or more application computing processes to apply an aggregate analysis to the output data of each of the plurality of secure enclaves; and providing an aggregate output; wherein each of the plurality of secure enclaves is pre-provisioned with software configured to execute instructions of the one or more application computing processes on the one or more processors of each of the plurality of secure enclaves by: receiving input data for the one or more application computing processes in an encrypted form, wherein the input data includes, for a plurality of individuals, a vaccination status, a vaccination date, a test date, and a test result; decrypting the input data using one or more cryptographic keys; executing the one or more application computing processes to generate the output data; generating a proof of execution that proves that the one or more instructions of the one or more application computing processes operated on the received input data; and sending the output data to the central node.

In some embodiments, executing the one or more application computing processes includes fitting a regression model to the input data to generate output data, wherein the output data includes at least one of a regression coefficient of the regression model, a standard error for a regression coefficient, and a value calculated from one or more regression coefficients or one or more standard errors.

In some embodiments, the output includes the log of an odds ratio at one or more time points and a standard error corresponding to each odds ratio.

In some embodiments, the aggregate analysis includes fitting a regression model to the output data, wherein the output data includes a portion of the input data from each of the plurality of secure enclaves.

In some embodiments, the aggregate analysis includes inverse variance weighting.

In some embodiments, the aggregate analysis includes fitting an aggregate regression model to the output data.

Any one of the embodiments disclosed herein may be properly combined with any other embodiment disclosed herein. The combination of any one of the embodiments disclosed herein with any other embodiments disclosed herein is expressly contemplated.

BRIEF DESCRIPTION OF THE DRAWINGS

The objects and advantages will be apparent upon consideration of the following detailed description, taken in conjunction with the accompanying drawings, in which like reference characters refer to like parts throughout, and in which

FIG. 3 is a simplified diagram of illustrative policies applicable to datasets according to certain embodiments.

FIG. 7 is a simplified diagram of a decentralized trust model according to some embodiments, according to certain embodiments.

FIG. 21 shows co-morbidities in the Moderna and Pfizer cohorts, showing that the Moderna cohort is sicker than the Pfizer cohort, according to certain embodiments.

DETAILED DESCRIPTION

A real time 'sentinel' system is disclosed that can alert policymakers, health care provider systems and other decision makers when the efficacy of vaccines (e.g., COVID19 vaccines) is going to go down. To make a determination of durability of a vaccine, real world data from Health Systems is used to allows comparison of two cohorts: a vaccinated one with an unvaccinated one. If the risk of contracting the virus (Risk Ratio or odds ratio) of a person who took the vaccine approaches the risk of an unvaccinated person, one can conclude that the vaccine is losing its effectiveness (or durability).

Figure 11:
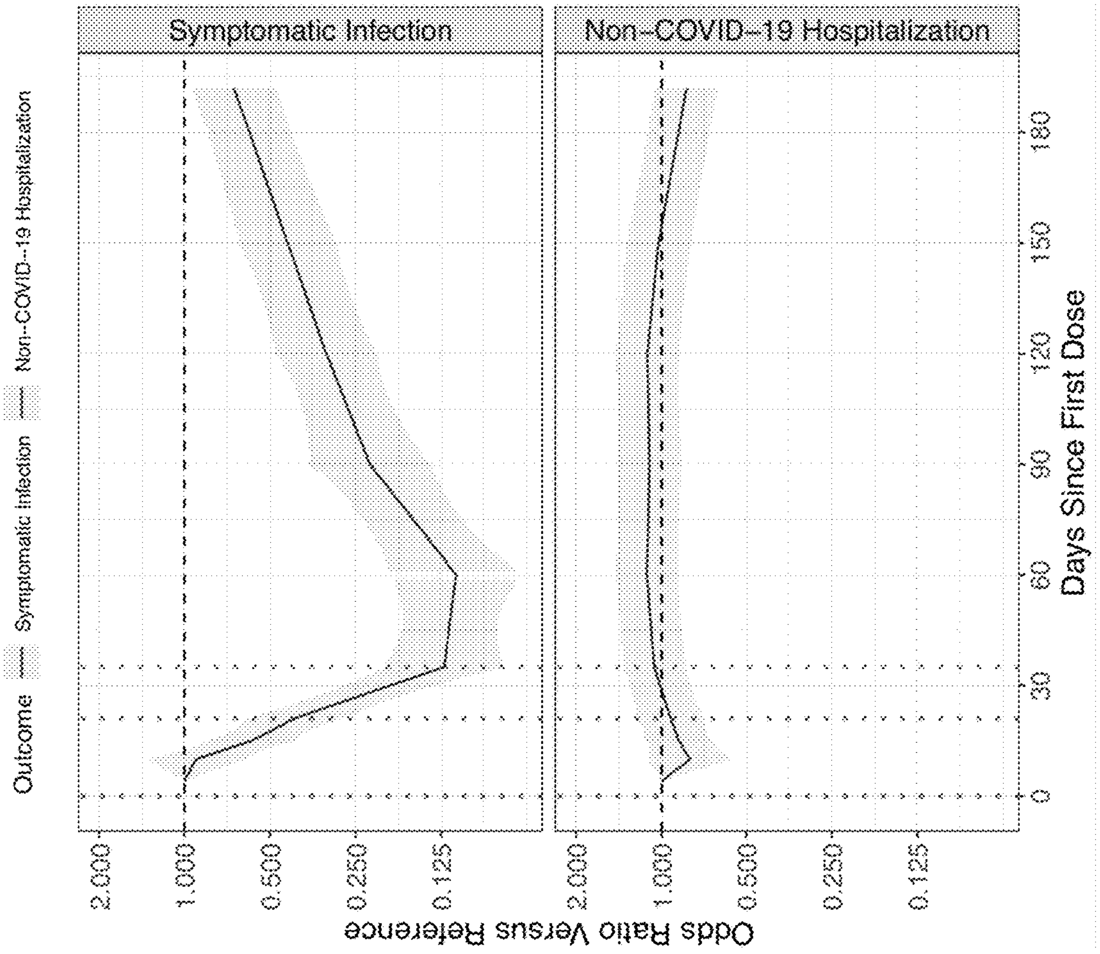
FIG. 11 shows the Odds Ratio of as a function of days since full vaccination for symptomatic infection and non-COVID-19 hospitalization, according to certain embodiments.

For example, a small amount of data from one health system leads to a conclusion that the vaccines are losing their durability after several (6-8) months. See FIG. 11, which shows the odds ratio of symptomatic infection (top) and non-COVID-19 hospitalization (bottom) for vaccinated individuals. The line in the top graph shows how the Risk Ratio varies with 'days since the first dose of vaccination.' This curve has an inherent uncertainty which is quantified by providing the 95% Confidence Interval (shown as the lighter band). As shown in FIG. 11, the vaccine (e.g., Pfizer's vaccine) has the best result 60 days after the first dose based on a small cohort of patients. That is, the rate of vaccinated patients getting a breakthrough infection are at its lowest compared to unvaccinated patients. As time passes, the rate of breakthrough infection is increasing almost reaching 0.25 in 180 days.

If there is a greater number of patients in these cohorts, the 'uncertainty band' will be tighter as a consequence of statistics. Accordingly, it would be desirable to develop improved methods to increase the number of patients in cohorts, e.g., by aggregating data across health systems. For example, in some embodiments, the software for a sentinel system runs in the 'control' of a Health System so that patient privacy is not compromised (e.g., using privacy preserving architecture). In some embodiments, multiple health systems, e.g., in every state of the country, use a 'federated architecture' so that patient data is processed within secure enclaves (e.g., within each health system) and is not copied to a single central place before the software or a central coordinator computes risk ratios or other aggregate output relating to vaccine durability. Further description of federated architecture can be found below and in U.S. patent application Ser. No. 16/908,520, titled "Systems and Method for Computing with Private Healthcare data," filed Jun. 22, 2020, the contents of which are incorporated by reference in its entirety.

A truly astonishing amount of information has been collected from patients and consumers pertaining to their health status, habits, environment, surroundings, and homes. Increasingly, this information is being processed by computer programs utilizing machine learning and artificial intelligence models. Such computer programs have shown remarkable progress in analyzing and predicting consumer health status, incidence and treatment of diseases, user behavior, etc. Furthermore, since the collected data may contain patient biometric and other personal identification attributes, there is a growing concern that such computer programs may allow the identities of patients and consumers to be learned. Accordingly, enterprises interested in analyzing healthcare data containing private attributes are concerned with maintaining privacy of individuals and observing the relevant regulations pertaining to private and personal data, such as HIPAA (Health Insurance Portability and Accountability Act 1996) regulations.

In addition to HIPAA, many other regulations have been enacted in various jurisdictions, such as GDPR (General Data Protection Regulations) in the European Union, PSD2 (Revised Payment Services Directive), CCPA (California Consumer Privacy Act 2018), etc.

In the following descriptions, the terms "user information," personal information," "personal health information ("PHI")," "healthcare information data or records," "identifying information," and PII (Personally Identifiable Information) may be used interchangeably. Likewise, the terms "electronic health records ("EHR")" and "data records" may be used interchangeably.

One approach to handling private data is to encrypt all the records of a dataset. Encrypted text is sometimes referred to as ciphertext; decrypted text is also referred to as plaintext. Encryption may be described, by way of analogy, as putting the records of the dataset in a locked box. Access to the records of the locked box is then controlled by the key to the locked box. The idea is that only authorized entities are allowed access to the (decryption) key.

Some regulations (e.g., HIPAA) require that healthcare data be stored in encrypted form. This is also sometimes referred to as "encryption at rest."

Malicious entities may, however, gain access to the decryption key or infer/guess the decryption key using computational mechanisms. The latter possibility becomes probable when the encryption/decryption technologies are not sufficiently strong (e.g., the length of the key—the number of bits comprising the key—is not sufficiently long to withstand computational attacks), or if the key is lost or not stored securely.

Encryption and other such security technologies may depend on the expectation that a computational attacker is likely to expend a certain amount of resources—computer time, memory and computing power—to gain access to the underlying data. The length of encryption keys is one of the variables used to increase the amount of computational resources needed to break the encryption.

Even strong encryption technology may not resolve security challenges associated with processing private data. For example, an enterprise that is processing an encrypted dataset may load the dataset into a computer, decrypt the dataset, process the records of the dataset and re-encrypt the dataset. In this example, one or more records of the dataset are decrypted (into plaintext) during processing. A malicious entity may gain access to the computer while the plaintext records are being processed, leading to a leak of personal information. That is, decrypting the data for the purpose of processing introduces a "run-time" vulnerability.

Accordingly, it would be desirable to develop improved techniques for processing private data.

Fully homomorphic encryption (FHE) describes an approach for computing with encrypted data without decrypting it. That is, given encrypted data elements $$x_1^e, x_2^e, \ldots$$

compute the function $$f(x_1^e, x_2^e, \ldots)$$

yielding an encrypted result $$(y_1^e, y_2^e, \ldots).$$

Since the input, output and processing phases of such computations deal with encrypted data elements only, the probability of leaks is minimized. If the (mathematical) basis of the encryption technology is sufficiently strong, the inference/guessing of keys may become an infeasible computation, even if very powerful computers, e.g., quantum computers, are used.

However, conventional techniques for computing with FHE datasets may be inefficient to the point of being impractical. Calculations reported in 2009 put computations running over FHE datasets as hundred trillion times slower than unencrypted data computations. (See Ameesh Divatia, https://www.darkreading.com/attacks-breaches/the-fact-and-fiction-of-homomorphic-encryption/a/d-id/1333691 and Priyadarshan Kolte, https://baffle.io/blog/why-is-homomorphic-encryption-not-ready-for-primetime/.)

Furthermore, existing application code may need to be re-written to use FHE libraries that provide the basic FHE functions.

A secure enclave describes a computing environment where sensitive data can be decrypted and processed in memory without exposing it to the other processes running in the computer. Data is decrypted and processed in a computing environment that is "isolated" from other processes and networks. Protection of such an environment could be further enhanced by protecting the decryption keys in a manner explained later.

The technology of secure enclaves may be more efficient than FHE techniques.

In some instances, a computer containing a secure enclave may also be referred to as a secure computer. A secure computer may contain one or more secure enclaves, e.g., one secure enclave for each application running in the computer.

In general, it is a goal of secure enclave technology to ensure isolation of the enclave from other processes and from other enclaves.

A secure enclave is an isolated environment including hardware (CPU, memory, registers, cache, etc.) and/or software (programmed circuitry). The secure enclave is accessible by application programs via especially configured hardware and software elements, sometimes referred to as a call gate or a firewall. Access to the secure enclave may be controlled via cryptographic keys some of which may reside in hardware elements, configured at the time of manufacturing. A malicious entity could attempt to extract keys during the booting process of the secure enclave. Reverse engineering or other such attacks to extract keys may be thwarted by disallowing repeated key requests and/or lengthening the time between such requests. In some cases, a set of keys may be associated with a particular set of hardware elements.

Additional protection may be achieved by requiring that data (and computer programs) that are injected into a secure enclave be encrypted; further that data outputted from a secure enclave to be encrypted also. Encrypted data once injected into a secure enclave could then be decrypted within the secure enclave, processed, and the results could be encrypted in preparation for output. Thus, an isolated secure enclave solves the runtime vulnerability problem discussed above.

Additional measures of protecting the data within a secure enclave can be introduced by requiring that the process of decrypting the data inside the secure enclave be made more secure by protecting the decryption keys from being known outside the secure enclave. That is, entities external to the secure enclave infrastructure are prohibited from accessing the decryption key In this manner, encrypted data may be injected into a secure enclave when an injecting agent satisfies the constraints of the firewall of the secure enclave. The secure enclave includes a decryption key that may be used to decrypt the injected data and process it. The secure enclave may encrypt results of the processing activity using an encryption key available inside the secure enclave before outputting the results.

Another technique to address the issue of protecting private data is to de-identify or anonymize the data. This technique relies on replacing private data by random data, e.g., replacing social security numbers by random digits. Such techniques may be used in structured datasets. For example, a structured dataset comprising names, social security number and heart rate of patients may be anonymized by de-identifying the values of the attributes "name" and "social security number."

De-identification technologies in structured datasets lead to loss of processing power as follows.

Structured datasets often need to be combined with other structured datasets to gain maximum processing advantage. Consider, by way of example, two structured datasets (name, SS#, heartrate) and (name, SS#, weight). By combining the two datasets, one may gain a more complete data record of a patient. That is, one may exploit the relationships inherent in the two datasets by associating the patients represented in the two datasets. The process of de-identifying the two datasets leads to anonymizing the patients which loses the inherent relationships.

To continue with the above example, in order to preserve the inherent relationship, the entity performing the de-identification may assign the same random data to the represented patients in the two datasets. That is, the anonymizing entity knows that a patient, say John, is represented by certain data in the two datasets. This implies that the knowledge of the entity doing the anonymizing becomes a vulnerability.

Thus, de-identifying structured data may lead to introducing vulnerabilities that may be exploited by malicious computational entities.

Another disadvantage of traditional de-identifying technologies is that it does not apply to unstructured datasets such as medical notes, annotations, medical history, pathology data, etc. A large amount of healthcare data consists of unstructured datasets. In a later part of this disclosure, techniques that use machine learning and artificial intelligence techniques to de-identify unstructured datasets are disclosed.

One consequence of de-identifying unstructured datasets is that the resulting dataset may contain some residual private data. In one embodiment, de-identification of an unstructured dataset is subjected to a statistical analysis that derives a measure of the effectiveness of the de-identification. That is, measures of the probability to which a dataset has been de-identified may be obtained.

In embodiments, an entity A de-identifies a dataset to a probability measure p, and provides it to an entity B. The latter also receives from an entity C one or more computer programs. Entity B processes the data received from entity A using the computer programs received from entity C and provides the result of the processing to another entity D. (In embodiments, A, B, C and D may be distinct entities in principle; in practice, one or more of entities A, B, C and D may be cooperate through mutual agreements.)

Embodiments of the present invention enable Entity B to assure entity A (and C, and D) that its processing maintains the probability p associated with the data.

Further, in a process not involving entity B, entity A may approve the use of computer programs of entity C on its dataset.

Embodiments of the present invention enable entity B to assure entity C (and A, and D) that the dataset in question was only processed by computer programs provided by entity C and that the dataset was not processed by any other computer program. Furthermore, entity B may be able to assure the other entities that the computer programs provided by entity C and used to process the underlying dataset were not altered, changed or modified in any manner, i.e., the binary image of the computer programs used during processing was identical to the binary image of the provided computer programs. That is, this enablement maintains the provenance of the received computer programs.

Furthermore, the inscrutability property corresponds to a property that satisfies the following conditions.

1. Entity B can assure entities A, C and D that it did not have access to the dataset provided by entity A, to the computer programs provided by entity C, and to the outputs provided to entity D.
2. Entity B can assure entities C and D that entity A only had access to dataset A and did not have access to either the computer programs provided by C or to the outputs provided to entity D.
3. Entity B can assure entities A and D that entity C only had access to its computer programs and did not have access either to the dataset provided by A or the outputs provided to D.
4. Entity B can assure entities C and D that entity A only had access to the dataset A that it provided and did not have access either to the outputs provided to D or to the computer programs provided by C.

Additionally, the various assurances above are provided in the form of verifiable and unforgeable data instruments, i.e., certificates, based on the technology of cryptography.

Figure 1A:
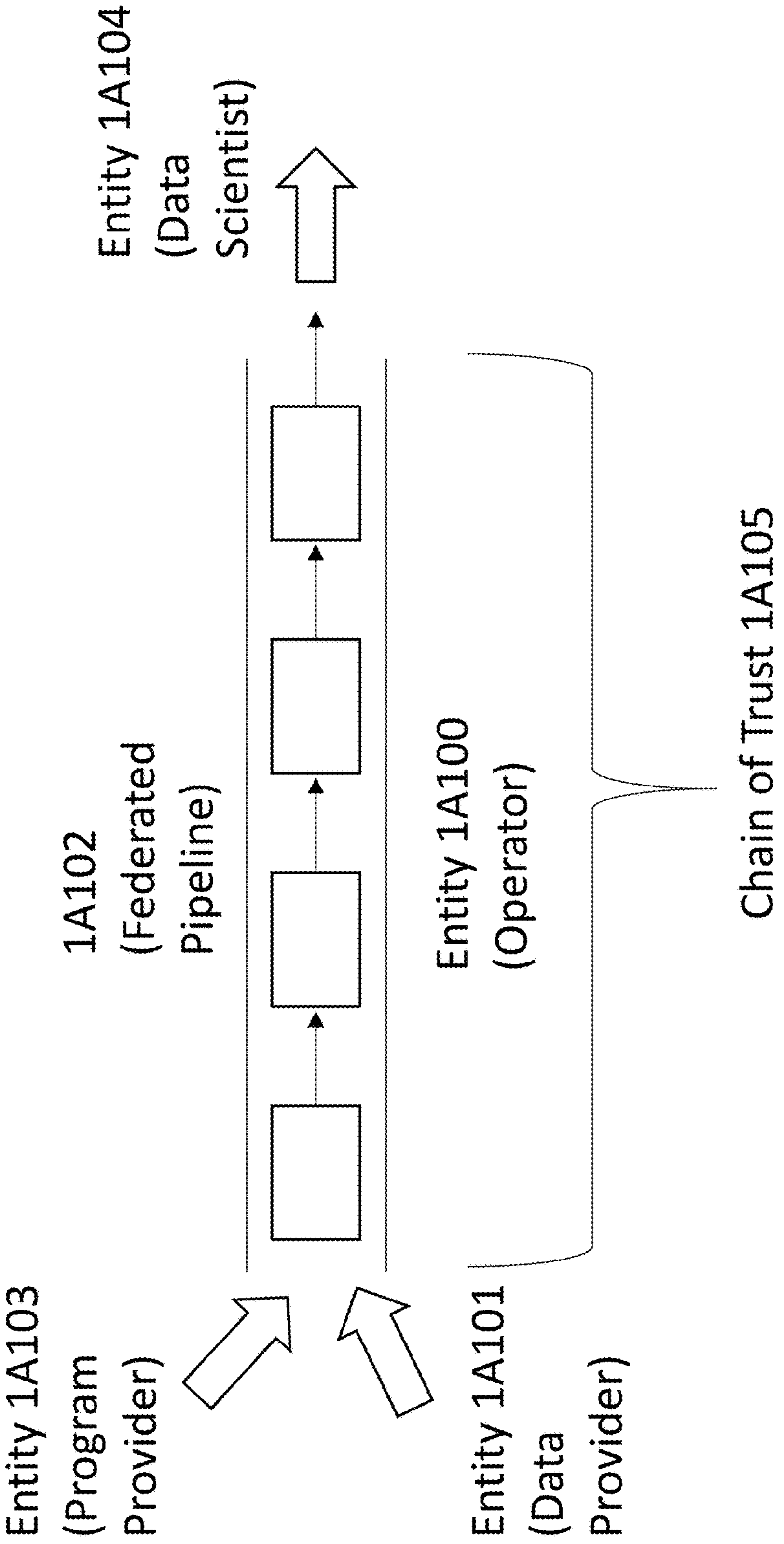
FIG. 1A is a diagram showing a federated approach to processing datasets containing private data, according to certain embodiments.

Embodiments of the present invention, shown in FIG. 1A, enable a first entity 1A100 to construct a "computational chain of trust" 1A105 originating at a point where it receives a dataset (with a pre-determined de-identified probability) from a second entity 1A101, extending through one or more data processing stages 1A102 using computer programs received from a third entity 1A103, and terminating at a point where the results of the processing are received by the fourth entity 1A104. Furthermore, the chain of trust 1A105 satisfies the inscrutability property. Thus, the chain of trust embodies the notions of preserving the input probability measure, the provenance of the received computer programs and the inscrutability property.

Without loss of generality and for ease of description, in the illustrative embodiment of FIG. 1A, the first entity A is labeled "operator," the second entity is labeled "data provider," the third entity is labeled "program provider," and the fourth entity is labeled "data scientist." The equipment performing the processing is labeled "federated pipeline." The term "federated" indicates that the pipeline may receive inputs from multiple entities and may provide outputs to multiple entities.

The present disclosure, inter alia, describes "federated pipelines" (implemented using software technologies and/or hardware/firmware components) that maintain the input de-identification probability of datasets, the provenance of input computer programs, and the inscrutability of the various data and computer programs involved in the computation.

In some cases, a data scientist (e.g., entity 1A104 cf. FIG. 1A), having obtained an output dataset or result from a federated pipeline, may wish to process the output dataset and share the result with a third party. Note that since the data scientist receives the output from a federated pipeline, as explained above, the output is associated with a (series of) attestations, i.e., a chain of trust. If the data scientist now wishes to process the received output and share it with a third party, the latter may ask that the chain of trust be extended to the newly processed result(s).

That is, the third party may wish to obtain a proof that the output received from the federated pipeline was indeed used as input to a new computer program and the output provided to the third-party is outputted by the said program. That is, the data scientist may be asked by the third-party to extend the chain of trust associated with the federated pipeline. If the data scientist is not associated with the federated pipeline, a method of extending the chain of trust is needed that is independent of the method(s) used in the federated pipeline system.

Figure 5:
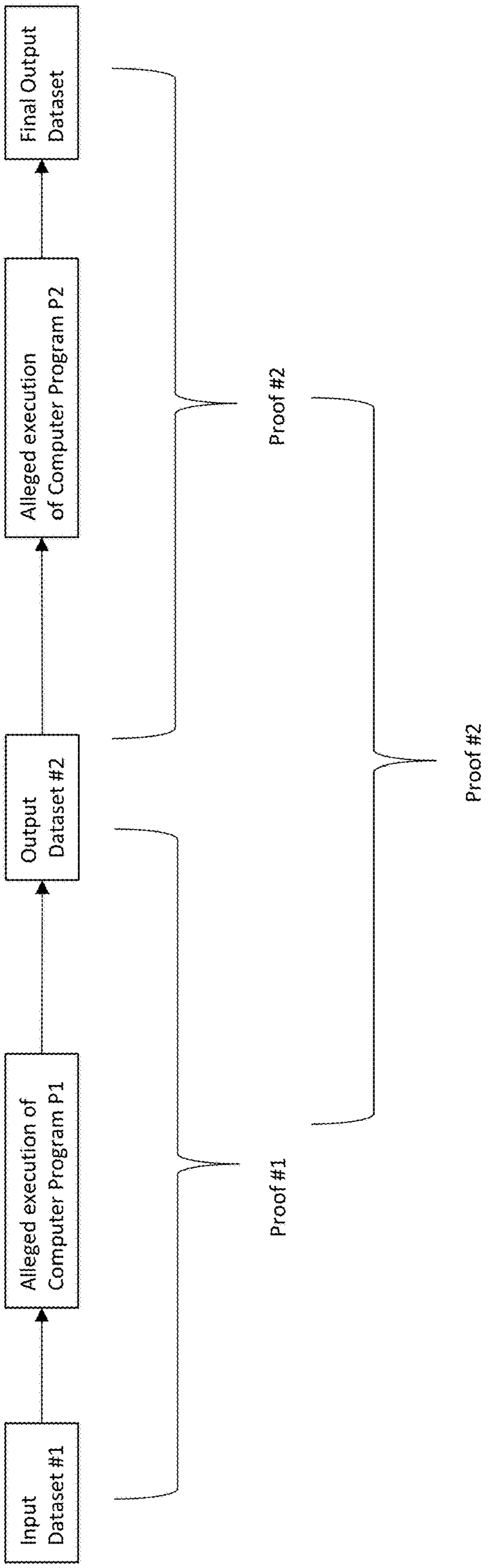
FIG. 5 is a simplified diagram of the use of technology to extend the chain of trust, i.e., the attestation or proofs associated with the federated pipeline of computations, according to certain embodiments.

FIG. 5 illustrates this challenge. The data scientist, when sharing a result, wishes the recipient of the result to trust that a certain computer program (P1) that possibly may have been provided by the data scientist, was executed and that it accepted and verified the source of an input dataset (#1) provided by a federated pipeline with an attestation. Program P1, for example, may check a serial number provided as a part of dataset #1 against a known external data repository. The alleged execution of program P1 results in dataset#2.

Furthermore, the data scientist may wish that the recipient trust that dataset #2 was processed by a computer program P2 (that may have been provided by the data scientist) and the alleged execution of program P2 resulted in the Final Output Dataset (FIG. 5).

D. Genkin, et. al. "Privacy in Decentralized Cryptocurrencies," C. of the ACM, 2018, incorporated herein by reference in its entirety, illustrates exemplary techniques for verifying the execution of programs P1 and P2. A software module called the prover provides a computing environment in which the program P1 and P2 may be executed. Upon such executions, the prover produces two outputs: (1) the output of the programs P1 and P2, and (2) a data object called the proof of the execution of programs P1 and/or P2.

Figure 6:
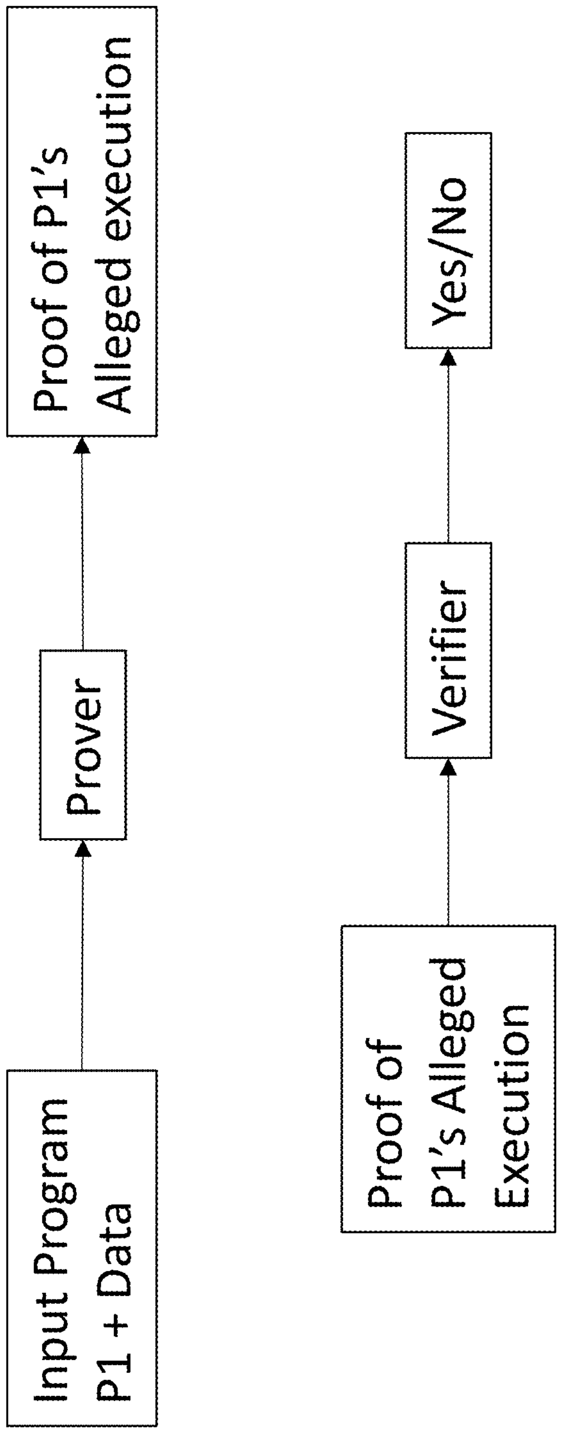
FIG. 6 is a simplified diagram of the verification of the extended chain of trust, according to certain embodiments.

Additionally, the prover also provides a software module called the verifier (cf. FIG. 6) which may be provided to any third-party. The verifier takes a proof as input and outputs a binary "yes/no" answer. An answer "yes" signifies that the program under question was executed and produced the input proof object. A response "No" signifies that the proof of the alleged execution could not be verified.

Thus, D. Genkin, et. al. shows system and methods whereby alleged execution of computer programs may be verified by submitting the proofs of the alleged executions to a verifier system. The proof objects are cryptographic objects and do not leak information about the underlying data or the programs (other than the meta statement that the alleged execution is verifiable).

In embodiments, a computer program, P, may be agreed upon as incorporating a policy between two enterprises, $E_1$ and $E_2$. The former enterprise $E_1$ may now cause the program P to be executed and to produce a proof $\pi$ of its alleged execution using the above described prover technology. Enterprise $E_2$ may now verify $\pi$ (using the verifying technology described above) and trust that the program P was executed, thereby trusting that the agreed upon policy has been implemented.

Figure 1B:
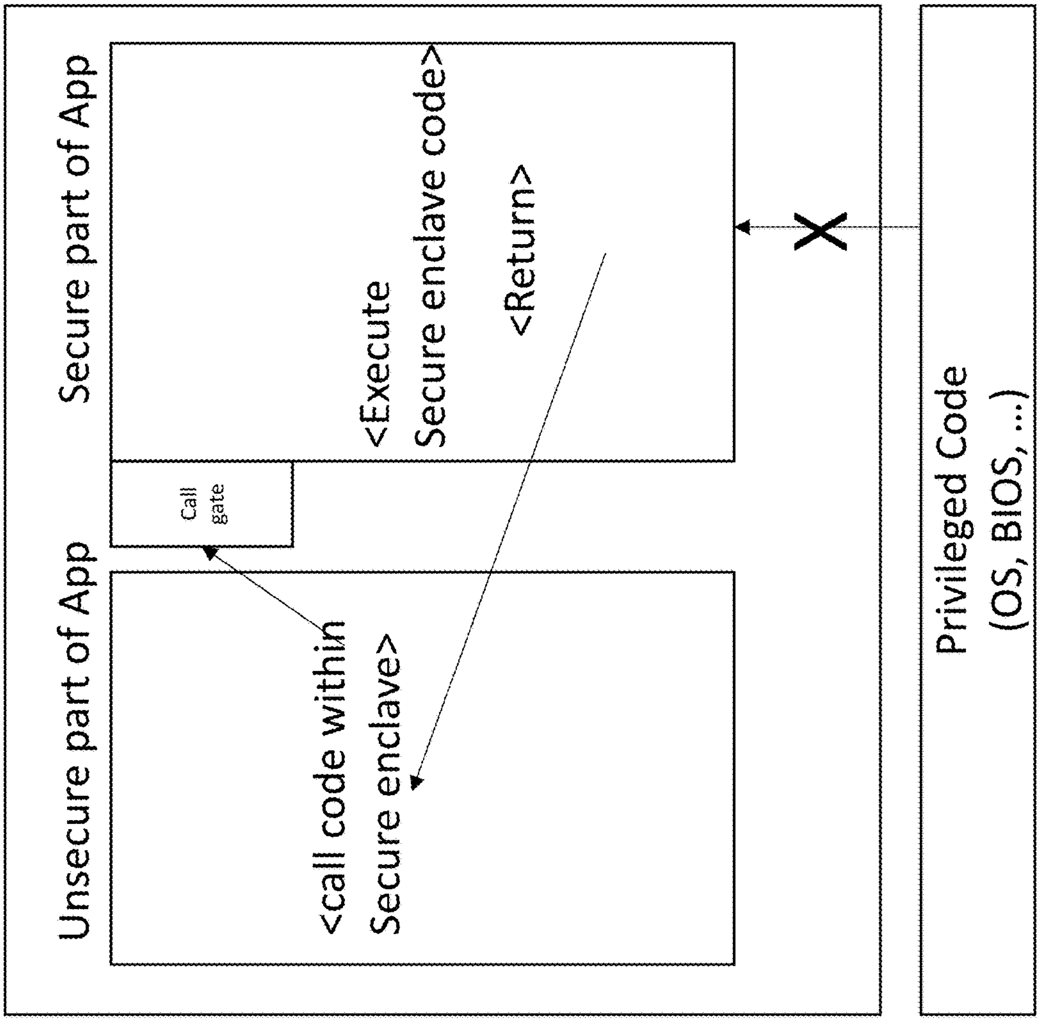
FIG. 1B is a simplified diagram of an architecture of a secure computing environment according to certain embodiments.

FIG. 1B shows a logical architecture of a secure enclave from an application point of view. An application 100 contains its own code, data and secure enclave. Application 100 is logically split into two parts: (1) an unsecure part that runs as a typical application in a traditional computer, and (2) a secure part that runs in the secure enclave. The code in the unsecure part of the application can request that a secure enclave be created, a certain boot image be loaded into the secure enclave and executed. Control at the end of execution in the secure enclave is then returned back to the point of invocation. The privileged system 200 (comprising OS, BIOS, SMM, VM, etc.) is prevented from accessing the secure enclave.

In some embodiments, the following method may be performed to populate a secure enclave with code and data.

Method [Create and populate Secure Enclave]

(1) compile secure part of application;

(2) issue command to create secure enclave (e.g., using underlying hardware/OS instruction set);

(3) Load any pre-provisioned code from pre-specified libraries;

(4) load the compiled code from step 1 into secure enclave;

(5) generate appropriate credentials; and (6) save the image of the secure enclave and the credentials.

In some embodiments, the following method may be performed to execute the code in a secure enclave.

Method[Execute Code in Secure Enclave]

(1) compile unsecure part of an application (e.g., application 100) along with the secure image;

(2) execute the application;

(3) the application creates the secure enclave and loads the image in the secure enclave; and (4) verify the various credentials.

The hardware and software components of a secure enclave provide data privacy by protecting the integrity and confidentiality of the code and data in the enclave. The entry and exit points are pre-defined at the time of compiling the application code. A secure enclave may send/receive encrypted data form its application and it can save encrypted data to disk. An enclave can access its application's memory, but the reverse is not true, i.e., the application cannot access an enclave's memory.

An enclave is a self-sufficient executable software that can be run on designated computers. For example, the enclave may include the resources (e.g., code libraries) that it uses during operation, rather than invoking external or shared resources. In some cases, hardware (e.g., a graphic processing unit or certain amount of memory) and operating system (e.g., Linux version 2.7 or Alpine Linux version 3.2) requirements may be specified for an enclave.

Figure 2:
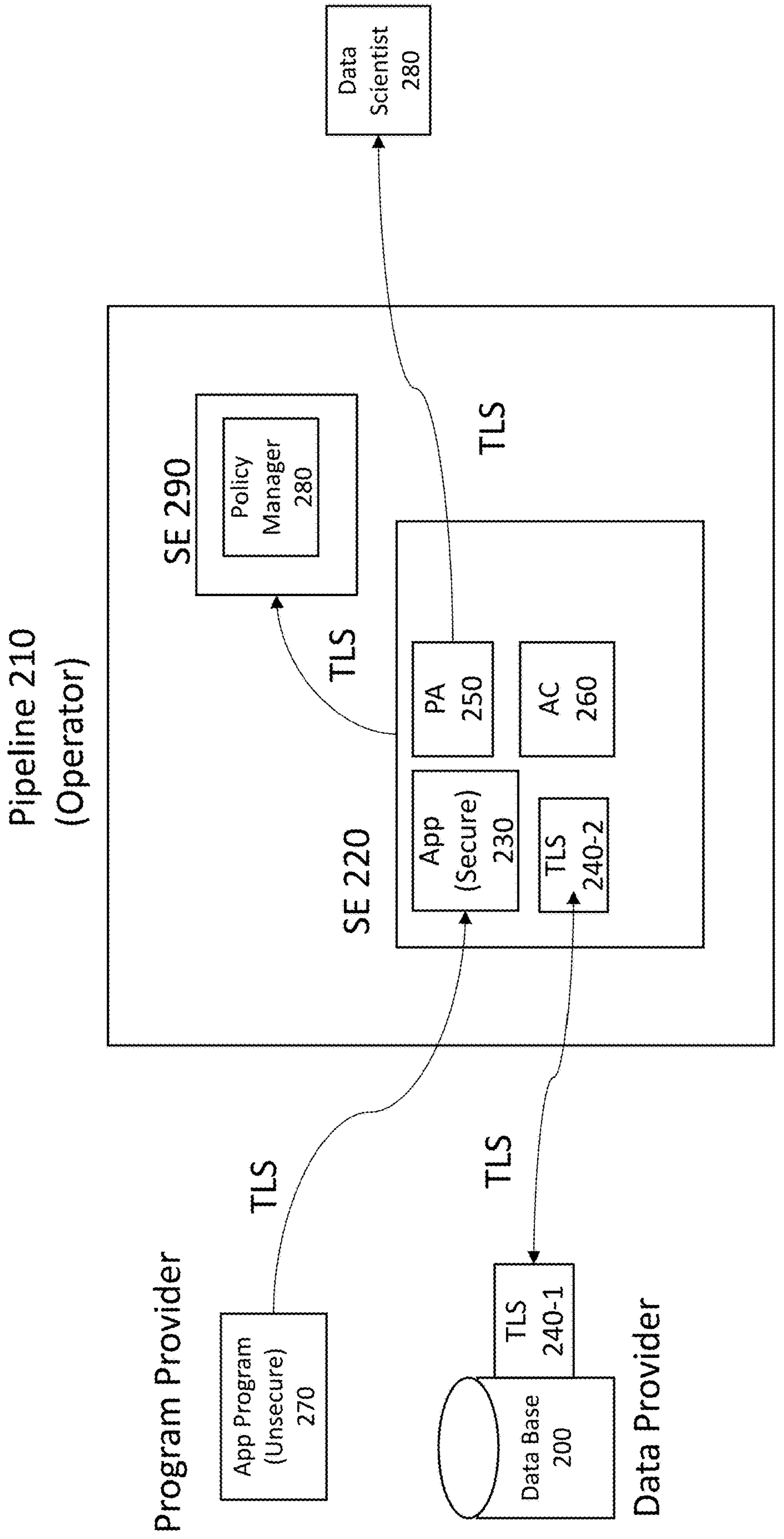
FIG. 2 is a simplified diagram of a general architecture of a secure enclave according to certain embodiments.

FIG. 2 shows a use case scenario for processing healthcare data according to some embodiments. A data provider provides database 200 containing data records some of whose attributes may be private data, such as a user's name, address, patient ID number, zip code, and other user-specific data. Database 200 is connected to one or more computers collectively referred to as a pipeline 210, possibly residing in a cloud server environment.

FIG. 2 also shows a computer program 270 (provided by a program provider) that resides outside the enclave 220. This, as described earlier, is an unsecure program as it is not contained in a secure enclave. Using method "Create and Populate Secure Enclave," program 270 creates a secure enclave in pipeline 210 and populates it with its secure application part, App 230. Since App 230 is inside a secure enclave it is, by definition, secure.

As described in method "Create and Populate Secure Enclave," pre-provisioned software may also be loaded into a secure enclave. SE 220 contains, inter alia, pre-provisioned software 240-2 that acts as one endpoint for a TLS (Transport Level Security) connection. The second endpoint 240-1 for the TLS connection resides with the database 200. (Any secure network connection technology, e.g., https, VPN, etc., may be used in lieu of TLS.)

The TLS connection may be used by App 230 to retrieve data from database 200. App 230 may also include a proxy mechanism for executing receipt of data records.

Additionally, SE 220 contains pre-provisioned software modules PA 250 (Policy Agent) and AC 260 (Access Controller) whose functions are discussed below.

Program App 230 in SE 220 may thus retrieve data from database 200 using the TLS endpoints 240-1 and 240-2. TLS technology ensures that the data being transported is secure. Database 200 may contain encrypted data records. Thus, App 230 receives encrypted data records. In operation, App 230 decrypts the received data records and processes them according to its programmed logic. (The method by which decryption occurs is described later.)

Using method "Execute Code in Secure Enclave" described above, App 230 may be invoked which may then retrieve and decrypt data from database 200. The result of the processing is may be directed to an entity labelled data scientist 280 under control of the policy agent PA 250. Generally, PA 250 operates in conjunction with policy manager 280. The functioning and inter-operation of PA250 and policy manager 280 will be described in more detail later.

In some embodiments, the policy manager 280 may exist in its own secure enclave 290.

FIG. 2 shows the pipeline containing 2 secure enclaves, 220 and 290. In embodiments, a pipeline may contain one or more secure enclaves. Furthermore, the one or more secure enclaves may be inter-connected (e.g., to distribute the computational work tasks). For example, the one or more secure enclaves may be inter-connected to achieve what is known as a map-reduce arrangement to achieve concurrent execution of computational tasks. A pipeline may be implemented using one or more computers, e.g., the secure enclaves may exist on multiple computers, e.g., in a cloud server environment. FIG. 2 shows a single database 200 connected to the enclave. In embodiments, one or more databases may be so connected to the one or more enclave (s).

In summary, a computational task may be achieved by encoding it as an application program with a secure and an unsecure part. When invoked, the unsecure part of the application creates one or more secure enclaves, injects its secure part into a secure enclave and invokes its execution. The secure part of the application may have access to data from (pre-provisioned) databases connected to the enclaves or from other enclaves. The secure part of the application then decrypts received data. Processing then proceeds as per the app's logic possibly utilizing the arrangement of the interconnected enclaves. The results are presented to the data scientist via the policy agent.

In comparison to the FHE dataset approach, in which the data is never decrypted and processing proceeds on encrypted data, in the arrangement shown in FIG. 2, the data inside an enclave is in encrypted form and is decrypted before processing. It may be re-encrypted before the results are shared with external entities. The arrangement of FIG. 2 may therefore be more efficient and achieve an improved speed of processing relative to FHE.

The pipeline technology described above allows computations to be carried out on datasets that may contain private and personal data. An aspect of pipeline technology is that data (and programs) inside a secure enclave are inscrutable, i.e., subject to policy control exercised by the policy manager (or its cohort, the policy agent). Furthermore, the outputs produced as a consequence of the execution of the program, may be directed according to policies also.

As an illustration, consider a computation carried out in a pipeline that calculates the body mass index (BMI) of individual patients stored in a dataset containing, inter alia, their weights, heights, date of births and addresses. The computation then proceeds to calculate the average BMI across various US counties.

Since these calculations involve private and personal patient data, the computations may be subject to privacy regulations. Various types of outputs may be desired, such as the following illustrative examples: (1) a dataset of 5 US counties that have the highest average BMI; (2) a dataset of 5 patients with street addresses with "overweight" BMI; (3) a dataset of patients containing their zip codes and BMI from Norfolk county, MA; (4) a dataset of patients with "overweight" BMI between the ages of 25-45 years from Dedham, Mass.; or (5) a dataset of patients containing their weight, height and age from Allied Street, Dedham Mass. In each case, the input to the computation is a dataset that may contain private and personal data and the output is a dataset that may also contain private and personal data.

The first output dataset above lists data aggregated to the level of county populations and does not contain PII data attributes. The result is independent of any single individual's data record; the result pertains to a population. A policy may therefore provide that such a dataset may be outputted, i.e., as plaintext.

On the other hand, the second outputted dataset above (1) contains personal identifiable information, i.e., street address, and (2) the number of items in the dataset, i.e., the cardinality of the output set, is small. A malicious agent may be able to isolate particular individuals from such a dataset. In this case, a policy may be formed to disallow such requests.

That is, a parameter, K, called the privacy parameter, may be provided that imposes a bound on the cardinality of the outputted datasets. Thus, an outputted dataset may be disallowed if its PII attributes identify less than K individuals.

Additionally, or alternatively, the output dataset may be provided in encrypted form inside a secure enclave to the intended recipient, e.g., the data scientist along with a computer program responsive to queries submitted by the data scientist. The latter may then use an (unsecure) application program to query the (secure) program inside the enclave and receive the latter's responses. Thus, the data scientist may not see the patient data but can receive the responses to his queries. Furthermore, the responses of the secure program may be constrained to reveal only selected and pre-determined "views" the output dataset, where the "views" may correspond to the generally accepted notions of views in database system. Alternatively, the output dataset may also be provided to the data scientist without enclosing it in a secure enclave by first encrypting the dataset using FHE.

In the third output request above, the data is being aggregated across zip codes of a county and therefore may not engender privacy concerns, provided that the number of such patients is large enough. In such examples, a policy may be formed that imposes a constraint on the size of the output dataset, e.g., output dataset must contain data pertaining to at least 20 patients. Similar policies may also be used for the fourth and fifth output requests.

In some embodiments, a policy may be formed that provides for adding random data records to an outputted dataset if the cardinality of the dataset is less than the imposed constrained limit. That is, a constraint is imposed such that enough records are included in the output dataset to achieve an output of a minimum size, e.g., 20 individuals.

Further challenges may arise when output requests (e.g., the third, fourth and fifth output requests above) are issued as a series of requests and the outputs are collected by a single entity (e.g., a data scientist) or multiple entities that collude to share the outputs. Since the output requests compute datasets that successively apply to smaller population sizes, there is a possibility that such "narrowing" computations may be used to gain information about specific individuals.

It has been shown in the literature (cf. Cynthia Dwork, *Differential Privacy: A Survey of Results*, International Conference on Theory and Applications of Models of Computation, 2008) that sequences of ever-increasing narrowing (or more accurate responses) ultimately leaks individual information.

FIG. 3 shows the various policies discussed above. These policies are intended for illustrative purposes, actual policies that are implemented may be different.

In some embodiments, a policy agent may be configured so as to be included as a pre-provisioned software in one or more secure enclaves of a pipeline. The policy agent receives its policies from a Policy Manager (described below) and imposes its policies, some examples of which have been provided in the discussion above, on every outputted dataset. Out of band agreements between various (business) parties may be used to allow parties to specify and view the pre-provisioned policies contained in a policy agent.

Policy agent software also records, i.e., logs, all accesses and other actions taken by the programs executing within an enclave.

A Policy Manager may be configured to manage one or more policy agents. The Policy Manager may also perform other functions which will be described below. For simplicity, the present disclosure illustrates a single Policy Manager for a pipeline managing all policy agents in the pipeline in a master-slave arrangement.

The present disclosure also shows a Policy Manager running in the domain of the Operator of the pipeline for illustrative purposes, and various alternatives are possible. In some embodiments, the Policy Manager may be implemented in any domain controlled by either the operator, data provider, program provider or data scientist. If the Policy Manager is implemented using decentralized technology, the control of the Policy Manager can be decentralized across one or more of the above business entities. The term "decentralized" as used in this disclosure implies that the policies that control a policy manager may be provided by multiple parties and not by any single party.

For example, FIG. 7 shows one illustrative embodiment of a decentralized control of a policy manager. FIG. 7 shows a table contained in the policy manager whose rows describe groups. A group is a collection of collaborating entities and the elements related to their collaboration. The group of collaborating entities exercise control of the policy manager via their individual policies. The first row shows a group named Group 1 which has entity named A1 as a member providing an algorithm a1, another member named D1 providing data d1. The data and algorithm provided by the two members has been processed and a load image has been readied to be loaded into a pipeline. The readied load image is stored in secure storage and may be accessed by using link L1.

In some embodiments, a policy agent may record its state with the Policy Manager. Additionally, the Policy Manager may be architected to allow regulators and/or third-party entities to examine the recorded state of the individual Policy Agents. Thus, regulators and third-party entities may examine the constraints under which datasets have been outputted. In embodiments, a possible implementation method for the Policy Manager is as a block-chain system whose ledgers may then contain immutable data records.

In scenarios discussed above, a policy may dictate that a data scientist may receive an outputted dataset enclosed in a secure enclave. This means that the data in the dataset is non-transparent to the data scientist. The latter is free to run additional output requests on the outputted dataset in the enclave by injecting new requests into the enclave. In those cases, when the outputted dataset does not have any PII data or does not violate the privacy parameter constraint, the dataset may become unconstrained and may be made available to the data scientist.

In some embodiments, a data scientist or other requestor may view the contents of a dataset contained within an enclave. The contents of an enclave may be made available to a requestor by connecting the enclave to a web browser and causing the contents of the enclave to be displayed as a web page. This prevents the requestor from saving or copying the state of browser. However, in some cases, the requestor may take a visual image of the browser page.

In some embodiments, a data scientist may submit data requests, which are then curated using a curation service. If the curation service deems the data requests to be privacy-preserving, then the data requests may be processed using the dataset in the enclave and the outputted dataset may be provided to the data scientist as an unconstrained dataset. In this manner, the curation service checks and ensures that the submitted data requests are benign, i.e., that the data requests do not produce outputs that violate privacy regulations.

As discussed above, a further challenge associated with processing private data using enclaves is whether policies can be provided about the computations carried out within the enclave, since the processes internal to an enclave are inscrutable. Consider, for example, a use case of secure enclave technologies, following the general description above with respect to FIG. 2. A first enterprise possessing encrypted data may store the data in an enclave. The data in the enclave may be processed and readied for use by a second enterprise providing the pipeline, the computer program processing the data being provided by a third enterprise. A data scientist may now inject a data request into the enclave and expect an outputted dataset as a result. As explained above, in one instance, the outputted data set may be provided to the data scientist as data enclosed in an enclave. In another instance the outputted dataset may be provided as an encrypted store of data. In the latter case, the data scientist may be provided a decryption key so as to provide him/her access to the data. All these actions are subject to the policies determined a priori by either the first, second or third enterprise.

Furthermore, the policy in question may require that the access to process the data and receive the outputted dataset by the data scientist must be authorized. That is, the access by the data scientist must be authenticated. Data scientists on their part may require that they be assured that their data requests operate on data provided by a specified data provider since the integrity of data is crucial to the data processing paradigm. In particular, if the data scientist intends to share the outputted results with a third party, the data scientist may need to assure the former of the integrity of the input data and the fact that the results were obtained by executing a particular data request. Regulators may require that the entire process of storing and processing the data must be transparent and to be made available for investigations and ex post facto approval.

Figure 4A:
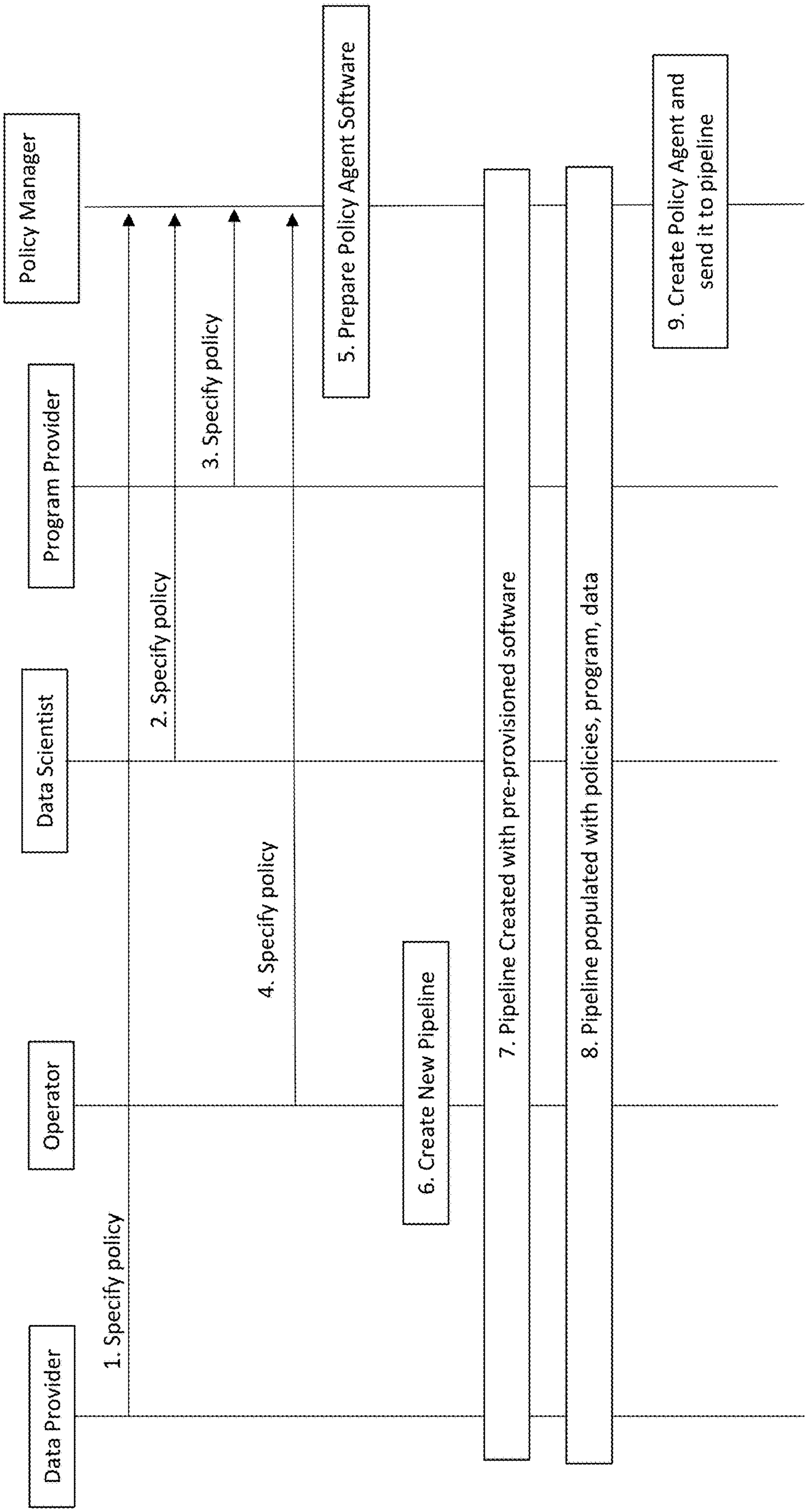
FIG. 4A is a simplified diagram of an illustrative orchestration to ensure that policies are properly programmed in secure enclaves, according to certain embodiments.

To address the various concerns stated above, an orchestration method may be performed as shown in a workflow diagram in FIG. 4A. The following entities are involved in the workflow: (1) data provider, i.e., the entity that owns data; (2) operator, i.e., the entity that provides pipeline technology; (3) a program provider that provides the computer program to process data; (4) data scientist, i.e., an entity that wishes to obtain outputted results; and (5) policy manager, which may include a software module controlling the policy agent.

Referring to FIG. 4A, in step 1, 2, 3 and 4 the data provider, the data scientist, the program provider and the operator respectively specify their policies. In step 5 the Policy Manager prepares to initiate the Policy Agent. In step 6, the operator creates a new pipeline and, in step 7, informs the participants in the orchestration about the creation of the pipeline. The participants may now populate the pipeline with data, programs, and policies. Note that the pipeline is initiated also with pre-provisioned software libraries.

Figure 4B:
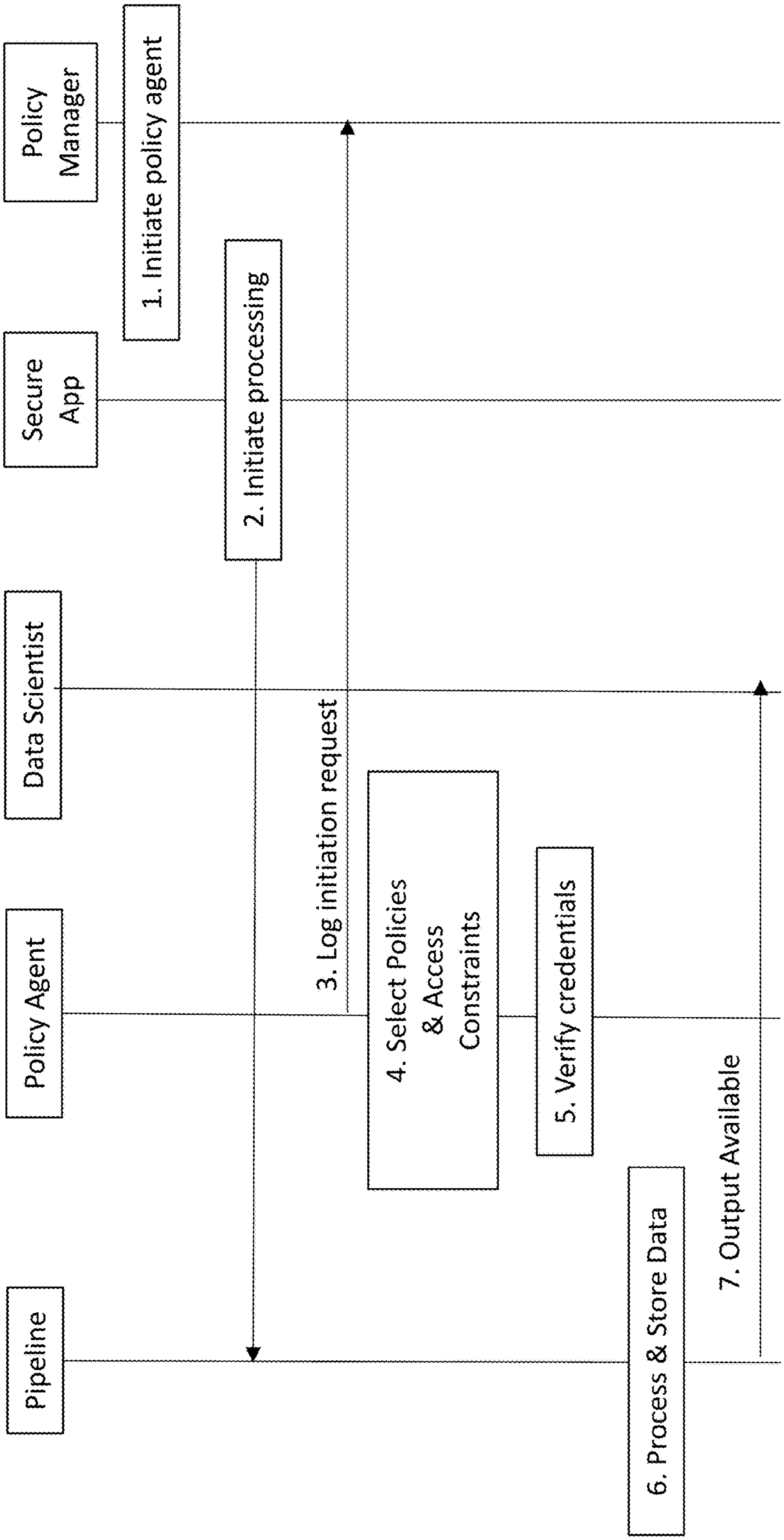
FIG. 4B is a simplified diagram of an illustrative orchestration to ensure that data is computed subject to policy constraints, according to certain embodiments.

Referring to FIG. 4B shows the orchestration between a data provider, a pipeline, a secure application program provided by a program provider, a policy manager, a data scientist and a policy agent.

Step 1. The policy manager initiates the policy agent that it had prepared in step 5 of FIG. 4A.

Step 2. Secure application initiates a processing request.

Step 3. Logs the initiation request.

Step 4. Policy agent selects appropriate policies and access credentials related to the processing request.

Step 5. Policy agent (with help of policy manager) verifies credentials. If the credentials are not satisfied, the request is terminated.

Step 6. Pipeline executes the processing request and stores the data.

Step 7. Pipeline notifies data scientist that the requested output is available.

Key Management

Public key cryptography relies on a pair of complementary keys typically called the private and public keys. The latter may be distributed to any interested party. The former, i.e., the private key, is always kept secret. Using the public key distributed by, say Alice, another party, say Bob, may encrypt a message and send it to Alice safe in the knowledge that only Alice can decrypt the message by using her private key. No other key can be used to decrypt the message encrypted by Bob. As mentioned before, ownership of a private key is a major concern and several techniques are discussed in literature relevant to this topic.

Secure enclave technology may be used to address the private key ownership issue by ensuring that the private key (corresponding to a public key) always resides in a secure enclave. This may be accomplished, for instance, by creating a first secure enclave and pre-provisioning it with public/private key cryptography software that creates pairs of private and public keys. Such software is available through opensource repositories. A computer program residing in a second secure enclave may then request the first enclave to provide it (using a secure channel) a copy of the private key that it needs. Thus, the private key never exists outside the secure enclave infrastructure, always residing in secure enclaves and being transmitted between the same using secure channels.

In some embodiments, a policy manager may be pre-provisioned with public/private key software and the Policy Manager be enclosed in a secure enclave as shown in FIG. 2 (cf. 280).

A secure enclave may then request its policy agent for a private key. The policy agent, as discussed above, operates in conjunction with the policy manager and may request the same from its policy manager. A computer program executing in a secure enclave may need a private key to decrypt the encrypted data it may receive from a data provider. It may request its policy agent who may then provide it the needed private key for decryption purposes.

As explained earlier, encryption technologies referred to as hash functions or hashing algorithms exist that can take a string of cleartext, often called a message, and encrypt it as a sequence of hexadecimal digits, i.e., sequence of digits [0-9, A-F]. Examples of publicly available hash functions are MD5, SHA-256, SHA-512. The latter two functions use keys of length 256 and 512, respectively. As discussed above, the length of the keys is a factor in ensuring the strength of an encryption technology to withstand malicious attacks.

One property of hash functions that map cleartext into hexadecimal digits is that they do not map different cleartexts to the same digits. Thus, a piece of cleartext may have a unique signature, i.e., the output of the hash function operating on the cleartext as input.

If a secure enclave containing programs and data can be viewed as comprising cleartext then it follows that every secure enclave has a unique signature. Thus, by applying a suitable hash function to the contents of a secure enclave, a signature of that enclave is obtained. The signature is unique in that no other and different secure enclave will have that signature.

If a secure enclave is populated with a known computer program and a known dataset then that secure enclave's signature may be used to assert that the secure enclave is executing (or executed) the program on the known dataset by comparing the signature of a secure enclave with previously stored signatures.

Thus, a data provider, if provided with a signature of the enclave, may be assured that its dataset is uncorrupted or unchanged and is operated upon by a pre-determined program.

Similarly, a program provider may be assured that its programs are uncorrupted and unchanged. A data scientist may be assured that its output is the result of processing by the pre-determined program on pre-determined data.

Since a policy manager may be programmed to disallow the operator to access the contents of a secure enclave by denying access to the relevant decryption keys, the operator of the pipeline cannot view or edit the contents of the secure enclave.

In the present disclosure, secure enclaves may be pre-provisioned with software to compute hash functions that may be invoked by the policy manager to create signatures. The policy manager may then be programmed to provide these signatures as certificates upon request to various entities, e.g., to the data provider or the program provider.

Figure 10:
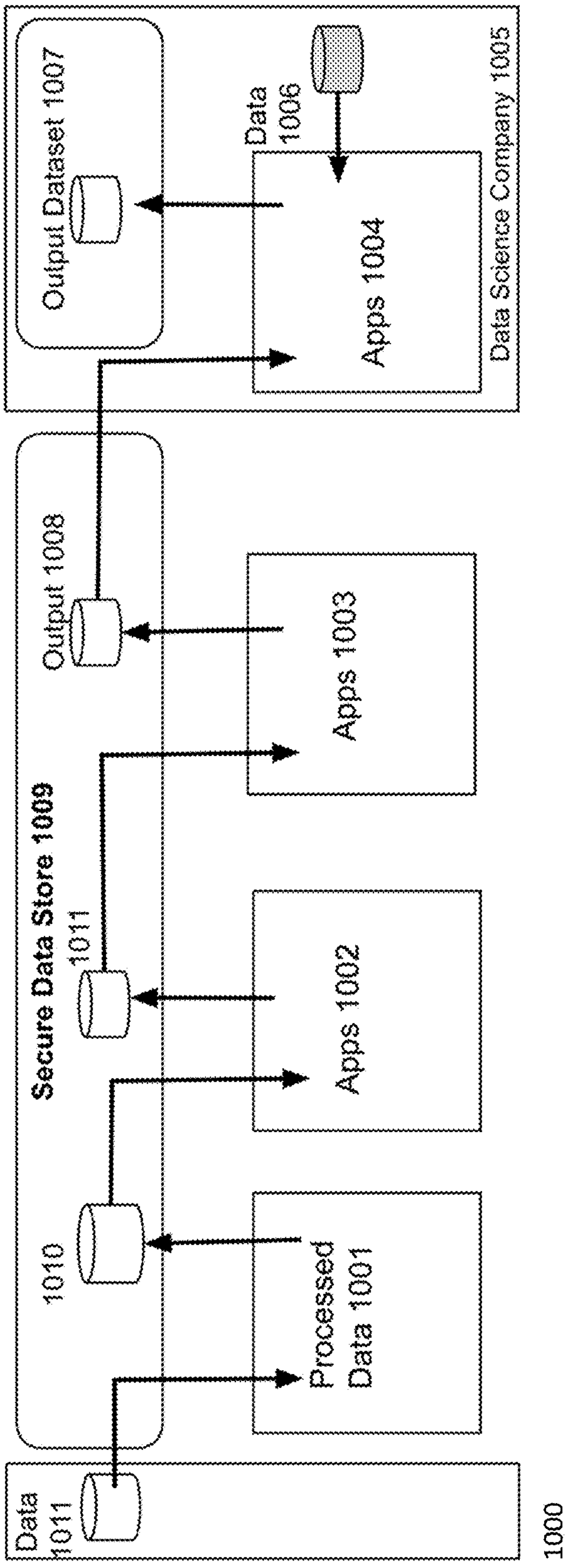
FIG. 10 is a simplified diagram of an architecture of a federated group of enterprises collaboratively receiving, storing and processing private data, according to certain embodiments.

Referring now to FIG. 10, an initial dataset 1001 may be stored in a secure enclave 1001 where it may be processed and outputted as dataset 1010. Dataset 1010 exists in a secure data layer 1009. One or more apps may be injected by data scientists into enclave 1002 and the dataset 1010 may be provided to such apps. Upon processing, the outputted dataset may be stored as output 1008. The latter may be further injected into enclave 1004 where an enterprise 1005 may use (proprietary) apps to process and output the result as dataset 1007. Note that output dataset 1007 is encrypted.

Thus, enterprise 1005 has a choice to run apps injected into enclave 1003 or to receive the dataset 1008 into a different enclave 1004 and run their proprietary apps therein.

That is, a series of enclaves 1001, 1002, 1003 and 1004 (FIG. 10) may be assembled wherein each enclave receives encrypted data from a secure data store 1009 and produces a secure (encrypted) dataset in turn for the next in line enclave. Thus, the original data owner 1000 may provide its data 1011 for processing to a third party, i.e., enterprise 1005 and be assured that no private or personal data may leak.

Enterprise 1005 has the flexibility to run its own data requests on the datasets and provide the results of the processing to its customers, along with certificates that the appropriate data requesting programs were executed and the provenance of the input data was ascertained. Enterprise 1005 may assume ownership of the dataset 1007 but then it assumes legal responsibility for its privacy.

Figure 9:
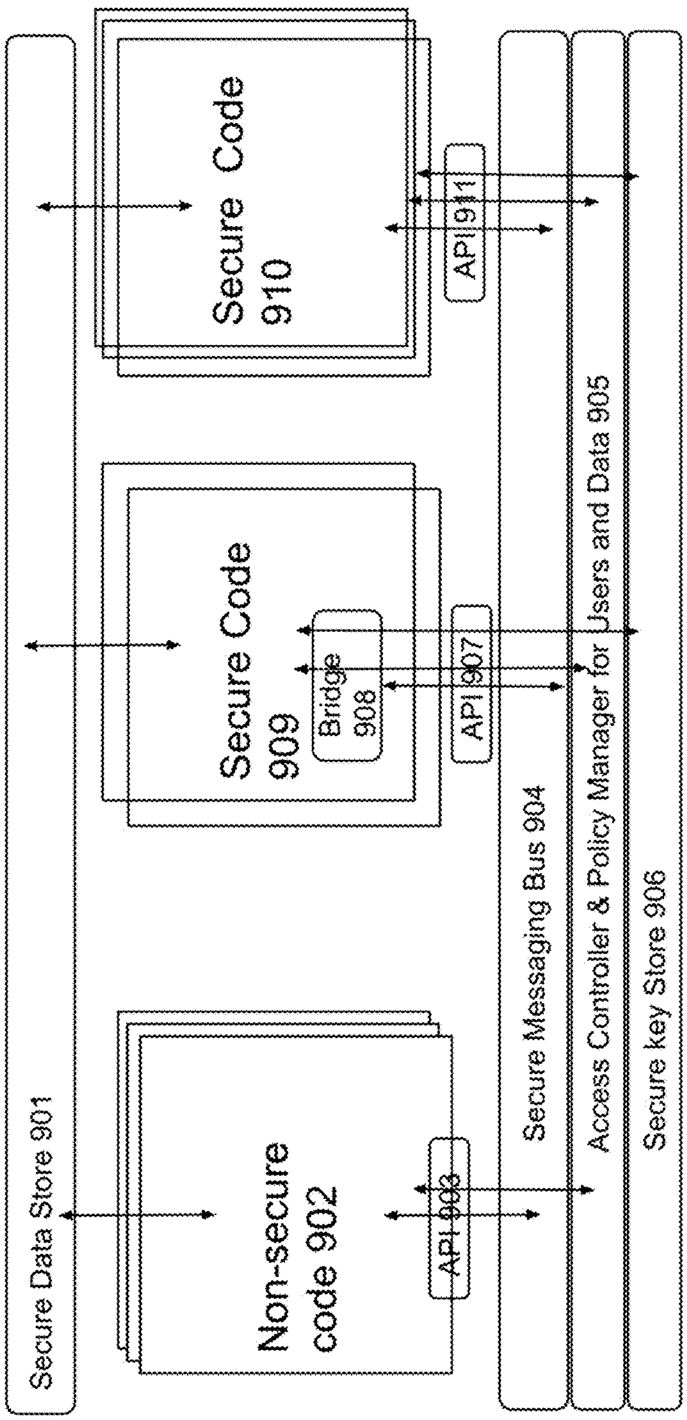
FIG. 9 is a simplified diagram of an architecture of a federated group of enterprises collaboratively receiving, storing and processing private data, according to certain embodiments.

FIG. 10 shows a sequence of enclaves, each enclave being connected to another enclave via an intermediate secure data layer. However, in embodiments, as shown in FIG. 9, several enclaves 909 and also 910 may be executing in a concurrent manner. Furthermore, not all code may reside in enclaves, enclaves may be mixed with computing environments that contain non-secure code as needed, cf. 902 (FIG. 9).

Along with the secure data layer available to all enclaves, additional layers may be provided for secure messaging 904, access control and policy agent communication 905 and exchange of cryptographic keys 906. These additional communication layers are provided so that enclaves may exchange various kinds of data securely and without leaks with each other.

Figure 8:
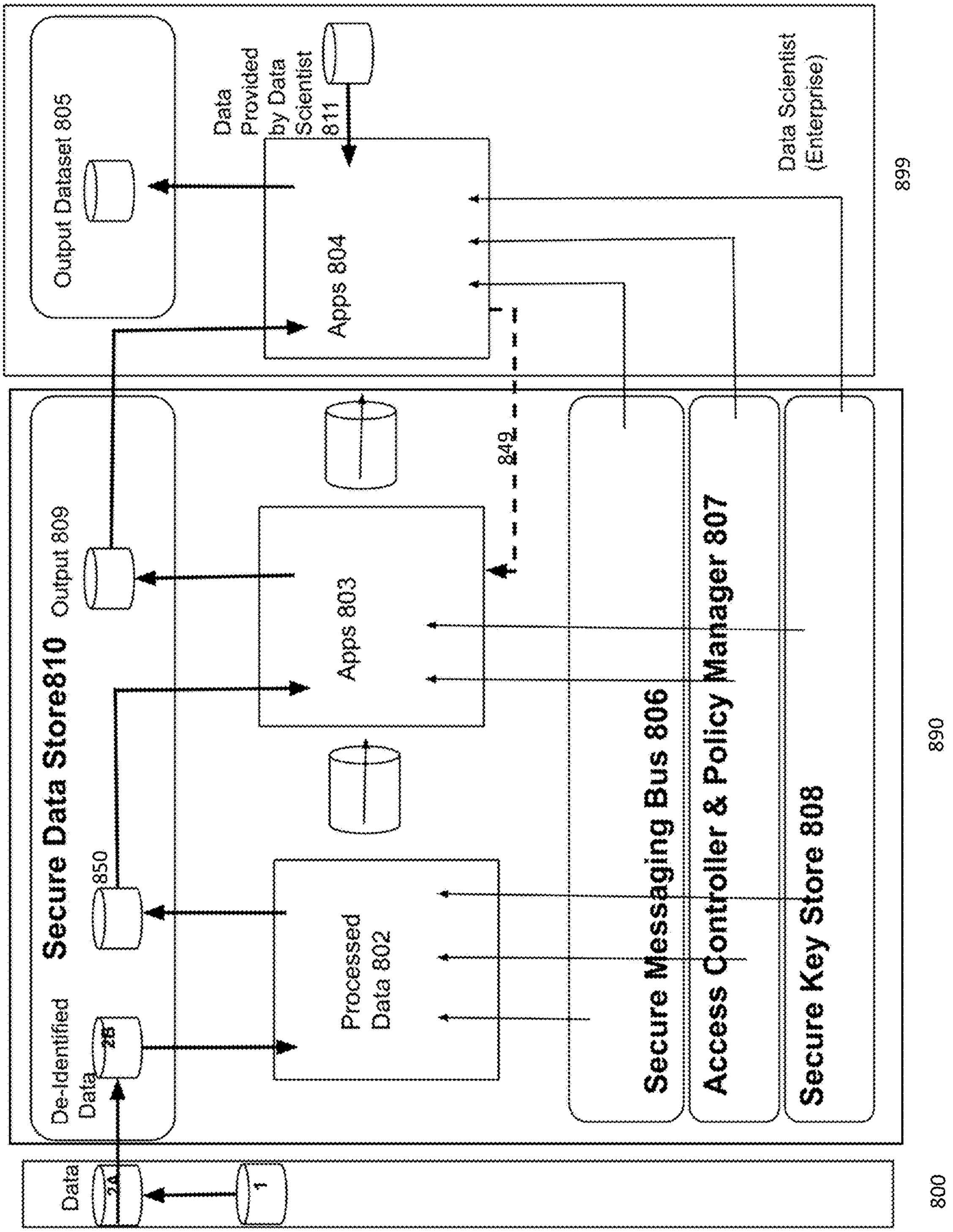
FIG. 8 is a simplified diagram of an architecture of a federated group of enterprises collaboratively receiving, storing and processing private data, according to certain embodiments.

Referring to the illustrative embodiment shown in FIG. 8, a first enterprise 800 owns dataset 1 which it may de-identify and anonymize to get dataset 2A. As discussed before, the de-dentification procedures may not be completely effective and the dataset 2A may still contain some private and personal data. The first enterprise provides a copy of dataset 2A, shown as 2B, in a secure data layer 810 so that it may be made available for processing by a second enterprise, 890.

Enterprise 890 receives the dataset 2B and causes it to be stored in enclave 802 where it may be processed and readied for further processing, whereupon it is stored in the secure data layer 810 as dataset 850.

Enclave 802 is pipelined to enclave 803 which implies that the dataset 850 is outputted from enclave 802 and provided as input to enclave 803. The apps in enclave 803 may now process the data and produce as output dataset 809.

In turn, enclave 803 is pipelined to enclave 804 which exists in a network administered by enterprise 899. That is, enclave 803 is administered by enterprise 890 and enclave 804 is administered by enterprise 899. The latter enterprise may inject additional data 811 into enclave 804, and also inject apps to process the dataset 811 in conjunction with input dataset 809, to produce dataset 805. The result of the computation may be made accessible to a data scientist at enterprise 899 as per the dictates of the policy agent/manager.

FIG. 8 also shows an illustrative embodiment 849 in which enterprise 899 may contribute data from enclave 804 (possibly obtained as a result of processing) to be injected into enclave 803. This allows obtained results to be re-introduced for further processing, i.e., allowing feedback loops for further processing of results.

In the foregoing discussion, various embodiments have shown system and methods for collaborative storing, processing and analyzing of data by multiple parties. For example, FIG. 8 shows three enterprises 800, 890 and 899 that collaborate. Enterprise 800 provides data, enterprise 890 provides the infrastructure that stores the data in an enclave and enterprise 899 processes the data by injecting specific data requests into the enclave. In one embodiment, a central trust model is used in which one of the enterprises, e.g., the enterprise that provides the infrastructure, is trusted to ensure that data provided by a first enterprise is made available to a second enterprise under a collaborative agreement. That is, the trusted enterprise ensures that data access and data processing obey the various ownership and processing concerns. Data providers would like to be ensured that their data is only processed by approved enterprises. Data processing people would prefer that their data requests be kept private and the details of their processing requests not be shared with competitors. Maintenance of such concerns can be reposed in the trusted enterprise. Such an embodiment may be referred to as a centralized trust model, i.e., trust is placed in one enterprise or entity.

In another embodiment, a decentralized trust model may be provided in which multiple enterprises are trusted. Such a trust model may be particularly apt in an open marketplace where data providers contribute data and analyzers contribute data requests, i.e., computer programs, that process the contributed data. No single enterprise or entity is to be trusted in the decentralized model. Rather an openly available structure is provided that any third party may access to verify that the constraints governing the data and algorithm providers are being maintained.

FIG. 7 shows one illustrative embodiment of a decentralized trust model. FIG. 7 shows a table whose rows describe groups. A group is a collection of collaborating entities and the elements related to their collaboration. The first row shows a group named Group 1 which has entity named A1 as a member providing a program a1, another member named D1 providing data d1. The data and algorithm provided by the two members has been processed and a load image has been readied to be loaded into an enclave. The readied load image is stored in secure storage and may be accessed by using link L1.

As explained above, in order to load the image into an enclave, a specific encryption key is needed to encrypt the data (whose corresponding decryption key will be used by the enclave to decrypt the data).

It is to be understood that the foregoing embodiments are illustrative, and that many additional and alternative embodiments are possible. In some embodiments, at least a portion of the federated pipeline described above may be run on hardware and firmware that provides protected memory, such as Intel Security Guard Extensions (SGX), the implementation details of which are described at https://www.intel.com/content/www/us/en/architecture-and-technology/software-guard-extensions.html. In some embodiments, at least a portion of the federated pipeline may be run using virtualization software that creates isolated virtual machines, such as AMD Secure Encrypted Virtualization (SEV), the implementation details of which are described at https://developer.amd.com/sev/. In some embodiments, the federated pipeline may manage cryptographic keys using a key management service, such as the Amazon AWS Key Management Service (KMS), which described in further detail at a https://aws.amazon.com/kms/. However, these examples of hardware, firmware, virtualization software, and key management services may not independently create isolated software processes that are based on cryptographic protocols which can be used to create federated pipelines that have different ownerships, policies and attestations. Accordingly, in some embodiments, middleware (e.g., a layer of software) may be provided that can use underlying hardware/firmware, operating system, key management and cryptographic algorithms to achieve secure and private isolated processes, such as secure enclaves.

In some embodiments, secure enclaves can be linked together to form pipelines. Consistent with such embodiments, computations can be broken into sub-tasks that are then processed in pipelines, either concurrently or sequentially or both based on the arrangement of the pipelines.

In some embodiments, an attestation service can be associated with a pipeline. The attestation service establishes a chain of trust that originates from the start of the pipeline to the end of the pipeline, which provides external entities assurances even though the internal contents of a pipeline may not be observable to external entities. In some embodiments, the chain of trust can be further extended without extending the associated pipeline itself.

One way of dealing with healthcare data is to anonymize or mask the private data attributes, e.g., mask social security numbers before it is processed or analyzed. In some embodiments of the present disclosures, methods may be employed for masking and de-identifying personal information from healthcare records. Using these methods, a dataset containing healthcare records may have various portions of its data attributes masked or de-identified. The resulting dataset thus may not contain any personal or private information that can identify one or more specific individuals.

The foregoing embodiments related to federated architecture can be applied to provide a sentinel system and method to determine durability of vaccines. For example, such a system can allow calculate aggregate statistics related to vaccine durability based on data from multiple enterprises or health systems without a need to store personally identifiable patient data in a single location. In some embodiments, an enterprise is an entity that has a health record, e.g., a health system, an academic health center, or a private provider of healthcare data. In some embodiments, an enterprise is an entity providing or performing analysis of healthcare information or providing software for analysis of healthcare information, for example, providing information related to vaccine durability. In some embodiments, each enterprise can process data (e.g., patient data) on its own secure enclave, without storing personally identifiable patient data in a central location. In these embodiments, an output can be provided to a central node from each secure enclave so that the central node can provide an aggregate output related to vaccine durability. In some embodiments, an enterprise can include multiple secure enclaves, for example, an enclave for each of multiple information systems or EHR systems within a hospital system.

In some embodiments, the secure enclaves are constructed by the enterprise where they are located, e.g., by each health system. In other embodiments, the secure enclaves are constructed by another enterprise, e.g., an enterprise providing analysis of healthcare information or providing software for analysis of healthcare information. In some embodiments, analysis can be performed within the secure enclave by the entity where the secure enclaves are located, e.g., by each health system. In some embodiments, analysis can be performed within each secure enclave by another enterprise, such as one providing analysis of healthcare information or providing software for analysis of healthcare information.

Figure 12:
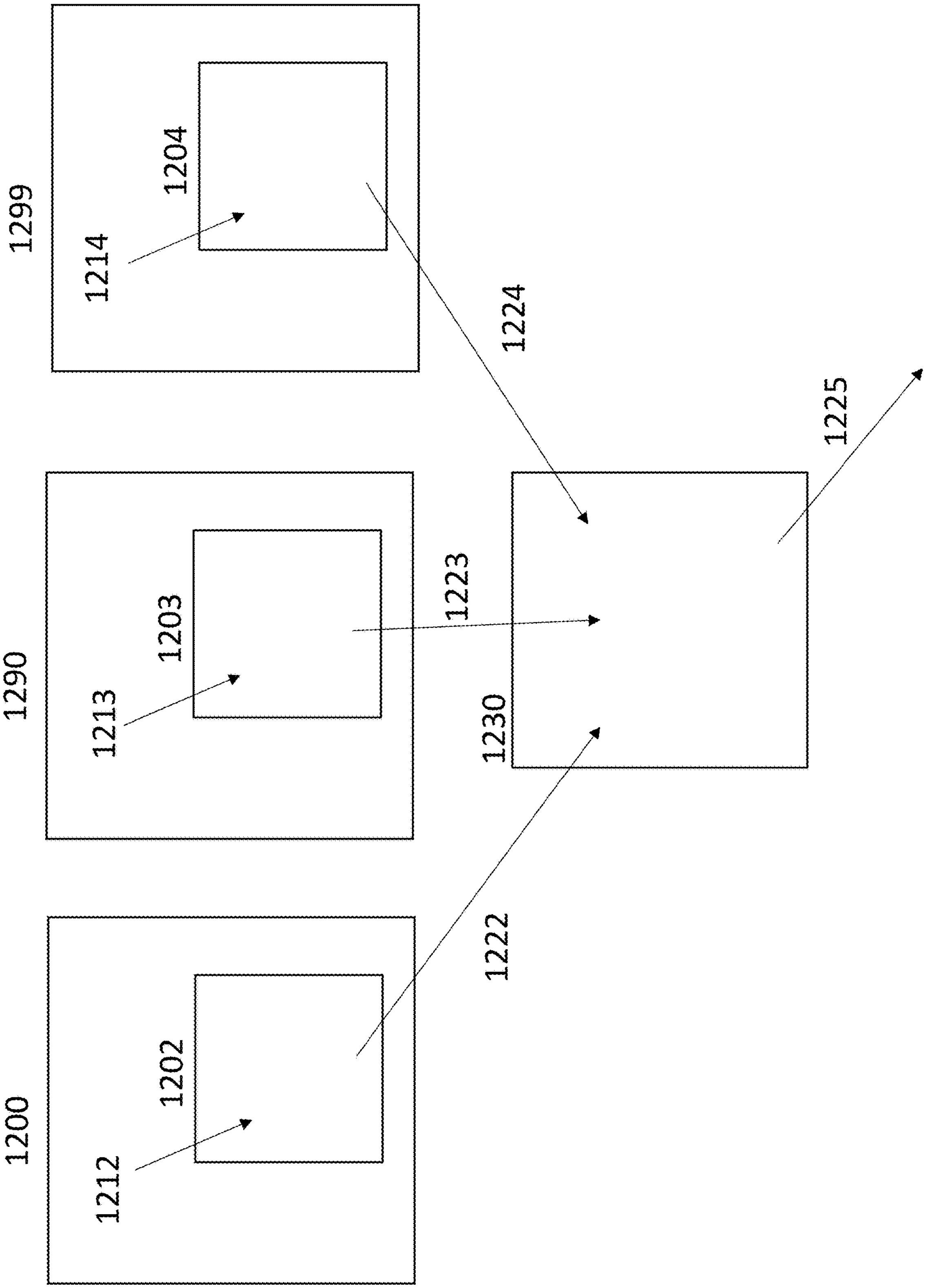
FIG. 12 shows a simplified diagram of an architecture of a federated group of enterprises with a central node according to some embodiments

An exemplary embodiment is shown in FIG. 12. In this embodiment, a plurality of secure enclaves 1202, 1203, 1204 are formed. In some embodiments, each secure enclave can be formed within an enterprise 1200, 1290, 1299, e.g., a health system. Each enclave can receive input data 1212, 1213, 1214 from the respective enterprise and process that input data using pre-provisioned software within the secure enclave. For example, the input data can include patient data from each health system, including a vaccination status, a vaccination date, a test date, and a test result. A vaccination date can include to the date of any vaccination dose, e.g., a first dose, a second dose in a series, or a booster dose. A vaccination can include more than one date in a series of vaccination doses. In some embodiments, this input data is received in the secure enclave in encrypted form and decrypted within the secure enclave using one or more cryptographic keys. Known encryption techniques can be used in connection with these embodiments. In some embodiments, the input data is de-identified before being received in the secure enclave. This data can be processed within each enclave, e.g., using a regression model to provide an output data set 1222, 1223, 1224, e.g., an output related to vaccine durability. The output of each enclave can then be sent to a central node 1230. The central node can be pre-provisioned with software for applying an aggregate analysis to the output from the plurality of enclaves to provide an aggregate output 1225. In some embodiments, the central node is also a secure enclave. However, if the output data from the secure enclaves does not include personally identifiable information, e.g., if the output data is aggregated for a given health system, the central node need not be a secure enclave.

In some embodiments, the output data 1222, 1223, 1224 from each secure enclave does not include personally identifiable information, e.g., if the output data includes aggregated data or parameters for the respective enterprise or health system or if the output data includes de-identified data. In these embodiments, the output data need not be encrypted before sending to the central node. In these embodiments, the central node need not be a secure enclave. Alternatively, in other embodiments, the output data can include personally identifiable information. In these embodiments, the output data can be encrypted before sending to the central node, the central node can be a secure enclave, and the output data can be decrypted by software within the central node using one or more cryptographic keys. In some embodiments, the data within each secure enclave is decrypted using a pair of keys, e.g., public and private keys. In some embodiments, each secure enclave is encrypted with a different pair of public and private keys. In some embodiments, the secure enclaves are encrypted with a single pair of public and private keys.

In some embodiments, rather than storing individual patient data in a single location there can be a 'coordinator' or central node where pre-computed Risk Ratios or odds ratios from each of the federated nodes or enclaves are aggregated. In these embodiments, the central node itself DOES NOT receive or store any patient data. In some embodiments, this coordinator function is provided by enterprise providing analysis of healthcare information or providing software for analysis of healthcare information, e.g., by a software provider. In some embodiments, this coordinator function is provided by a national, state, or local health agency or organization. Such a coordinator node can be made capable of providing an alert based on the 'trajectory of the temporal Relative Risk curve' on a single system, single state, multiple systems or states, or for a larger geographical region or the entire country by computing with minimal information (e.g., number of vaccinated people in the cohort, number of unvaccinated people in the cohort, number of infections in each subset, number of symptomatic infections etc.). For example, an unadjusted odds ratio can be determined from aggregate counts of infections and numbers of vaccinated and unvaccinated people in the cohort.

In other embodiments, ONLY the Risk Ratios are shared from each federated node and the coordinator node can still compute an aggregate output, such as a composite or aggregate Risk Ratio and associated uncertainty (confidence interval). In these embodiments, not even counts of the patients need be shared to the coordinator node. A visualization of an individual node's information is provided by the 'federated node' or secure enclave as the coordinator will not have this information. This embodiment is useful when some part of the federation wants to minimize information sharing with the party that is providing the 'coordinator' function.

In some embodiments, the system uses aggregate statistics without sharing individual statistics from each federated node. In some embodiments, individual data from enclaves is sent to the central node and combined to form a new cohort. In this embodiment, analysis, e.g., a regression analysis, can be performed on this new cohort in the central node. In these embodiments, at least a portion of the input data from each secure enclave is sent to the central node. In these embodiments, the input data from individual enclaves can be encrypted before sending to the central node, the central node can be a secure enclave, and the output data can be decrypted by software within the central node using one or more cryptographic keys. By combining data, trends that are too small to be seen in an individual dataset can emerge from a larger, combined dataset.

Yet another embodiment is a total lack of a 'coordinator' function in the network. Here, as in Bitcoin and various Blockchain implementations, the end system, e.g., on the desktop of the CDC director, acts as the sole aggregator.

In some embodiments, an alert functionality is configured by the user of the end system based on various thresholds of a Temporal Risk Ratio curve. For example, an alert can be configured by the enterprise or user who operates the central node or performs analysis within the central node. In some embodiments, an alert can be triggered when the odds ratio of testing positive relative to the odds ratio of testing positive at a time of full protection (e.g., a defined interval after vaccination) exceeds a threshold value. In these embodiments, comparing to a time of full protection can provide an estimate of absolute effectiveness. In some embodiments, an alert can be triggered when the odds ratio of testing positive relative to the odds ratio of testing positive at baseline (e.g., shortly after vaccination) exceeds a threshold value. In some embodiments, an alert can be triggered when a month-to-month change (e.g., an increase) in the odds ratio of testing positive exceeds a threshold value.

In some embodiments, vaccinated versus unvaccinated individuals are compared to establish when the protection against infection has been lost (like a vaccinated vs. placebo group in a clinical trial). However, in some health systems, individuals who are not recorded as being vaccinated are not necessarily unvaccinated. For example, individuals may have received vaccines elsewhere and not had the vaccination recorded in the Health System database, etc. This is related to how different states and hospitals would maintain syncing between registries and electronic health records, which is inherently going to be quite variable. Particularly as the vaccination rate in the population increases to high numbers (e.g. >90% in elderly people), this "contamination" of unvaccinated cohorts with vaccinated individuals will have substantial impacts on estimation of vaccine effectiveness.

To get around this, in some embodiments, a strategy is for the system to assess durability by only considering data from vaccinated patients. The "baseline risk of infection" is determined based on a predetermined interval or time (e.g., 4-10 days) after the first vaccine was received. During this time period, per the phase 3 trials and real world studies, there should not yet be an observed protection against infection—thus, this interval is considered to approximate the unvaccinated state. In some embodiments, the predetermined interval is determined based on the time that it takes for a vaccine to provide protection against infection. The odds of being infected each day after to this baseline rate is compared to determine when a fully vaccinated individual's risk of infection is "back to baseline."

In some embodiments, an approach that considers only data from vaccinated individuals makes the system more scalable. Relying on access to adequate numbers of confidently unvaccinated individuals would likely hamper the speed and quality of such an analysis. For example, health systems did not know what to do with data from vaccinated patients because they were not able to make a high-confidence unvaccinated cohort. An approach that considers only data from vaccinated individuals circumvents that by just relying on individuals for whom "vaccination=YES," which we will generally have much more confidence in than "vaccination=NO."

In some embodiments, assessment of antibody durability is performed using a cohort study or case-control study. Assessment of antibody durability can be performed using any known methods for forming a cohort. In some embodiments, data from a cohort study or a case-control study can provide input to a secure enclave for calculation of vaccine durability. In some embodiments, analysis of a cohort study or case control study can occur within a secure enclave of each enterprise. In a cohort study, groups can be defined based on an exposure, e.g., vaccination status, and the rate of an outcome, e.g., infection, is assessed between groups. For example, the question is how the rate of the outcome differs based on exposure. In a case-control study, groups are defined based on outcome, e.g., infection status, and the rate of an exposure, e.g., vaccination, is assessed between groups. For example, the question is what the odds are of being a case for exposed versus non-exposed people. FIGS. 13A-13B and 14A-14B show an exemplary comparison of a cohort study and a case-control study.

Figure 13B:
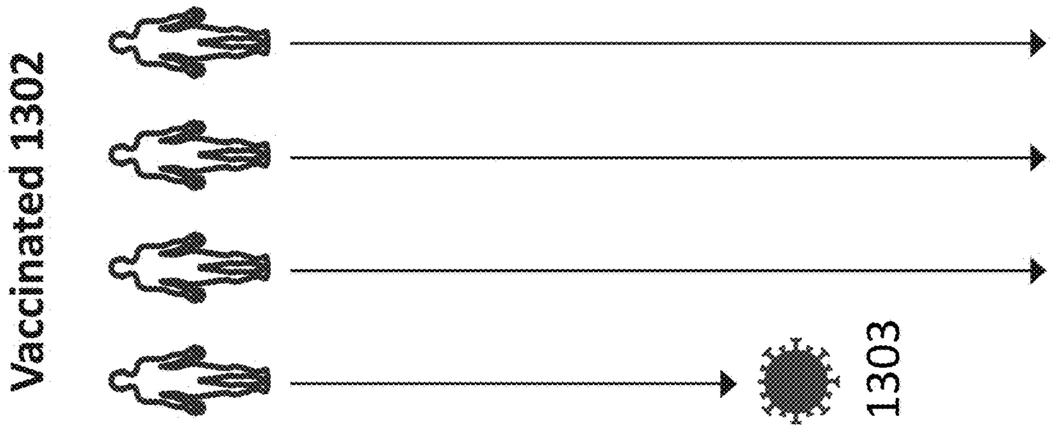
FIG. 13B shows a schematic of a vaccinated cohort in a cohort study, according to certain embodiments.
Figure 13A:
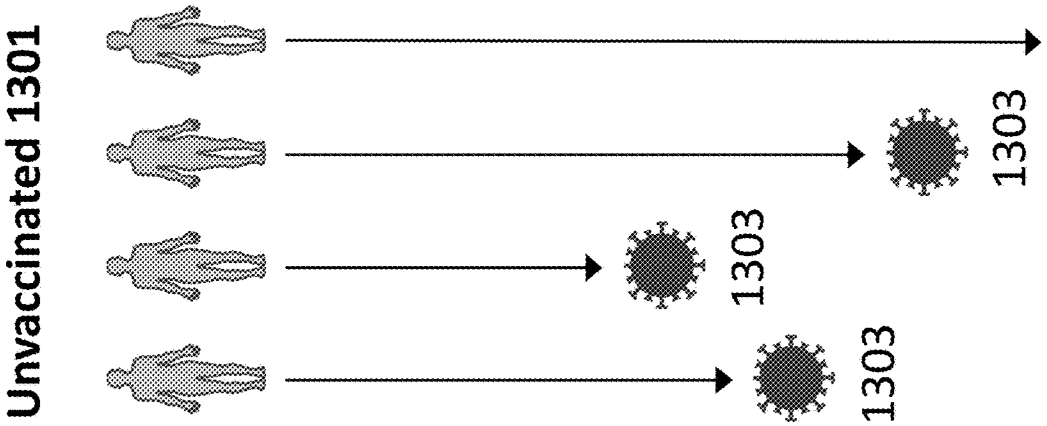
FIG. 13A shows a schematic of an unvaccinated cohort in a cohort study, according to certain embodiments.

In an exemplary cohort study, shown in FIGS. 13A-13B, the groups are defined by their exposure, e.g., vaccination status. FIG. 13A shows a cohort of unvaccinated individuals 1301 and FIG. 13B shows a cohort of vaccinated individuals 1302. The rate of an outcome, e.g., infection (indicated by an image of a virus 1303), is assessed between groups: How does the rate of the outcome differ based on the exposure? If the Unvaccinated Incidence Rate ($IR_{Vax}$) is 3 cases per 700 person-days and the Vaccinated Incidence Rate ($IR_{Unvax}$), 1 case per 900 person-days, the vaccine effectiveness (VE) can be calculated as shown below:

$$\text{Vaccine Effectiveness } (VE) = 1 - \text{Incidence Rate Ratio} = 1 - (IR_{Vas}/IR_{Unvax})$$

$$VE = 1 - ([1/900]/[3/700])$$

$$VE = 74\%$$

Figure 14B:
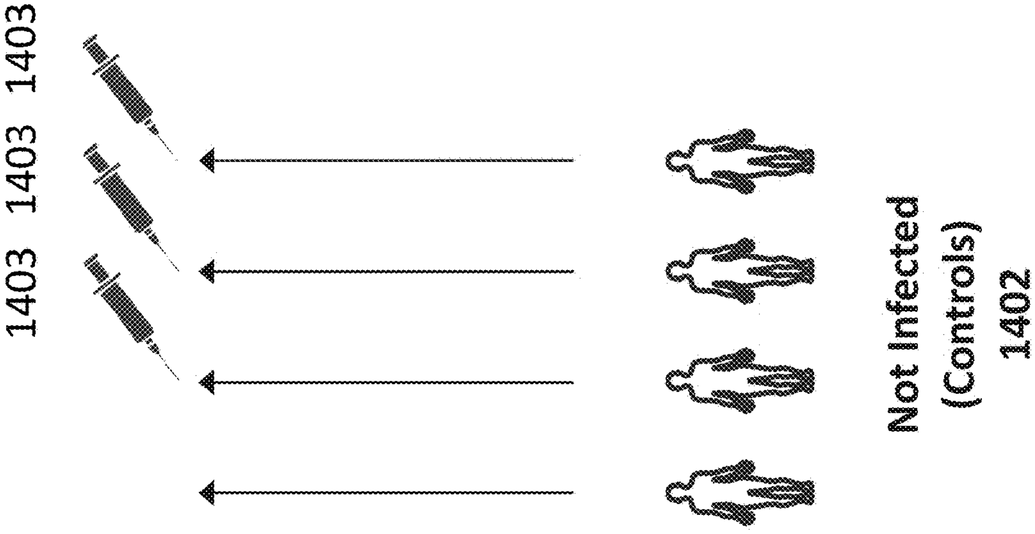
FIG. 14B shows a schematic of uninfected controls in a case-control study, according to certain embodiments.
Figure 14A:
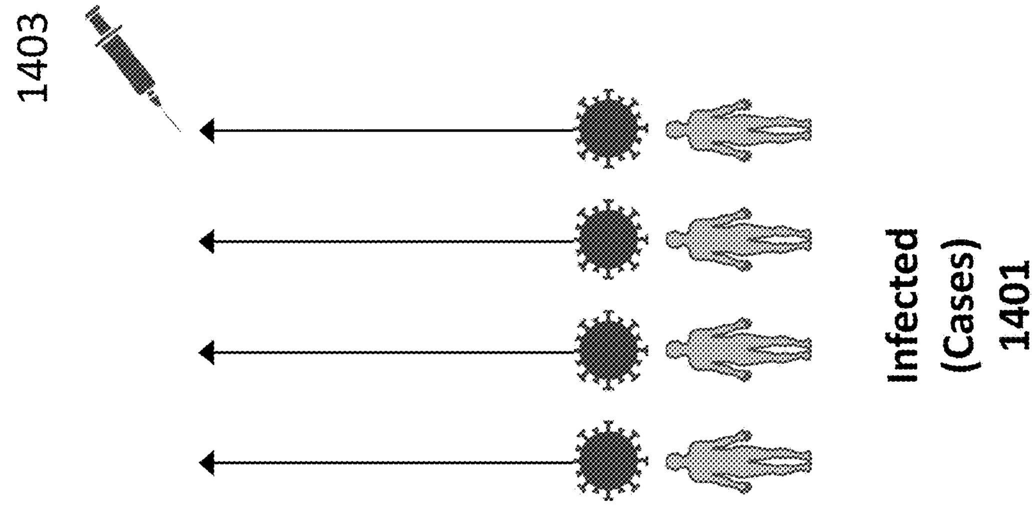
FIG. 14A shows a schematic of infected cases in a case-control study, according to certain embodiments.

In an exemplary case-control-study, shown in FIGS. 14A-14B, groups are defined by their outcome, e.g., infection status. FIG. 14A shows infected individuals 1401 (cases) and FIG. 14B shows uninfected individuals 1402 (controls). The rate of an exposure, e.g., vaccination status (indicated by an image of a syringe 1403) is assessed between groups: What are the odds of being a case for exposed versus non-exposed people? The Odds Ratio and Vaccine Effectiveness (VE) can be calculated for a case-control study as shown below:

$$\text{Odds Ratio} = (CaseVax/ControlsVax)/(CasesUnvax/ControlsUnvax)$$

$$VE = 1 - \text{Odds Ratio}$$

In the exemplary case-control study shown in Table 1, VE is 89%:

$$VE = 1 - ([1/3]/[3/1]) - 1 - 0.11 = 89\%$$

TABLE 1

Exemplary results of a case-control study

| | Infected | Not Infected |
|---|---|---|
| Vaccinated | 1 | 3 |
| Unvaccinated | 3 | 1 |

Figure 15A:
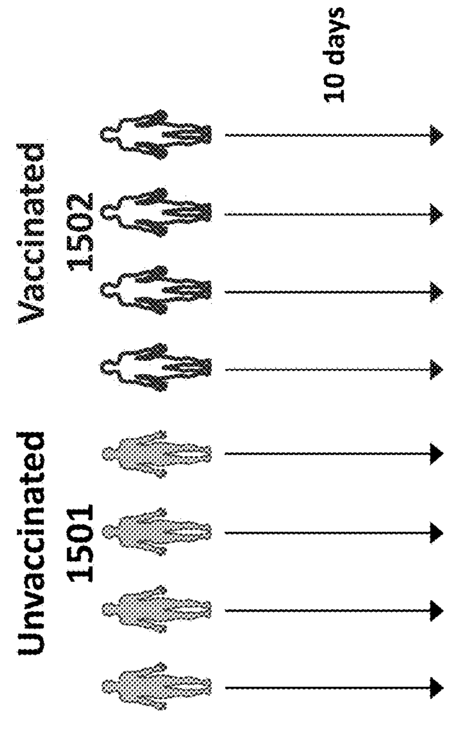
FIG. 15A shows a schematic of cohorts during the first ten days of a crossover cohort study, according to certain embodiments.
Figure 15B:
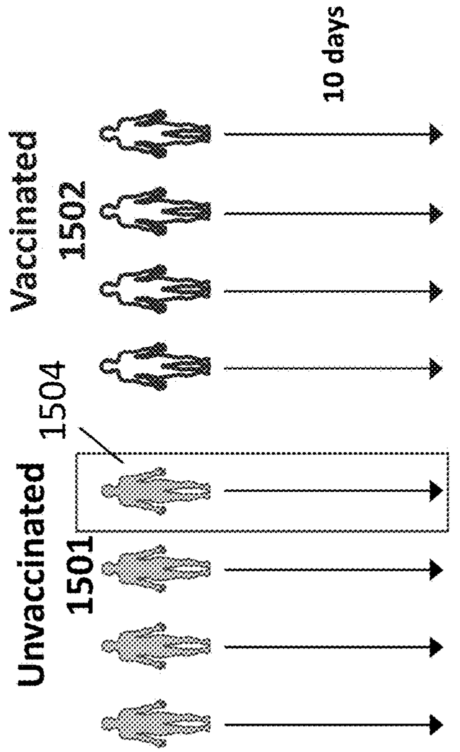
FIG. 15B shows a schematic of cohorts at day ten of a crossover cohort study when an individual in the unvaccinated cohort gets vaccinated, according to certain embodiments.
Figure 15C:
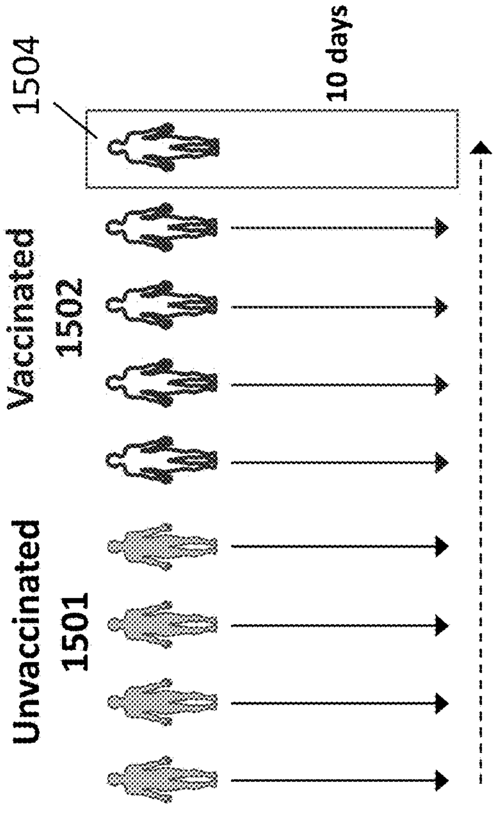
FIG. 15C shows a schematic of cohorts in a crossover cohort study after the individual crosses over, according to certain embodiments.
Figure 15D:
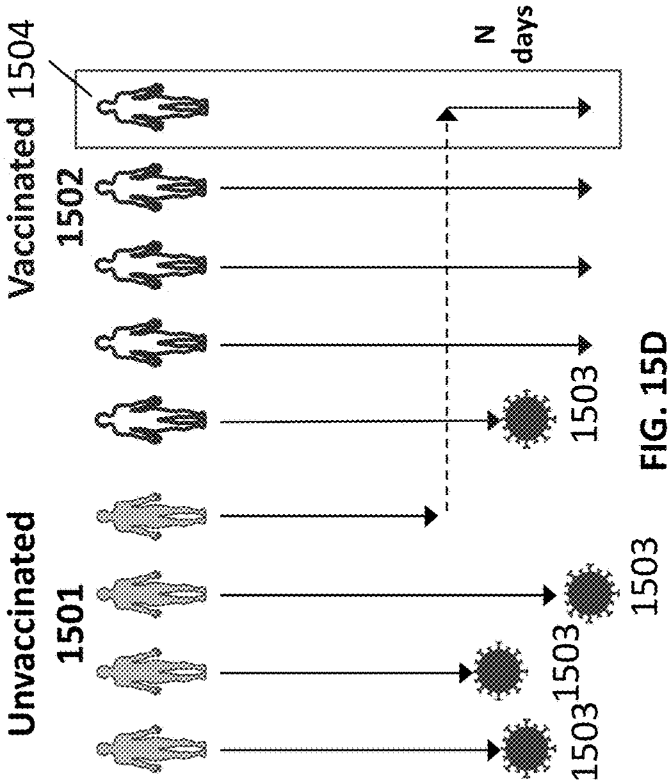
FIG. 15D shows a schematic of cohorts in a crossover cohort study for the remainder of the study, according to certain embodiments.

In some embodiments, a cohort study is a crossover study which allows people to contribute their at-risk time to the unvaccinated cohort until they become vaccinated and then contribute their at-risk time to vaccinated cohort. FIGS. 15A-15D show an exemplary crossover cohort study with four unvaccinated individuals (unvaccinated cohort) 1501 and four vaccinated individuals (vaccinated cohort) 1502. FIG. 15A shows the cohorts during the first ten days of the study, during which none of the individuals are infected. FIG. 15B shows the cohorts at day 10, when one individual 1504 in the unvaccinated cohort 1501 gets vaccinated. As shown in FIG. 15C, this individual 1504 crosses over to the vaccinated cohort 1502. FIG. 15D shows the cohorts after N days, after which some of the individuals are infected, indicated by the virus 1503. The individual 1504 contributes the days before vaccination (days 1 to 10) to the unvaccinated cohort 1501 and the days after vaccination (days 10 to N) to the vaccinated cohort 1502.

In some embodiments, a crossover design is beneficial because such a study avoids "looking into the future" during selection of participants. For example, if an individual is vaccinated at day 0, a matched unvaccinated individual is selected for the unvaccinated cohort. However, if the matched individual subsequently becomes vaccinated, the matched individual would be excluded in a non-crossover study because of the subsequent vaccination. The study designers have looked to the future in determining whether the match is valid. In contrast, in a crossover design, the match is valid, and the match would be moved from the unvaccinated cohort to the vaccinated cohort on the date of vaccination.

Figure 16:
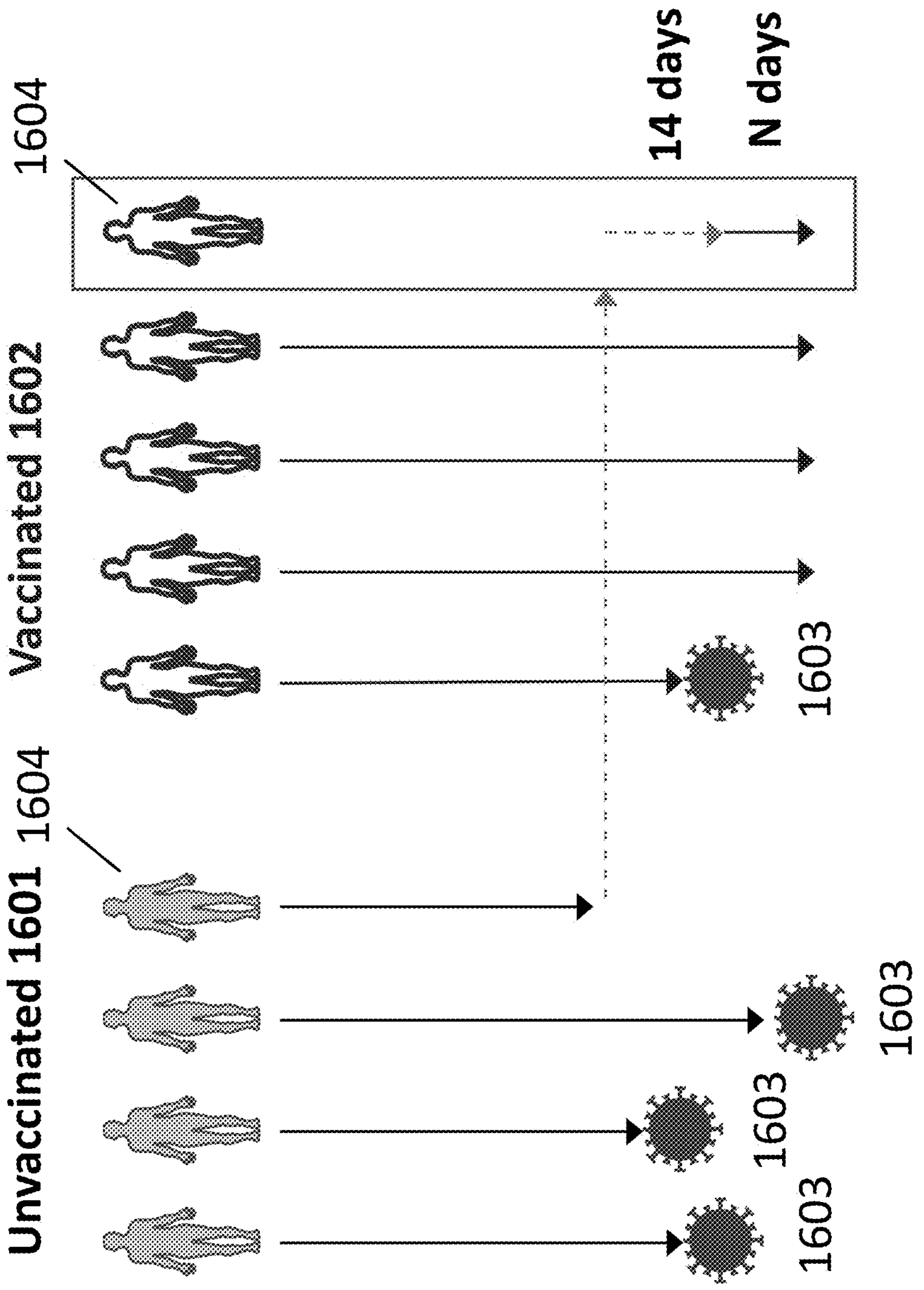
FIG. 16 shows a schematic of dynamic cohorts, according to certain embodiments.

In some embodiments, a cohort study uses a dynamic cohort, which is like a crossover study but includes a "buffer" during the interval in which the vaccine is not yet fully effective. In embodiments using a dynamic cohort, an individual does not contribute at-risk time to any group between the first dose and the date of full vaccination. FIG. 16 shows an exemplary dynamic cohort study. This study includes an unvaccinated cohort 1601 and a vaccinated cohort 1602. Infected individuals are indicated by an image of a virus 1603. During the study, individual 1604 from the unvaccinated cohort 1601 becomes vaccinated and crosses over to the vaccinated cohort 1602. However, the individual 1604 does not contribute at-risk time for a period of time after vaccination. In some embodiments, the vaccine is not fully effective immediately after vaccination and an infection may have occurred prior to crossing over, but not identified by symptoms and diagnosis until after vaccination. In some embodiments, shown in FIG. 16, vaccine effectiveness is not expected to set in for two weeks, and the period of time is 14 days. In FIG. 16, individual 1604 contributes its at-risk time to the unvaccinated cohort 1601 until vaccination, then contributes its at-risk time to neither cohort for 14 days, then contributes remaining time to the vaccinated cohort 1602

In some embodiments, the selection of cohort itself provides a proxy for unvaccinated patients by using the first few days of the 'vaccinated patients' as an unvaccinated cohort.

Figure 17:
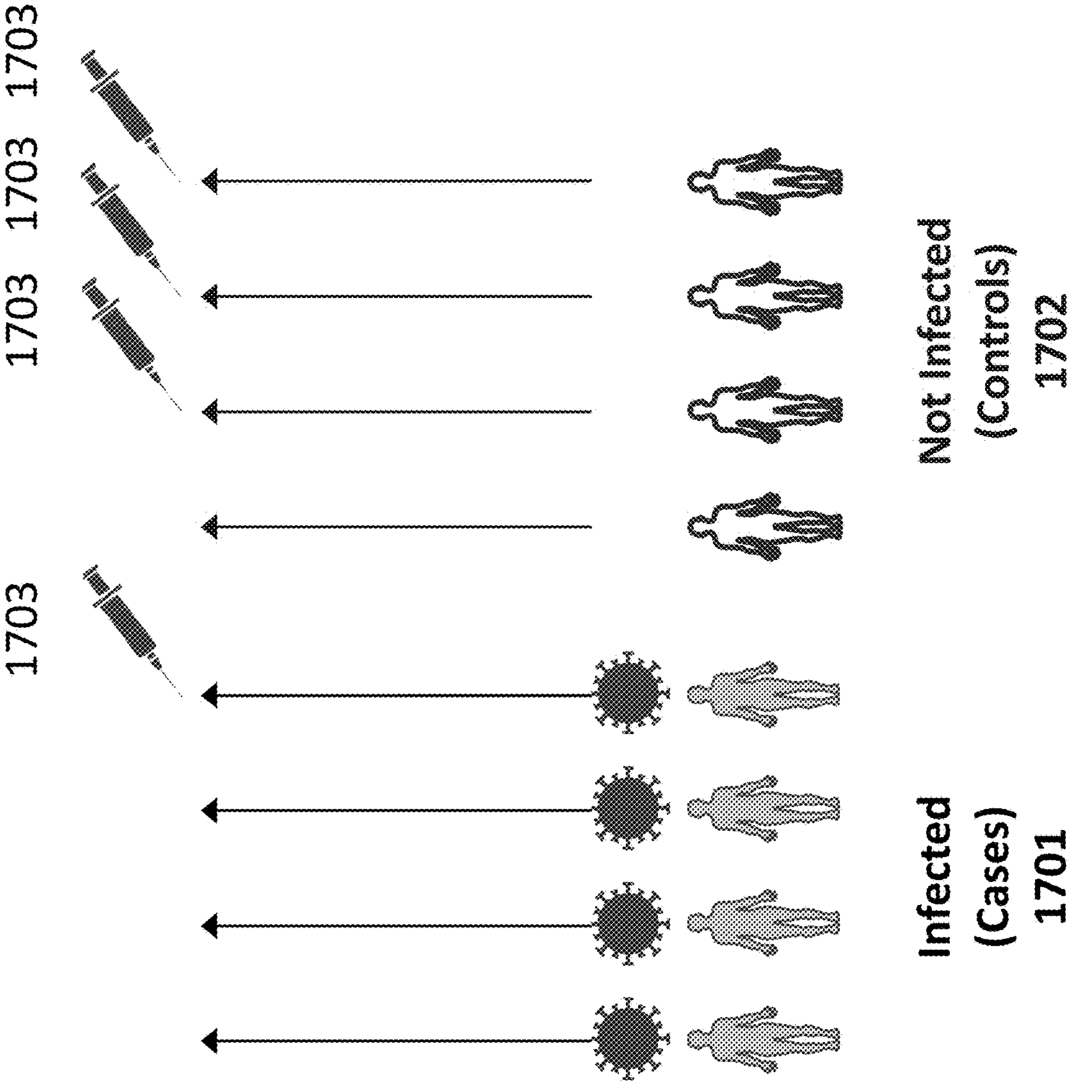
FIG. 17 shows a schematic of a test-negative study, according to certain embodiments.

In some embodiments, a case-control study is a test-negative study where case and controls presented with COVID-19 symptoms AND were tested (e.g. by PCR) for SARS-CoV-2 infection. FIG. 17 shows an exemplary test-negative study where cases 1701 are positive COVID tests, and controls 1702 are negative COVID tests. In some embodiments, one individual contributes multiple negative tests and therefore contributes multiple controls. However, in this exemplary test-negative study, all cases and controls presented to the clinic with symptoms and were tested for COVID-19. In some embodiments, such a test-negative study accounts for differences in healthcare-seeking behavior.

TABLE 2

Results for an exemplary test-negative study for COVID-19 vaccine effectiveness

| | Cases | Controls |
|---|---|---|
| Vaccinated | A | B |
| Unvaccinated | C | D |

Table 2 shows results for an exemplary test-negative study for COVID-19 vaccine effectiveness. Table 2, cases are positive PCR tests, and controls are negative PCR tests. For each case/control, the vaccination status is determined at the time of the test, and the odds are computed for being a case for vaccinated 1703 vs. unvaccinated individuals. The Odds Ratio and Vaccine Effectiveness are computed as shown below:

$$\text{Odds Ratio} = (A/B)/(C/D)$$

$$\text{Vaccine Effectiveness} = 1 - \text{Odds Ratio}$$

In this study, probability of being a case can be modeled as follows:

$$\text{logit}(p) \sim \text{Vaccination Status, where } p = \text{probability of being a case}$$

TABLE 3

| Results for an exemplary test-negative study for COVID-19 vaccine durability | | |
|---|---|---|
| | Cases | Controls |
| Distantly Vaccinated (e.g. >90 days ago) | A | B |
| Recently Vaccinated (e.g. last 30 days) | C | D |

Table 3 shows results for an exemplary test-negative study for COVID-19 vaccine durability. In Table 3, cases are positive PCR tests, and controls are negative PCR tests. For each case/control, the time since vaccination is determined at the time of test, and the odds of being a case for recently vaccinated vs. distantly vaccinated is computed. The Odds Ratio is computed as shown below:

$$\text{Odds Ratio} = (A/B)/(C/D)$$

In this study, if the Odds Ratio (OR) is greater than one, the odds of infection is higher for people who were vaccinated a long time ago is greater than for people who were recently vaccinated. In some embodiments, an OR greater than one indicates waning immunity. In this study, probability of being a case can be modeled as follows:

$$\text{logit}(p) \sim \text{Time Since Vaccination, where } p = \text{probability of being a case}$$

In some embodiments, cohort selection accounts for factors that could influence the odds of testing positive. In some embodiments, these factors are included as inputs to a model used to calculate an odds ratio.

In some embodiments, demographics influence odds of testing positive. Non-limiting examples of demographic factors include age, sex, race, ethnicity, income, and geography (e.g. continent, nation, state, county, city, borough, or zip code).

In some embodiments, clinical comorbidity influences odds of testing positive. Non-limiting examples of comorbidities include essential hypertension, hyperlipedemia, acute pharyngitis, otitis media, hypertension, type 2 diabetes mellitus, coronary atherosclerosis, upper respiratory tract infection, chronic kidney disease, and heart disease.

In some embodiments, geography influences odds of testing positive. For example, different geographic regions can have differences in COVID-19 incidence, masking policies, social distancing policies, or vaccine coverage. In some embodiments, geography data can include continent, nation, region, state, county, city, borough, or zip code. In some embodiments, a region is within a country, e.g., the Northeast, Southeast, South, Southwest, or Northwest of the United States.

In some embodiments, the time at which the test was taken influences odds of testing positive. For example, whether the test was taken during a spike in COVID-19 cases (e.g., during July or August 2021) or during a COVID variant's prevalence (e.g., during Alpha, Delta, or Omicron prevalence).

In some embodiments, the time at which the individual was vaccinated influences odds of testing positive. For example, potentially higher risk groups were vaccinated earlier. Non-limiting examples of high risk groups include individuals with occupational exposure, essential workers, individuals in long-term care facilities, older individuals, and individuals with comorbidities. For example, younger or healthier groups were vaccinated later. For example, there may be behavioral differences in the decision to become vaccinated over time.

In some embodiments, a health system can process input data using a regression model, e.g., a logistical regression model. For example, in an exemplary regression model, logit(p) is equal to the sum of Time Since Vaccination and one or more of Age, Sex, Race, Ethnicity, Comorbidities, Residential County, Date of Test, and Date of Vaccination, depending on the input data provided. In some embodiments, input to a regression model includes a vaccination status, a vaccination date, a test date, and a test result. In some embodiments, the input data can also include one or more of the demographic, comorbidity, and geographic data described above. In some embodiments, the date of the test and the date of vaccination define a primary exposure of interest: for example, time since vaccination=date of test–date of vaccination.

In some embodiments, a durability study design can be performed using test-negative approaches. In some embodiments, a regression can be stratified using any of the demographic information, comorbidity, or geographic information described above. In some embodiments, a regression can be stratified using time, e.g., date of test or date of vaccination. In some embodiments, the regression can be stratified using time based on a week, a two-week period, or a month. In a first exemplary approach, regression is stratified using county and date of test:

$$\text{logit}(p) \sim \text{Time Since Vaccination} + \text{Age} + \text{Sex} + \text{Race} + \text{Ethnicity} + \text{Comorbidities} + \text{Strata(Residential County, Date of Test)}$$

In a second exemplary approach, regression is stratified using county and date of vaccination:

$$\text{logit}(p) \sim \text{Time Since Vaccination} + \text{Age} + \text{Sex} + \text{Race} + \text{Ethnicity} + \text{Comorbidities} + \text{Strata(Residential County, Date of Vax)}$$

In both the first and second approaches, two analyses are performed. First, for fully vaccinated individuals, the odds of infection each day relative to the date of full vaccination is computed to approximate maximal protection. Second, for individuals with at least one dose, the odds of infection each day relative to four days after the first dose is computed to approximate the unvaccinated state.

In some embodiments, using a federated architecture system, a regression model can be fit to patient data for an individual health system, e.g., within a secure enclave of that system, and the output of that linear regression can be sent to a central node. In these embodiments, the central node can receive such output from a plurality of health systems and apply an aggregate analysis to that output data to provide an aggregate output, e.g., an odds ratio of infection aggregated over the plurality of health systems. For example, this aggregate output can be used as part of a sentinel system to determine vaccine effectiveness over time. In some embodiments, the regression model is a stratified model. In some embodiments, the regression model is a conditional logistical regression model. In some embodiments, the input data from each health system includes a vaccination status, a vaccination date, a test date, and test result. In some embodiments, the input data includes one or more other factors that may impact positivity rate, e.g., demographic data, comorbidities, or geographic data. In some embodiments, the output from each health system includes one or more parameters of the regression model, e.g., one or more regression coefficients, one or more standard errors of the one or more regression coefficient, or a value calculated from a combination thereof. In some embodiments the output from each health system can include a matrix of a regression model, e.g., a covariance matrix of a logistic regression model.

In some embodiments, a logistic regression can be applied to input data from a health system to produce estimates and confidence intervals for vaccine effectiveness. In some embodiments, a logistic regression is applied to input data within a secure enclave of the health system. In some embodiments, these estimates and confidence intervals can be sent to a central node that receives such outputs from a plurality of health systems and combines those outputs to provide an aggregate output. In one embodiment, a logistic regression can be applied to input data from a health system to produce estimates and confidence intervals for vaccine effectiveness for a number of time windows, each time window relative to some reference time window. In some embodiments, the reference time window is the date of vaccination or the date after vaccination when full immunity is reached (full vaccination). In some embodiments, the reference time window is the date of receiving a booster or a date after a booster when full immunity is reached, e.g., one month after a booster. For example, the input data can be from a COVID vaccine durability test-negative analysis (as discussed above in relation to FIG. 17).

For example, when evaluating change of vaccine efficacy relative to a reference time window of time of full vaccination (e.g., 2 doses+14 days), the aggregate covariate-adjusted odds of testing positive for covid is computed in each time window of interest (e.g. the time windows (i) 30-60 days following full vaccination, (ii) 60-90 days following full vaccination, (iii), 90-120 days following full vaccination, etc.) relative to a reference time window of 0-30 days following full vaccination (equivalent to the window 14-44 days following 2 doses).

In some embodiments, a covariate-adjusted odds ratio can be determined by fitting a regression model, e.g., a conditional logistic regression model, to the input data of each health system. In these embodiments, the input data for the regression model includes data for each time window of interest, where each individual test is bucketed into a time window and each individual's input data includes a binary covariate for each time window and the reference time window (1 if the test falls within the time window and 0 if the test falls outside the time window or if the test falls within the reference time window). This regression model can be applied to input data of a system within a secure enclave of that system. The regression model can produce, for each time window of interest w, an estimated regression coefficient $\hat{\beta}_w$, along with an estimated standard error $SE_{\beta_w}$. In this example, this regression coefficient is the estimated log odds of testing positive in time window w relative to testing positive in the reference time window in that system (where log is natural log). An estimate of the odds is the exponential of this coefficient, e.g. $\exp(\hat{\beta}_w)$. For example, if $\exp(\hat{\beta}_w)=2$, it is estimated that an individual is 2× less protected (2× more likely to get covid on exposure) in window w than the reference time window. A 95% confidence interval around this quantity can be given by [$\exp(\hat{\beta}_w-1.96\ SE_{\beta_w})$, $\exp(\hat{\beta}_w+1.96\ SE_{\beta_w})$]. In some embodiments, the input data includes demographic data, comorbidity data, or geographic, and the regression model can also produce a regression coefficient corresponding to each demographic, comorbidity, or geographic parameter, where each coefficient reflects all time windows. In some embodiments, the regression model is stratified by one or more demographic, comorbidity, or geographic parameters. In these embodiments, a stratified parameter does not have an associated coefficient.

Assumptions required for this interpretation to hold (in the slightly different context of using a test-negative design to estimate vaccine effectiveness) include that decision to vaccinate is not correlated to exposure or susceptibility and that a vaccine confers all-or-nothing protection.

In some embodiments, such a regression analysis can be run on each of a plurality of health systems, e.g., within a secure enclave for each health system, and aggregated, e.g., by a central node. One exemplary method to combine the estimates for each health system is to apply a standard inverse-variance weighting meta-analysis procedure, described herein. First, each system is denoted by superscript (1), (2), etc: so the coefficient/standard error estimates are $$\hat{\beta}_w^{(1)}, SE_{\beta_w}^{(1)}, \hat{\beta}_w^{(2)}, SE_{\beta_w}^{(2)}.$$

In this way, a central node can calculate an aggregate output using output data from each health system (e.g., regression coefficients and standard error estimates) that is aggregated for each hospital systema and does not include personally identifiable information.

To calculate a standard inverse-variance weighting analysis, the following summations are made over all health systems j. For each time window w the following are computed:

$$\text{Combined coefficient estimate:}\hat{\beta}_{w,combined} = \sum_j \frac{1}{\left(SE_{\beta_w}^{(j)}\right)^2}\hat{\beta}_w^{(j)}$$

$$\text{Combined standard error estimate:}SE_{\beta_w,combined} = \frac{1}{\sum_j \frac{1}{\left(SE_{\beta_w}^{(j)}\right)^2}}$$

These combined estimates can be used to give a combined or aggregated estimate of the protection from vaccine, along with 95% confidence interval during each window w:

$$\text{Estimated odds } \exp(\hat{\beta}_{w,combined})$$

$$95\%CI: \begin{bmatrix} \exp(\hat{\beta}_{w,combined} - 1.96SE_{\beta_{w,combined}}), \\ \exp(\hat{\beta}_{w,combined} + 1.96SE_{\beta_{w,combined}}) \end{bmatrix}$$

In some embodiments, this method assumes that the health systems providing regression coefficients are estimating the same underlying true parameter values $\beta_w$. For example, this method assumes that the regression model has accounted for systemic biases, e.g., demographics (e.g., age, sex, race, ethnicity), comorbidities, or geography. In some embodiments, the possibility of additional systemic difference in treatment effect (e.g., an effect that isn't adjusted for by the covariate adjustments in the regression model) can be handled by applying the Der-Simonian-Laird meta-analysis approach for handling possible heterogeneity in effects. The formulas for this method are contained also in Borenstein M, Hedges L V, Higgins J P T, Rothstein H R. A basic introduction to fixed-effect and random-effects models for meta-analysis. Res Synth Methods. 2010; 1: 97-111. For example, a between-study or between-system variance $\tau^2$ can be estimated by computing the amount of study-to-study or system-to-system variation actually observed, estimating how much the observed effects would be expected to vary from each other if the true effect were actually the same across studies, and assuming that excess variation reflects real differences in effect size. In this example, $\tau^2$ can be estimated using the following equations:

$$\tau^2 = \frac{A - df}{C} \text{ where } Q = \sum_{i=1}^{k} W_i (Y_i - M)^2 = \sum_{i=1}^{k} \frac{(Y_i - M)^2}{V_i},$$

$$df = k - 1,$$

k is the number of studies (or health systems), and $$C = \sum W_i - \frac{\sum W_i^2}{\sum W_i}$$

The statistic Q is a (weighted) sum of squares of the effect size estimates ($Y_i$) about their mean (M). Q is weighted in such a manner that assigns more weight to larger studies, and this also puts Q on a standardized metric. In this metric, the expected value of Q if all studies share a common effect size is df. Therefore, Q–df represents the excess variation between studies, that is, the part that exceeds what we would expect based on sampling error. Since Q–df is on a standardized scale, we divide by a factor, C, which puts this index back into the same metric that had been used to report the within-study variance, and this value is $\tau^2$. If $\tau^2$ is less than zero, it is set to zero, since a variance cannot be negative. These methods can also be run using the function statsmodels.stats.meta_analysis.combine_effects in the python statsmodels package. See Seabold S, Perktold J. Statsmodels: Econometric and Statistical Modeling with Python. Proceedings of the 9th Python in Science Conference. 2010. pp. 92-96.

In one embodiment, the central node can fit output data from a plurality of health systems to an aggregate regression model across the plurality of health systems. In this embodiment, the output data of each health system can include all regression coefficients and associated standard errors of the regression model of that health system or the output data of each health system or the output data can include one or more regression coefficients from each healthcare system that are stratified by one or more demographic factors. In this embodiment, the output of each health system can also include the coefficient covariance matrix, for example, if providing a continuous estimate over time, as discussed in further detail below. In other embodiments, the output data of each health system can include all patient data and a regression is performed a the central node.

Figure 18A:
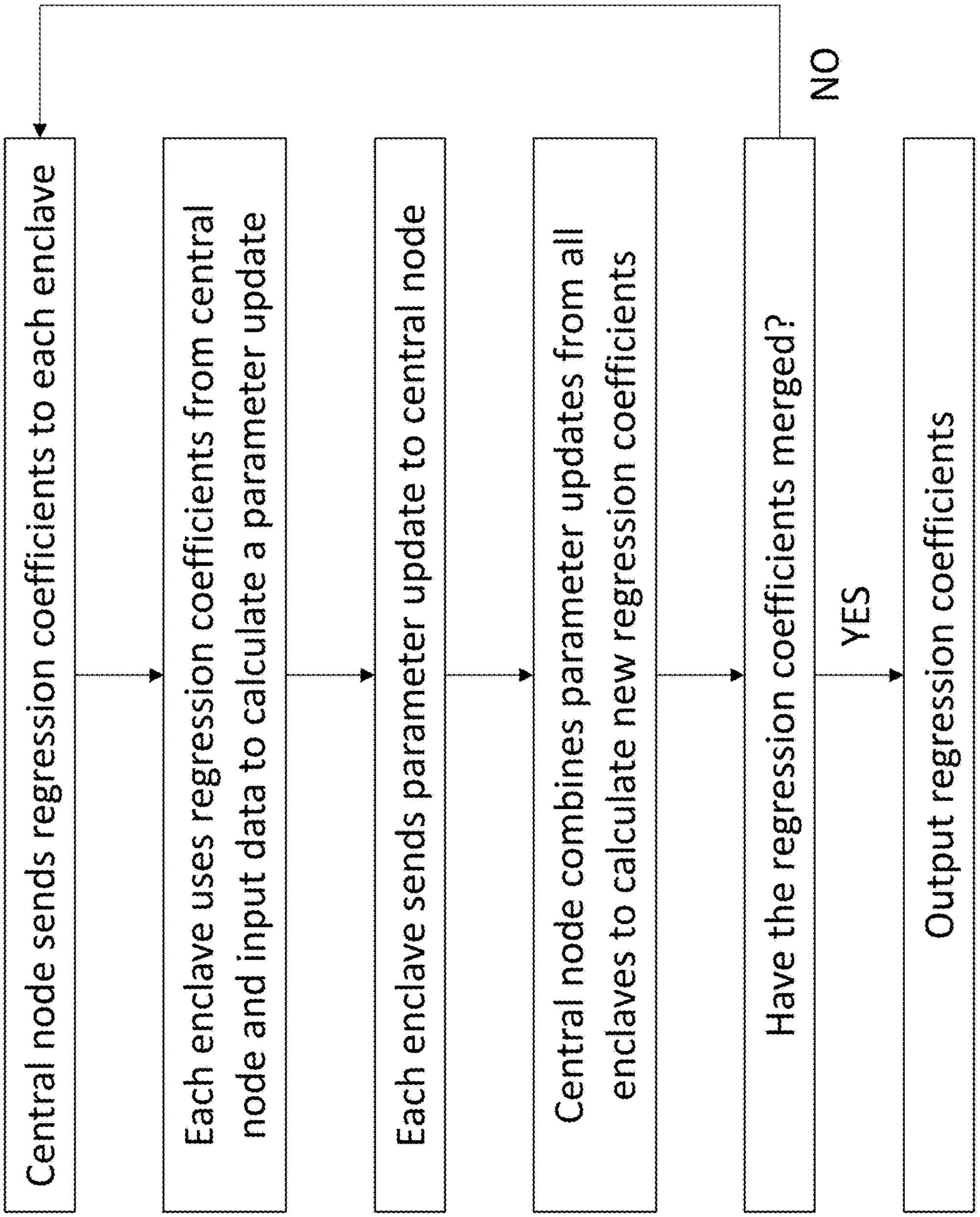
FIG. 18A shows a process for iteratively calculating an aggregate regression, according to certain embodiments.

In some embodiments, fitting of the aggregate model can be done in an iterative fashion, e.g., by gradient descent to fine tune the aggregate model. For example, as shown in FIG. 18A, the following steps can be looped to fit the aggregate regression model: (i) the central node sends all regression coefficients of the aggregate regression model (including regression coefficients corresponding to the log (odds) for each time window) to an enclave 1802 in each health system; (ii) the enclave in each health system uses(a) the regression coefficients received from the central node and (b) the input data of the health system to compute (c) a parameter update (e.g., a gradient computed by taking partial derivatives of a conditional logistic regression likelihood) for each regression coefficient; (iii) the central node receives the parameter updates from each secure enclave and combines the "parameter updates" for each parameter (e.g., in the case of gradient, by summing up the gradient from each system), and then performs a single "parameter update" (e.g., in the case of gradient descent, by applying some multiple of the sum of gradients) to get a new set of regression coefficients. In some embodiments, the aggregate regression coefficients are initialized to some values at the central node (for example, using some random small numbers—e.g. a normal distribution with zero mean and small standard deviation). In some embodiments, the update parameters include parameters of an optimization algorithm, e.g., a gradient descent or limited memory Broyden-Fletcher-Goldfarb-Shanno algorithm. In some embodiments, these steps are repeated until the parameters or regression coefficients converge. For example, after the central node receives the update parameters, the central node computes a new set of regression coefficients, and the parameters are considered to converge when the difference (e.g., the sum absolute difference) between the prior regression coefficients and the new regression coefficients is sufficiently small. In another example, the parameters are considered to converge when the update parameters (e.g., gradients) are sufficiently small.

Figure 18B:
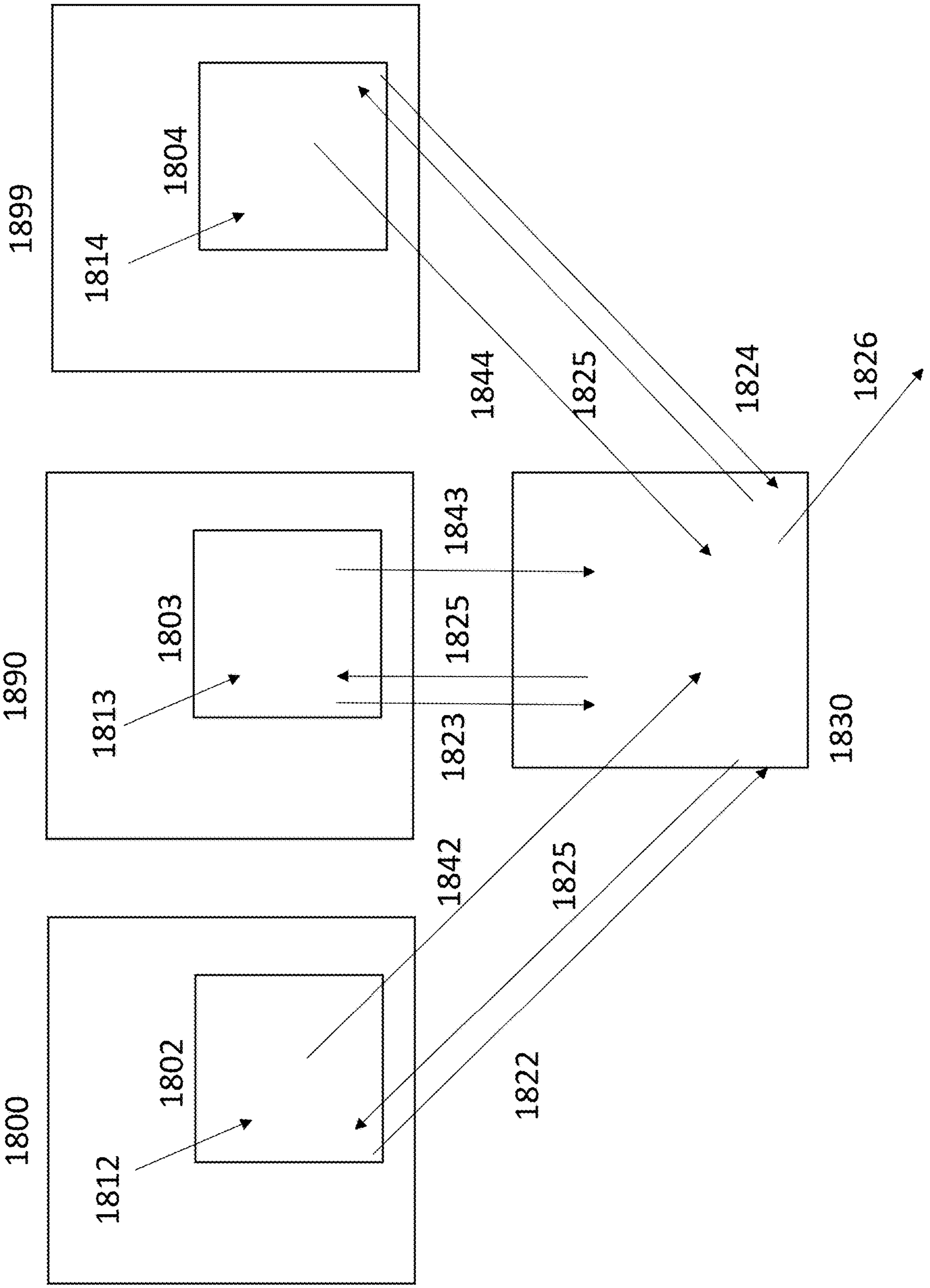
FIG. 18B shows a simplified diagram of an architecture of a central node that calculates an aggregate regression, according to certain embodiments.

An exemplary aggregate regression embodiment is shown in FIG. 18B. In this embodiment, a secure enclave 1802, 1803, 1804 in each health system 1800, 1890, 1899 receives input data 1812, 1813, 1814, and software within each secure enclave fits the input data to provide output data 1822, 1823, 1824. This output data is sent to a central node 1830, which fits this output data to an aggregate regression model. The central node then sends aggregate regression coefficients 1825 for the aggregate model back to the enclave of each health system. Each health system then applies the aggregate regression coefficients 1825 to its respective input data and provides update parameters 1842, 1843, 1844. The central node then fine-tunes the aggregate regression model using the update parameters and sends updated aggregate regression coefficients back to the secure enclaves of each health system. This process of iteratively tuning the aggregate regression model can be repeated until the update parameters converge, and then fine-tunned aggregate regression coefficients 1826 are output from the central node.

In one embodiment, the central node can provide a continuous estimate of vaccine durability over time, as an alternative to providing estimates only at specific time windows relative to a reference window. In some embodiments, the number of time windows can be limited by the number of parameters that can be fit based on the sample size. In these embodiments, a day-by-day change can be calculated using interpolation (e.g., a spline), without increasing the number of time windows or parameters to be fit. In some embodiments, the number of time windows can be limited by the sample size during a particular time period.

In these embodiments, if each time window is short, there can be a small number or tests in each time window and the data can be noisy.

For example, to provide a continuous estimate of vaccine durability over time, within each health system, as discussed above, a regression model can produce, for each time window of interest w, an estimated regression coefficient $\hat{\beta}_w$, along with an estimated standard error $SE_{\hat{\beta}_w}$. Within each health system, an estimated regression coefficient and estimated standard error can be calculated for time points between each time window (e.g., for each day) by interpolation, with each time window acting as a breakpoint. For example, a linear spline or a cubic spline can be used to estimate the regression coefficient and estimated standard error continuously between each time window or breakpoint. In one example, for vaccine durability following time of full vaccination, the spline breakpoints (windows of interest) were at every 50 days since time of full vaccination. After a regression model within a health system is fit, an estimate of the relative log odds of protection at each day d (i.e. odds of testing positive on day d relative to day of full vaccination), along with standard error can be derived. After running a regression analysis for each health system, each health system can send an estimate for each day to the central node. The central node can then combine the estimates across health systems to provide an aggregate output. For example, an aggregate output can be calculated using an inverse-variance weighting as described above. In another example, an aggregate regression model across the plurality of health systems can be calculated using the iterative method described above. In this example, a covariance matrix of regression coefficients would be used to compute standard errors for splines.

EXAMPLES

Certain embodiments will now be described in the following non-limiting examples.

Figure 19:
FIG. 19 shows vaccinated patient data for patients vaccinated with the Pfizer and Moderna COVID-19 vaccines, according to certain embodiments.

FIG. 19 shows patient data from a health system. FIG. 19, Left hand panel (Cohort A) shows patient data for the Pfizer vaccine. FIG. 19, Right hand panel (Cohort B), shows patient data for the Moderna vaccine Out of approx. 259K patients who had the mRNA vaccines at this health system, 3.8K patients (less than 1.5%) had a breakthrough infection after full vaccination. The vaccine has been protective for over 98.5% of people.

Figure 20:
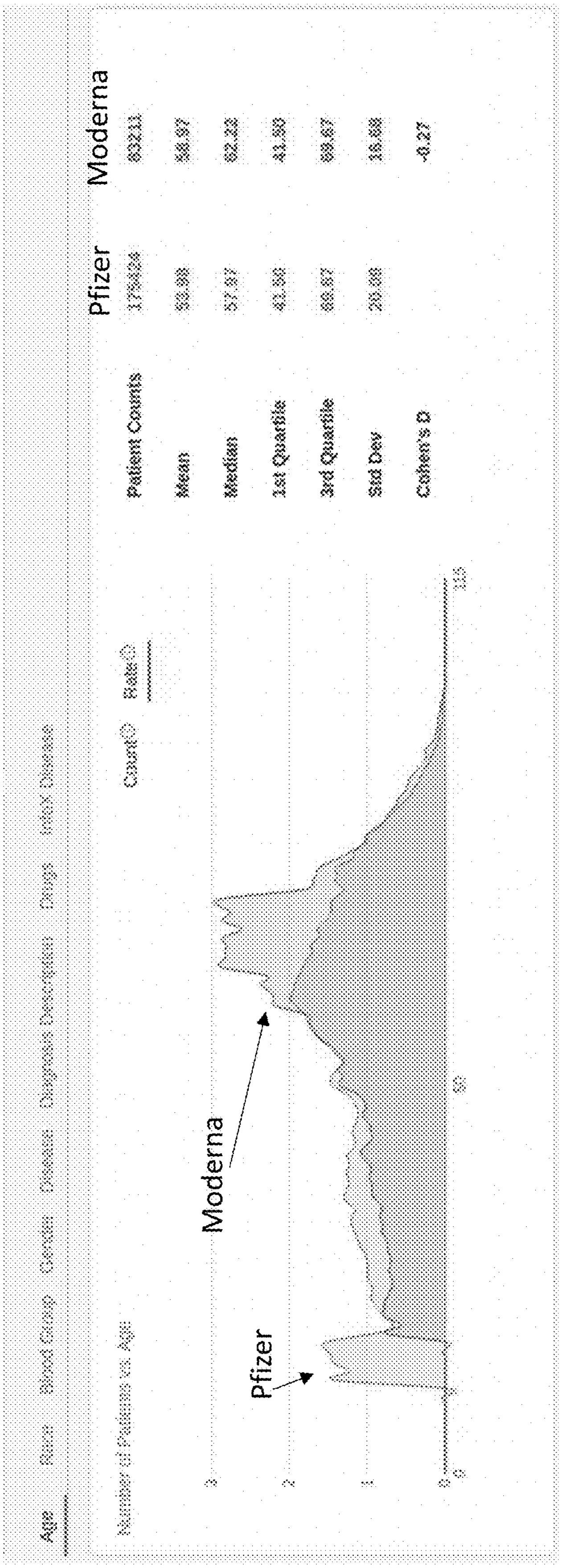
FIG. 20 shows age distribution in the Moderna and Pfizer cohorts, showing that the Moderna cohort is older than the Pfizer cohort, according to certain embodiments.

Both Pfizer and Moderna are highly effective, but Moderna is even more impressive given that, as shown in FIGS. 20 and 21, this health system's cohort that took Moderna vaccines are both older and sicker. Moderna cohort has higher co-morbidities such as Hypertension, Type 2 Diabetes etc.) than Pfizer cohort.

Figure 22:
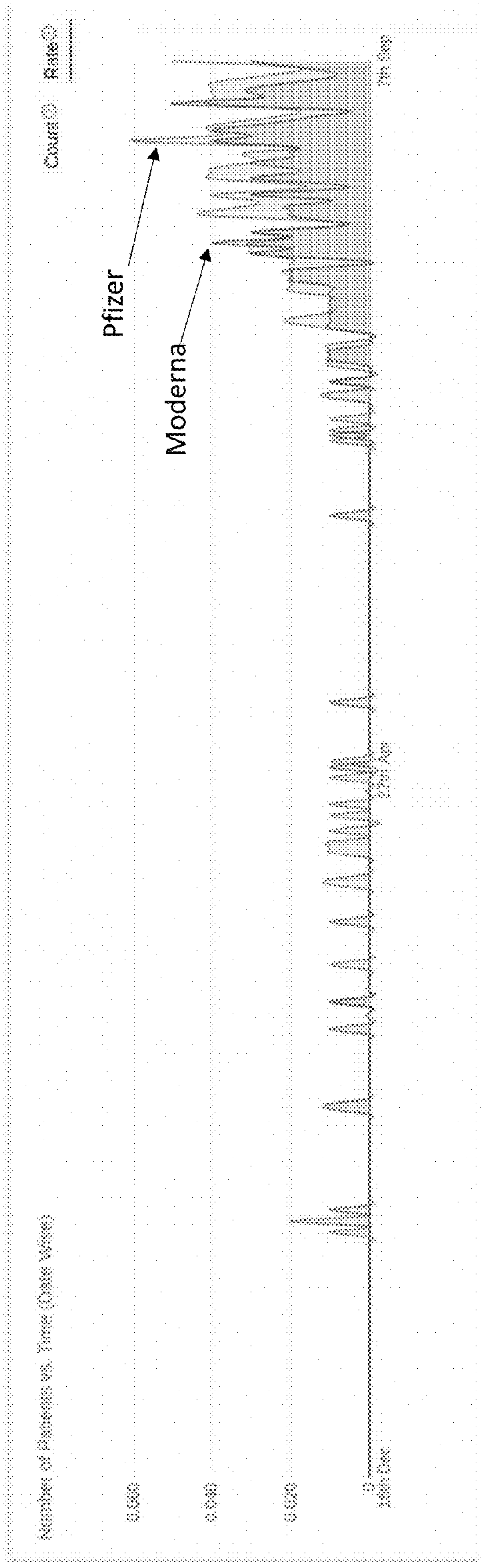
FIG. 22 shows the number of breakthrough cases over time in the Moderna and Pfizer cohorts, according to certain embodiments.

As shown in FIG. 22, the rate of breakthrough infections is inching up in recent weeks indicating waning vaccine effectiveness.

Figure 23:
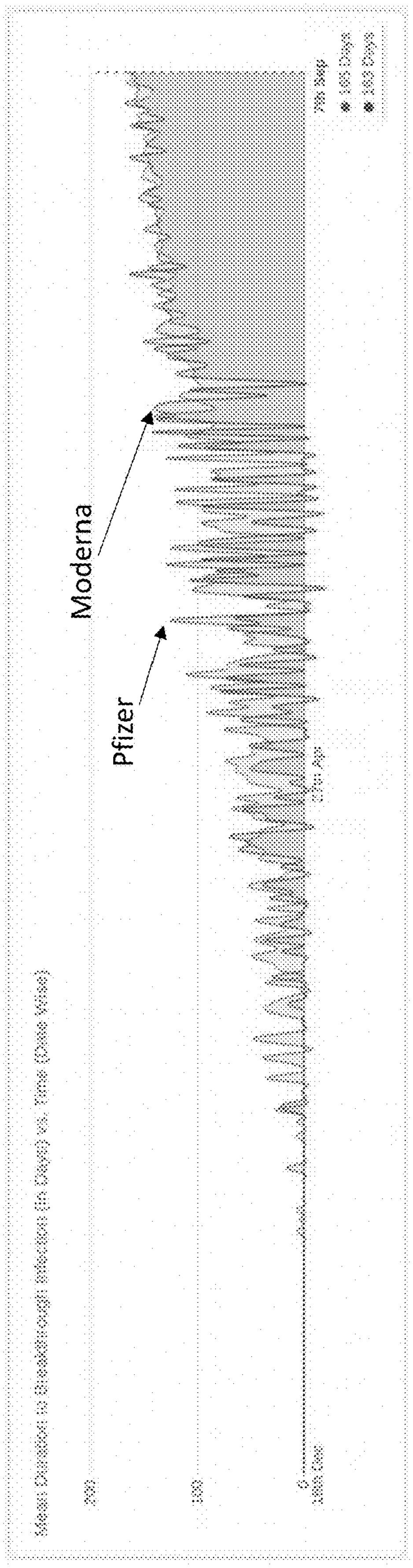
FIG. 23 shows mean duration to breakthrough (in days) vs. time (by date) in the Moderna and Pfizer cohorts, according to certain embodiments.

Yet, as shown in FIG. 23, the protection afforded by the vaccines (durability) is quite high and stabilizing—both Pfizer and Moderna vaccines show mean duration of close to 5.5 months of protection before a breakthrough infection.

Figure 24:
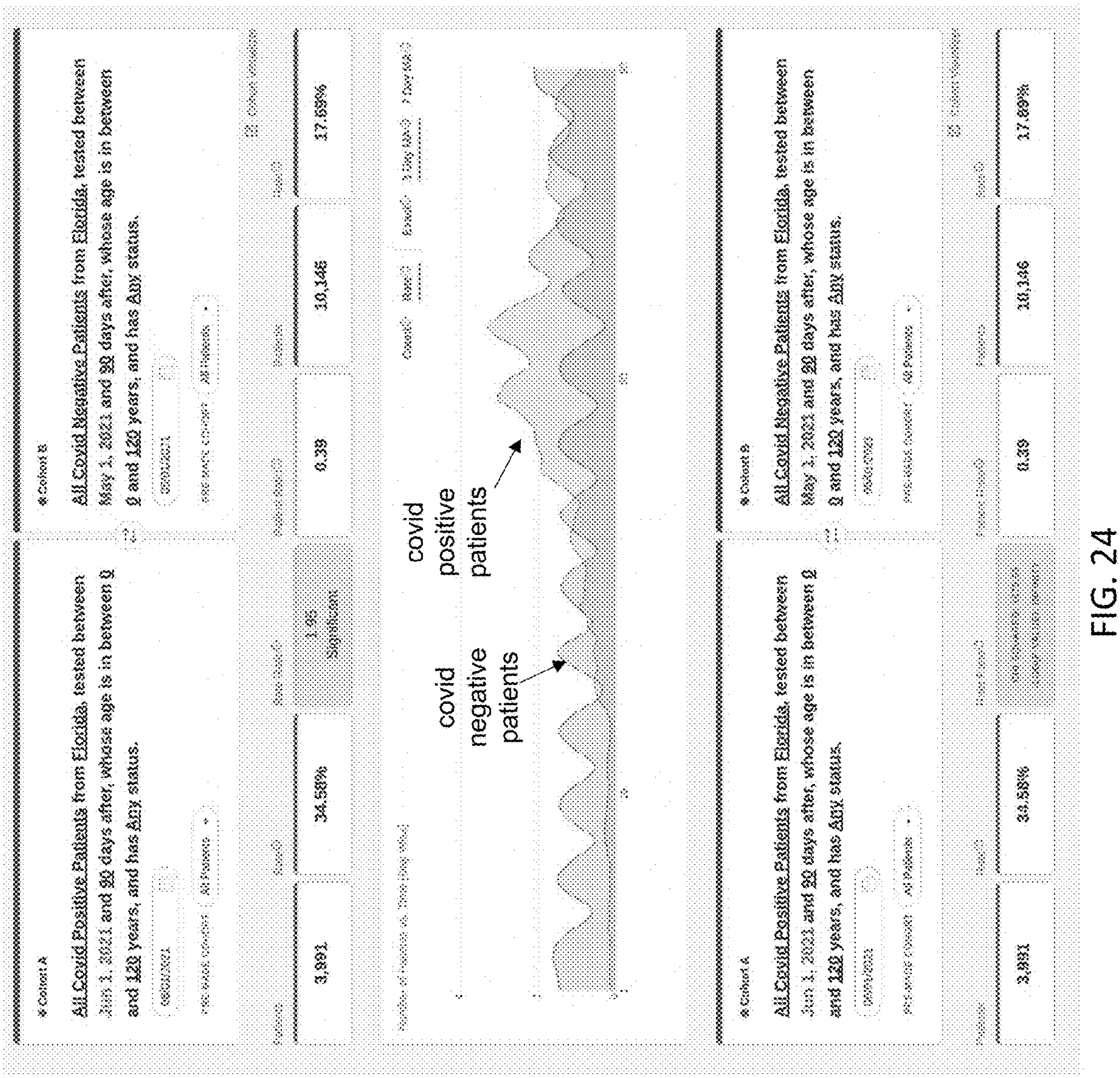
FIG. 24 shows a comparison of covid positive patients and covid negative patients over time in Florida, according to certain embodiments.

As shown in FIG. 24. comparison across time illustrates emergence of hotspots: See the hotspots (left panel) for COVID-19 positive patients in Florida in July '21 which subsequently settled in late August '21. The observation of COVID positive patients almost twice the rate (1.95 to be precise) of COVID negative patients is statistically significant with a Chi-square value of 1679 (which has a corresponding p-value that is so close to zero or negative log (pvalue) is infinity).

Figure 25:
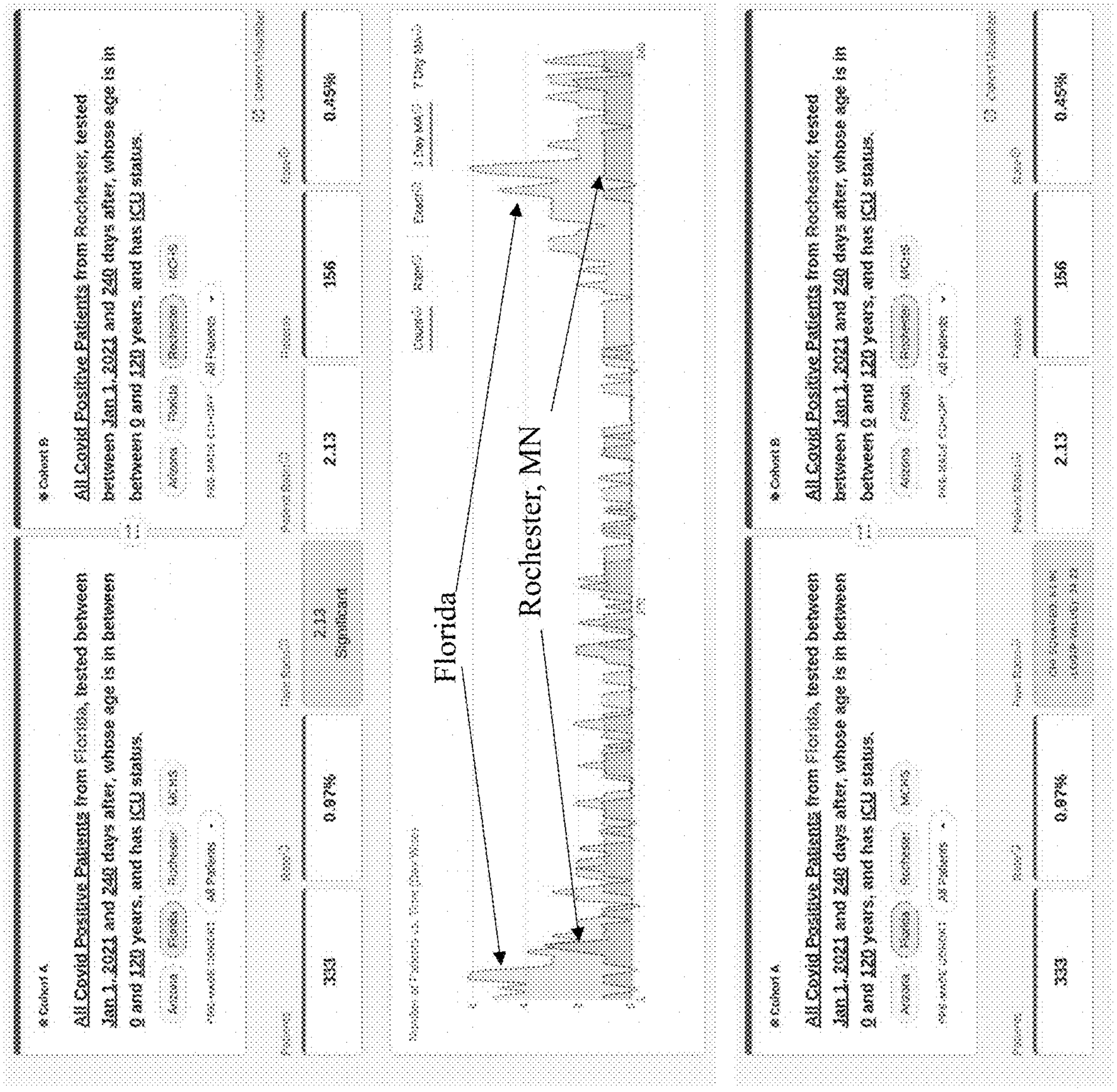
FIG. 25 shows the number of COVID-19 patients admitted to the ICU in Florida and Rochester, MN, according to certain embodiments.

As shown in FIG. 25, comparison across space illustrates stretching of Hospital resources amidst severe illness of COVID-19 patients (ICU admissions): See the Florida based COVID-19 patients admitted to the ICU for 8 months of 2021. The observation of increased admissions to ICU in Florida as compared to Rochester MN at almost twice the rate (2.13 to be precise) is statistically significant with a Chi-square value of 63.8 (which has a corresponding p-value=$10^{-34}$).

FIGS. 26-29 show results for a durability study performed using test-negative approaches. In this study, two analyses are performed. First, for fully vaccinated individuals, the odds of infection each day relative to the date of full vaccination is computed to approximate maximal protection. Second, for individuals with at least one dose, the odds of infection each day relative to four days after the first dose is computed to approximate the unvaccinated state.

Figure 26:
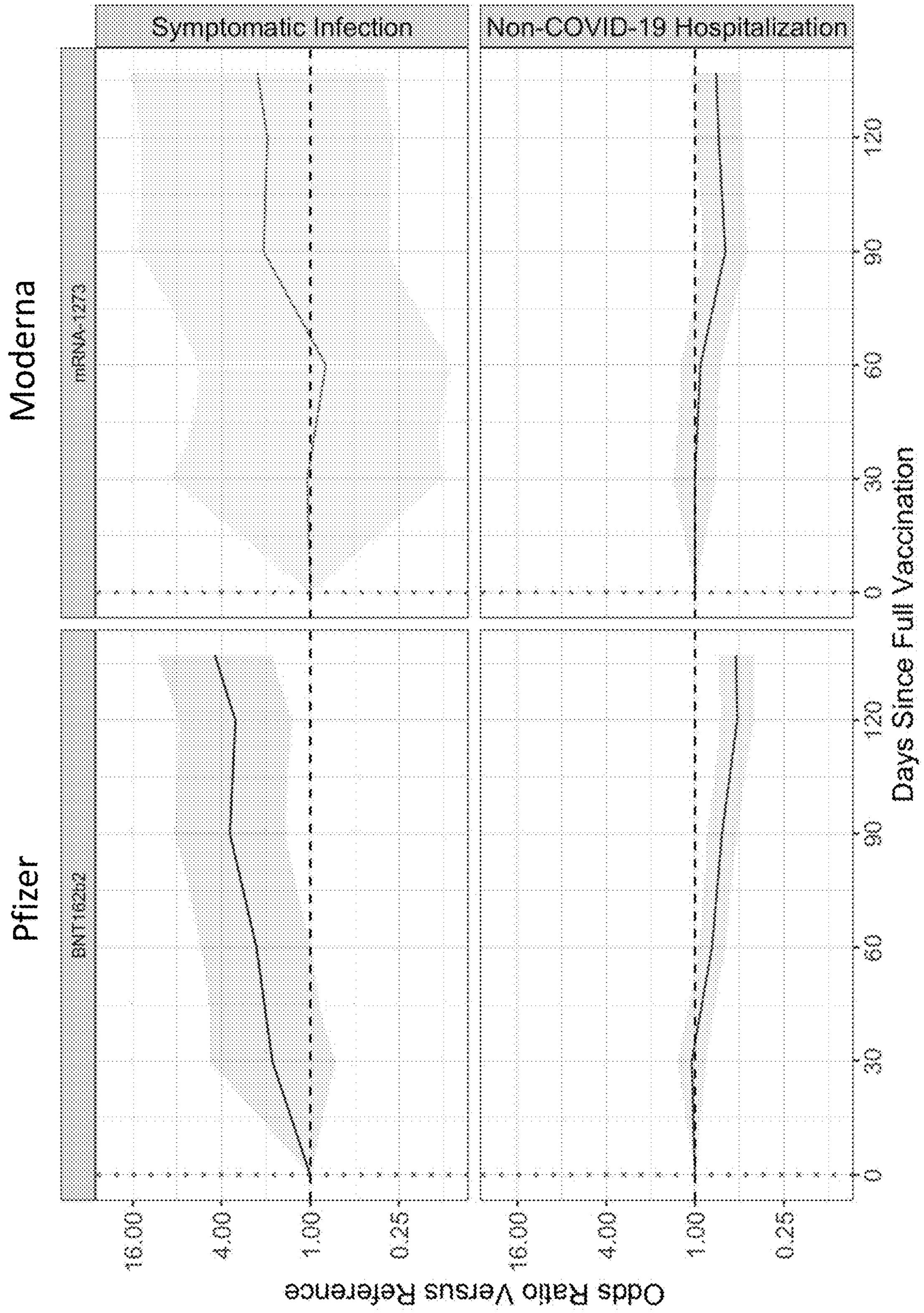
FIG. 26 shows the Odds Ratio of as a function of days since full vaccination, stratified by the date of testing, for symptomatic infection and non-COVID-19 hospitalization, according to certain embodiments.

FIG. 26 shows the Odds Ratio as a function of days since full vaccination, stratified by the date of testing, for symptomatic infection and non-COVID-19 hospitalizations.

Figure 27:
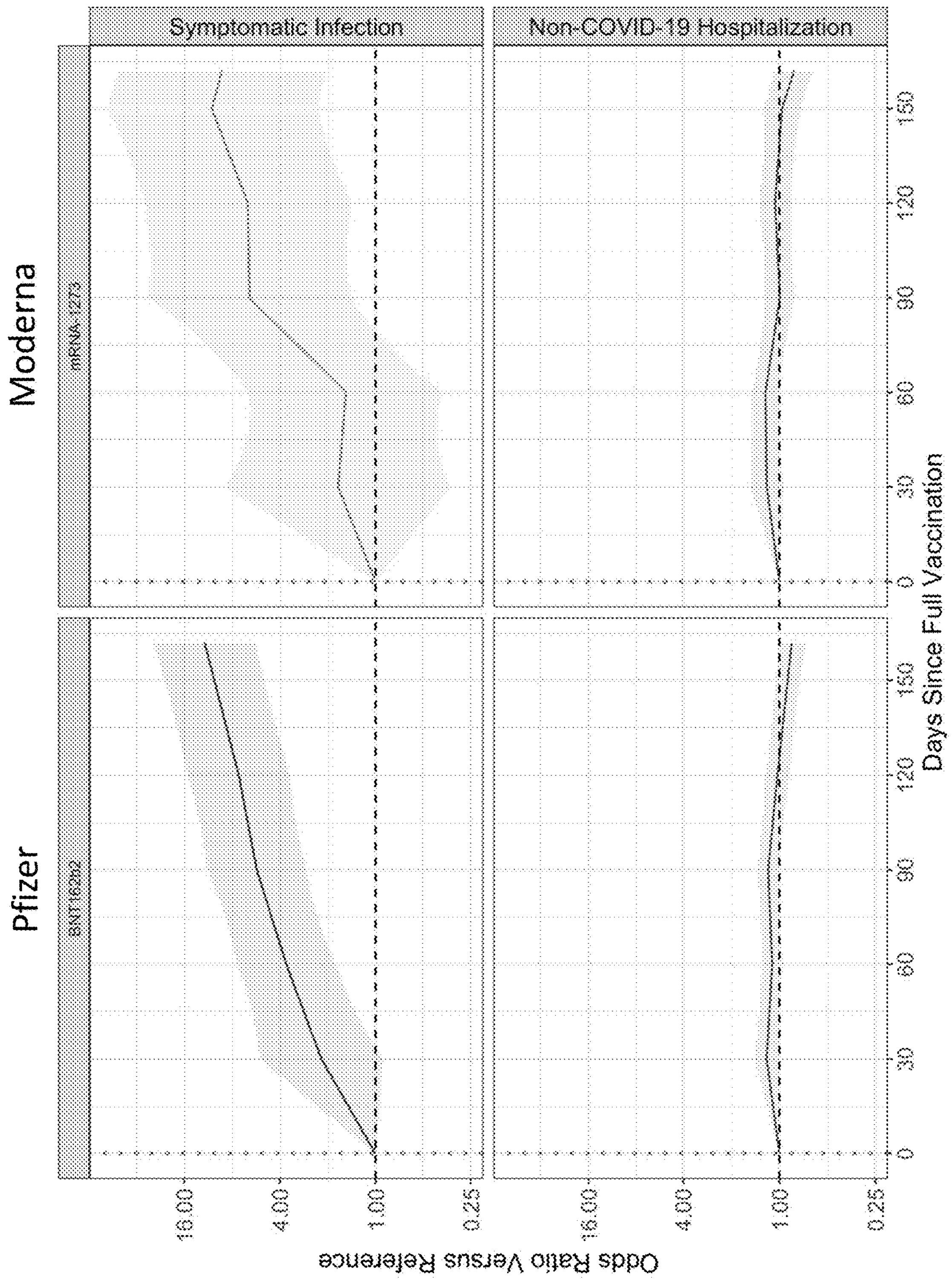
FIG. 27 shows the Odds Ratio as a function of days since full vaccination, stratified by the date of vaccination, for symptomatic infection and non-COVID-19 hospitalization, according to certain embodiments.

FIG. 27 shows the Odds Ratio as a function of days since full vaccination, stratified by the date of vaccination, for symptomatic infection and non-COVID-19 hospitalizations.

Figure 28:
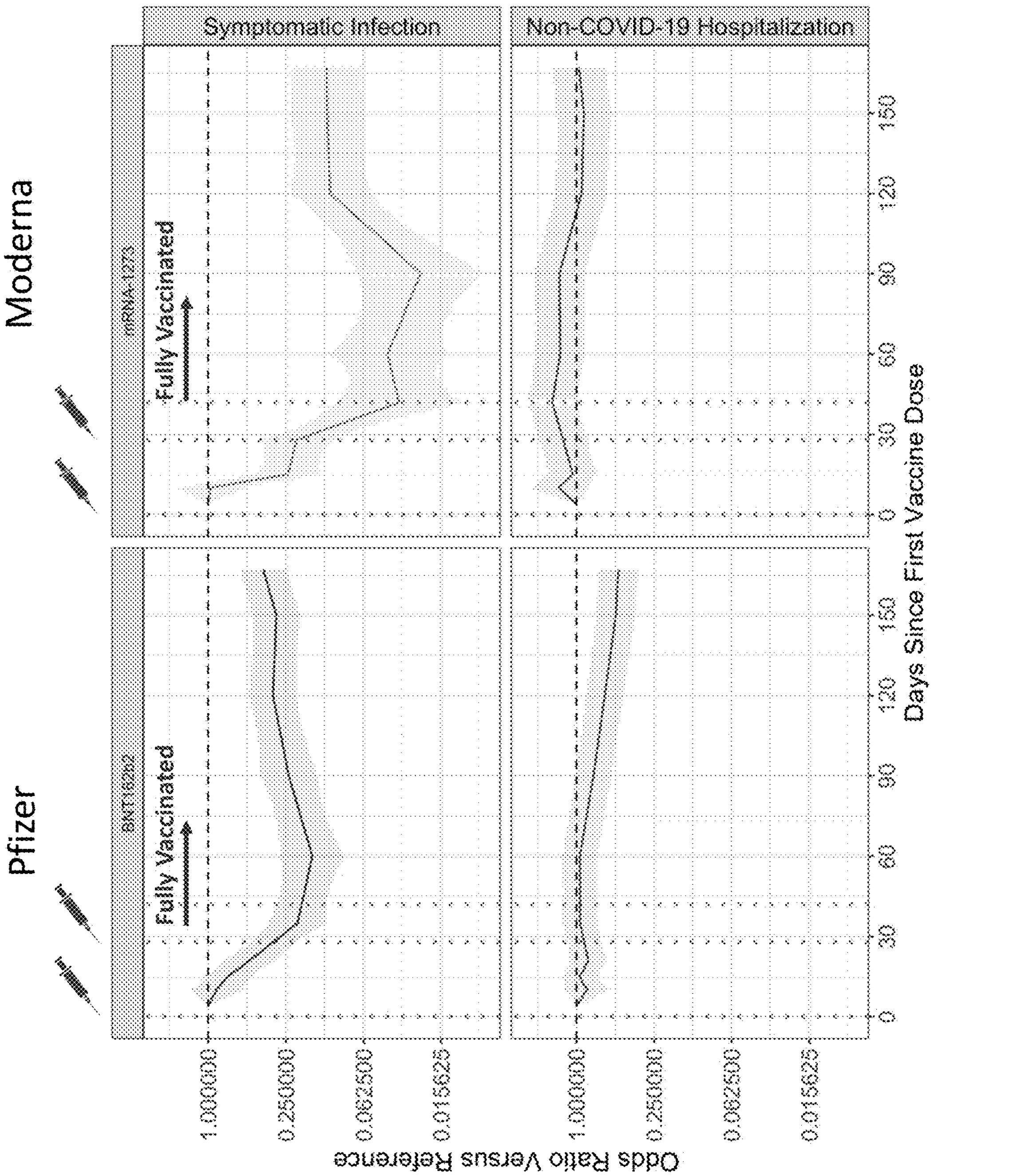
FIG. 28 shows the Odds Ratio as a function of days since first vaccine dose, stratified by the date of testing dose, for symptomatic infection and non-COVID-19 hospitalization, according to certain embodiments.

FIG. 28 shows the Odds Ratio as a function of days since first vaccine dose, stratified by the date of testing, for symptomatic infection and non-COVID-19 hospitalizations.

Figure 29:
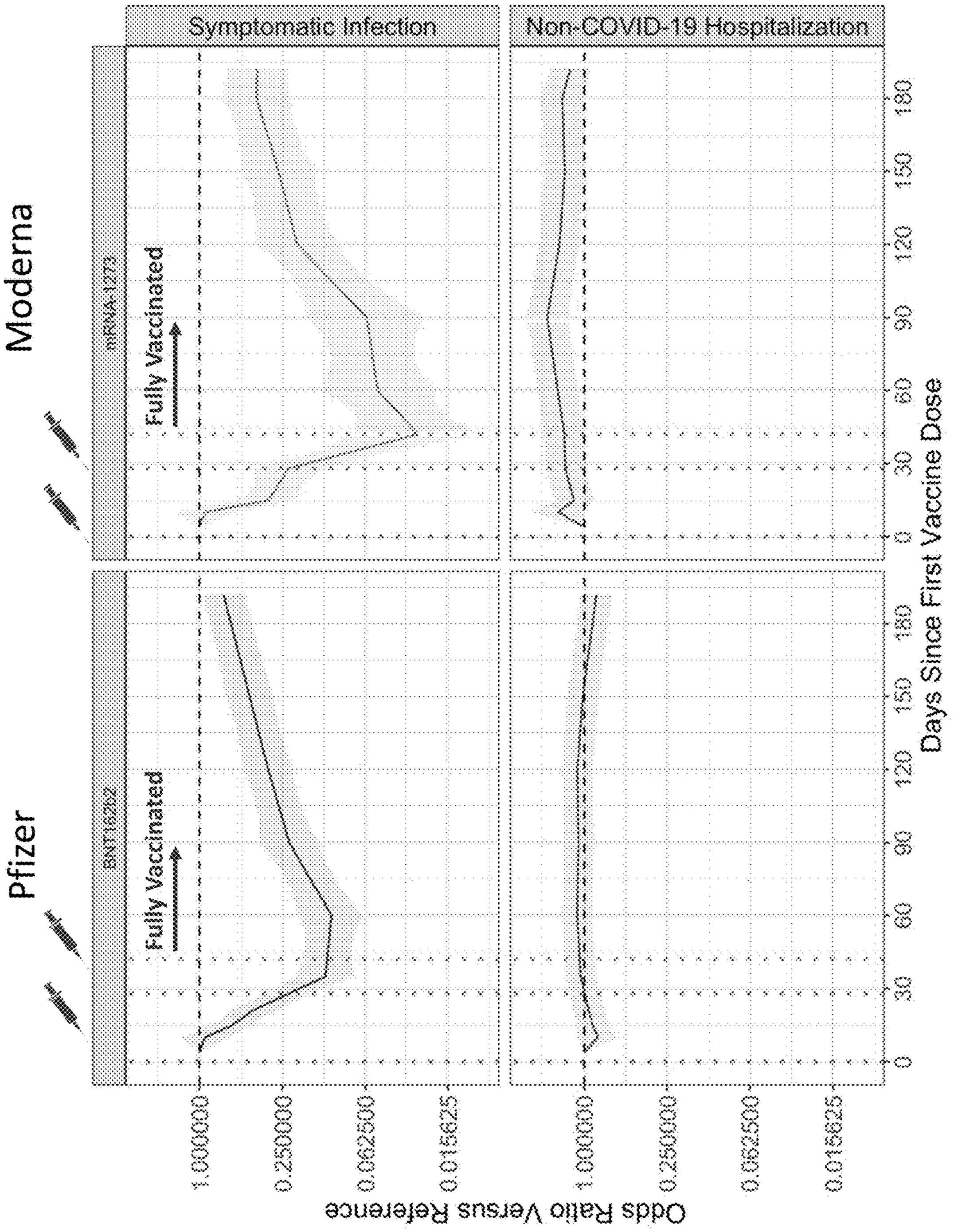
FIG. 29 shows the Odds Ratio as a function of days since first vaccine dose, stratified by the date of vaccination, for symptomatic infection and non-COVID-19 hospitalization, according to certain embodiments.

FIG. 29 shows the Odds Ratio as a function of days since first vaccine dose, stratified by the date of vaccination, for symptomatic infection and non-COVID-19 hospitalizations.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

Those of skill in the art would appreciate that the various illustrations in the specification and drawings described herein can be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware, software, or a combination depends upon the particular application and design constraints imposed on the overall system. Skilled artisans can implement the described functionality in varying ways for each particular application. Various components and blocks can be arranged differently (for example, arranged in a different order, or partitioned in a different way) all without departing from the scope of the subject technology.

Furthermore, an implementation of the communication protocol can be realized in a centralized fashion in one computer system, or in a distributed fashion where different elements are spread across several interconnected computer systems. Any kind of computer system, or other apparatus adapted for carrying out the methods described herein, is suited to perform the functions described herein.

A typical combination of hardware and software could be a general purpose computer system with a computer program that, when being loaded and executed, controls the computer system such that it carries out the methods described herein. The methods for the communications protocol can also be embedded in a non-transitory computer-readable medium or computer program product, which comprises all the features enabling the implementation of the methods described herein, and which, when loaded in a computer system is able to carry out these methods. Input to any part of the disclosed systems and methods is not limited to a text input interface. For example, they can work with any form of user input including text and speech.

Computer program or application in the present context means any expression, in any language, code or notation, of a set of instructions intended to cause a system having an information processing capability to perform a particular function either directly or after either or both of the following a) conversion to another language, code or notation; b) reproduction in a different material form. Significantly, this communications protocol can be embodied in other specific forms without departing from the spirit or essential attributes thereof, and accordingly, reference should be had to the following claims, rather than to the foregoing specification, as indicating the scope of the invention.

The communications protocol has been described in detail with specific reference to these illustrated embodiments. It will be apparent, however, that various modifications and changes can be made within the spirit and scope of the disclosure as described in the foregoing specification, and such modifications and changes are to be considered equivalents and part of this disclosure.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods and media for carrying out the several purposes of the disclosed subject matter. It is important, therefore, that the claims be regarded as including such equivalent constructions insofar as they do not depart from the spirit and scope of the disclosed subject matter.

It will be appreciated that while one or more particular materials or steps have been shown and described for purposes of explanation, the materials or steps may be varied in certain respects, or materials or steps may be combined, while still obtaining the desired outcome. Additionally, modifications to the disclosed embodiment and the invention as claimed are possible and within the scope of this disclosed invention.

The invention claimed is:

1. A method comprising constructing an isolated memory partition that forms a secure enclave, wherein the secure enclave is available to one or more processors for running one or more application computing processes in isolation from one or more unauthorized computing processes running on the one or more processors of the secure enclave;

pre-provisioning software within the secure enclave, wherein the pre-provisioned software within the secure enclave is configured to execute instructions of the one or more application computing processes on the one or more processors of the secure enclave by:

receiving input data for the one or more application computing processes in an encrypted form, wherein the input data comprises, for a plurality of individuals, a vaccination date, a test date, and a test result;

decrypting the input data using one or more cryptographic keys;

executing the one or more application computing processes to generate output data;

generating a proof of execution that proves that the one or more instructions of the one or more application computing processes operated on the received input data; and sending the output data to a central node;

wherein the central node is pre-provisioned with software configured to execute instructions of the one or more application computing processes on one or more processors of the central node by receiving the output data from a plurality of secure enclaves;

executing the one or more application computing processes to apply an aggregate analysis to the output data of each of the plurality of secure enclaves; and providing an aggregate output.

2. The method of claim 1, wherein each of the plurality of secure enclaves is associated with a different health system.

3. The method of claim 1, wherein two or more of the plurality of secure enclaves are associated with two different information systems within a single health system.

4. The method of claim 1, wherein the input data includes at least one of demographic data, comorbidities, and geographic data.

5. The method of claim 1, wherein executing the one or more application computing processes comprises fitting a regression model to the input data to generate output data, wherein the output data comprises at least one of a regression coefficient of the regression model, a standard error for a regression coefficient, and a value calculated from one or more regression coefficients or one or more standard errors.

6. The method of claim 5, wherein the regression model is a stratified model.

7. The method of claim 5, wherein the regression model is a conditional logistical regression model.

8. The method of claim 5, wherein the output comprises the log of an odds ratio at one or more time points and a standard error corresponding to each odds ratio.

9. The method of claim 5, wherein the output comprises a plurality regression coefficients of the regression model.

10. The method of claim 5, wherein the output comprises a covariance matrix of the coefficients of the regression model.

11. The method of claim 5, wherein the output comprises the log of an odds ratio as a continuous function of time.

12. The method of claim 11, wherein the log of the odds ratio as a continuous function of time is estimated based on an interpolation between the log of an odds ratio at two or more time points.

13. The method of claim 1, wherein the pre-provisioned software within the secure enclave is further configured to execute instructions of the one or more application computing processes on the one or more processors of the secure enclave by encrypting the output data using the one or more cryptographic keys; and providing external access to the encrypted output data and the proof of execution.

14. The method of claim 1, wherein the central node is an isolated memory partition available to one or more processors for running one or more application computing processes in isolation from one or more unauthorized computing processes running on the one or more processors of the central node.

15. The method of claim 1, wherein the output data comprises a portion of the input data.

16. The method of claim 1, wherein the aggregate analysis comprises fitting a regression model to the output data, wherein the output data comprises a portion of the input data from each of the plurality of secure enclaves.

17. The method of claim 1, wherein the aggregate analysis comprises inverse variance weighting.

18. The method of claim 5, wherein the aggregate analysis comprises fitting an aggregate regression model to the output data.

19. The method of claim 18, wherein fitting the regression model and fitting the aggregate regression model is iterative.

20. The method of claim 18, wherein the pre-provisioned with software within the central node is configured to execute instructions of the one or more application computing processes on one or more processors of the central node by sending one or more aggregate regression coefficients of the aggregate regression model to each of the plurality of secure enclaves.

21. The method of claim 18, wherein the pre-provisioned software within the secure enclave is further configured to execute instructions of the one or more application computing processes on the one or more processors of the secure enclave by:

receiving one or more aggregate regression coefficients of the aggregate regression model;

tuning the regression model using the one or more aggregate regression coefficients of the aggregate regression model to generate updated output data; and sending the updated output data to a central node.

22. The method of claim 21, wherein the updated output comprises a gradient of one or more regression coefficients of the regression model.

23. The method of claim 1, wherein the aggregate output comprises the log of an odds ratio across the plurality of secure enclaves.

24. The method of claim 1, wherein a vaccination status of an individual is assigned as unvaccinated if the test date is within a predetermined time of the vaccination date and the vaccination status of the individual is assigned as vaccinated if the test date is the predetermined time after the vaccination date.

25. The method of claim 1, wherein the vaccination date includes dates of one or more doses.

26. A system comprising:

a non-transitory memory; and one or more hardware processors configured to read instructions from the non-transitory memory that, when executed cause one or more of the hardware processors to perform operations comprising:

constructing an isolated memory partition that forms a secure enclave, wherein the secure enclave is available to one or more processors for running one or more application computing processes in isolation from one or more unauthorized computing processes running on the one or more processors of the secure enclave;

pre-provisioning software within the secure enclave, wherein the pre-provisioned software within the secure enclave is configured to execute instructions of the one or more application computing processes on the one or more processors of the secure enclave by:

receiving input data for the one or more application computing processes in an encrypted form, wherein the input data comprises, for a plurality of individuals, a vaccination date, a test date, and a test result;

decrypting the input data using one or more cryptographic keys;

executing the one or more application computing processes to generate output data;

generating a proof of execution that proves that the one or more instructions of the one or more application computing processes operated on the received input data; and sending the output data to a central node;

wherein the central node is pre-provisioned with software configured to execute instructions of the one or more application computing processes on one or more processors of the central node by receiving the output data from a plurality of secure enclaves;

executing the one or more application computing processes to apply an aggregate analysis to the output data of each of the plurality of secure enclaves; and providing an aggregate output.

27. The system of claim 26, wherein executing the one or more application computing processes comprises fitting a regression model to the input data to generate output data, wherein the output data comprises at least one of a regression coefficient of the regression model, a standard error for a regression coefficient, and a value calculated from one or more regression coefficients or one or more standard errors.

28. The system of claim 27, wherein the output comprises the log of an odds ratio at one or more time points and a standard error corresponding to each odds ratio.

29. The system of claim 26, wherein the aggregate analysis comprises fitting a regression model to the output data, wherein the output data comprises a portion of the input data from each of the plurality of secure enclaves.

30. The system of claim 26, wherein the aggregate analysis comprises inverse variance weighting.

31. The system of claim 27, wherein the aggregate analysis comprises fitting an aggregate regression model to the output data.

32. A non-transitory computer-readable medium storing instructions that, when executed by one or more hardware processors, cause the one or more hardware processors to perform operations comprising:

constructing an isolated memory partition that forms a secure enclave, wherein the secure enclave is available to one or more processors for running one or more application computing processes in isolation from one or more unauthorized computing processes running on the one or more processors of the secure enclave;

pre-provisioning software within the secure enclave, wherein the pre-provisioned software within the secure enclave is configured to execute instructions of the one or more application computing processes on the one or more processors of the secure enclave by:

receiving input data for the one or more application computing processes in an encrypted form, wherein the input data comprises, for a plurality of individuals, a vaccination date, a test date, and a test result;

decrypting the input data using one or more cryptographic keys;

executing the one or more application computing processes to generate output data;

generating a proof of execution that proves that the one or more instructions of the one or more application computing processes operated on the received input data; and sending the output data to a central node;

wherein the central node is pre-provisioned with software configured to execute instructions of the one or more application computing processes on one or more processors of the central node by receiving the output data from a plurality of secure enclaves;

executing the one or more application computing processes to apply an aggregate analysis to the output data of each of the plurality of secure enclaves; and providing an aggregate output.

33. The computer-readable medium of claim 32, wherein executing the one or more application computing processes comprises fitting a regression model to the input data to generate output data, wherein the output data comprises at least one of a regression coefficient of the regression model, a standard error for a regression coefficient, and a value calculated from one or more regression coefficients or one or more standard errors.

34. The computer-readable medium of claim 33, wherein the output comprises the log of an odds ratio at one or more time points and a standard error corresponding to each odds ratio.

35. The computer-readable medium of claim 32, wherein the aggregate analysis comprises fitting a regression model to the output data, wherein the output data comprises a portion of the input data from each of the plurality of secure enclaves.

36. The computer-readable medium of claim 32, wherein the aggregate analysis comprises inverse variance weighting.

37. The computer-readable medium of claim 33, wherein the aggregate analysis comprises fitting an aggregate regression model to the output data.

* * * * *